US012617813B2

(12) United States Patent
Oyelere et al.

(10) Patent No.: US 12,617,813 B2
(45) Date of Patent: May 5, 2026

(54) GLYCOSYLATED HISTONE DEACETYLASE INHIBITORS AND METHODS OF MAKING AND USING THE SAME

(71) Applicant: Georgia Tech Research Corporation, Atlanta, GA (US)

(72) Inventors: Adegboyega Oyelere, Atlanta, GA (US); Subhasish Tapadar, Atlanta, GA (US); Bocheng Wu, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 392 days.

(21) Appl. No.: 18/266,438

(22) PCT Filed: Dec. 28, 2021

(86) PCT No.: PCT/US2021/065325
§ 371 (c)(1),
(2) Date: Jun. 9, 2023

(87) PCT Pub. No.: WO2022/146994
PCT Pub. Date: Jul. 7, 2022

(65) Prior Publication Data

US 2024/0059726 A1 Feb. 22, 2024

Related U.S. Application Data

(60) Provisional application No. 63/131,122, filed on Dec. 28, 2020.

(51) Int. Cl.

| | |
|---|---|
| ***C07H 15/203*** | (2006.01) |
| ***A61P 35/00*** | (2006.01) |
| ***C07H 15/26*** | (2006.01) |

(52) U.S. Cl.
CPC ............ *C07H 15/203* (2013.01); *A61P 35/00* (2018.01); *C07H 15/26* (2013.01)

(58) Field of Classification Search
CPC .................................................. A61K 31/7048
USPC ........................................... 514/27; 536/17.4
See application file for complete search history.

(56) References Cited

U.S. PATENT DOCUMENTS

| | | | | |
|---|---|---|---|---|
| 2010/0197622 A1 | 8/2010 | Oyelere | | |
| 2012/0329741 A1* | 12/2012 | Oyelere | .................. | A61P 33/00 548/255 |

FOREIGN PATENT DOCUMENTS

| | | | |
|---|---|---|---|
| CN | 101648924 | B | 2/2010 |
| CN | 106883217 | B | 6/2017 |
| WO | 03/018598 | A2 | 3/2003 |
| WO | 2009006403 | A2 | 1/2009 |
| WO | 2014194270 | A1 | 12/2014 |

OTHER PUBLICATIONS

Extended European Search Report pursuant to Rule 62 EPC in related European Patent Application No. 221 916 356.5, dated Sep. 11, 2024 (11 pages).
International Search Report and Written Opinion from Application No. PCT/US2021/065325 dated May 4, 2022.
Pubchem-SID:277310636 Jan. 6, 2016 pp. 1-6.
Pubchem-SID:275710981 Dec. 26, 2015 pp. 1-6.

* cited by examiner

*Primary Examiner* — Traviss C McIntosh, III
(74) *Attorney, Agent, or Firm* — Troutman Pepper Locke LLP; Ryan A. Schneider; Nicholas H. Doss

(57) ABSTRACT

Provided herein are glycosylated compounds as histone deacetylase (HDACi) inhibitors or a diastereomer, solvate, or a pharmaceutically acceptable salt thereof. Also provided are pharmaceutical compositions and medicaments that include the compounds described herein as well as methods of treating inflammatory disease and cancer.

19 Claims, 8 Drawing Sheets

GLYCOSYLATED HISTONE DEACETYLASE INHIBITORS AND METHODS OF MAKING AND USING THE SAME

STATEMENT REGARDING FEDERALLY SPONSORED RESEARCH

This invention was made with government support under NIH RO1 CA131217 awarded by the National Institutes of Health. The government has certain rights in the invention.

TECHNICAL FIELD OF THE INVENTION

Aspects of the invention are generally directed to small molecule inhibitors of the histone deacetylase (HDACi) and methods of making and using thereof.

BACKGROUND OF THE INVENTION

Histone deacetylases (HDACs) and histone acetyl transferase (HAT) are functionally opposing epigenetic regulators which control the acetylation states on histones and several non-histone proteins. HDACs, as part of multiprotein complexes, facilitate the removal of acetyl groups from the ε-amino groups of specific lysine residues of nucleosomal core histones and other proteins (Gryder, B.; Sodji, Q. H.; Oyelere, A. K. Targeted Cancer Therapy: Giving Histone Deacetylase Inhibitors All They Need to Succeed. *Future Med. Chem.* 4, 505-524 (2012)). Eighteen HDAC isoforms have been identified to date in human cells. These HDACs are grouped into four classes based on their homology to three Saccharomyces cerevisiae HDACs (RPD3, HDA1, and SIR2). Class I HDACs (HDACs 1, 2, 3 and 8); Class II HDACs (HDACs 4, 5, 6, 7, 9 and 10) and Class IV (HDAC 11) are zinc-dependent protein deacetylases. The Class III of HDACs consist of the sirtuins (SIRT 1-7), which are homologically distinct from the other HDACs and are $NAD^+$-dependent deactylases (Yoshida, M.; Kudo, N.; Kosono, S.; Ito, A. Chemical and structural biology of protein lysine deacetylases. *Proc. Jpn. Acad., Ser. B* 93, 297-321 (2017)).

Dysfunction in the activities of HDACs have been linked to several diseases including cancers, inflammation disorders, tissue fibrosis, cognitive disorders, cardiovascular diseases, neurological diseases and parasitic protozoan's diseases such as malaria, Chagas, trypanosomiasis and leishmaniasis. While several of these disease states could benefit from the inhibition of HDACs activities, much attention has been directed towards cancers (Gryder, B.; Sodji, Q. H.; Oyelere, A. K. Targeted Cancer Therapy: Giving Histone Deacetylase Inhibitors All They Need to Succeed. *Future Med. Chem.* 4, 505-524 (2012)). Specifically, upregulation of HDAC activities, which results in silencing of tumor suppressor genes and uncontrolled proliferation, predominates in malignant tumors. One of the early examples of small molecule HDAC inhibitor (HDACi) was reported by Yoshida et al. who showed that the natural product (R)-trichostatin A induced cell differentiation of murine erythroleukemia cells and hyperacetylation of histone proteins at nanomolar concentrations (Yoshida, M.; Kijima, M.; Akita, M.; Beppu, T., *J. Biol. Chem.* 265, 17174-17179 (1990); Yoshida, M.; Hoshikawa, Y.; Koseki, K.; Mori, K.; Beppu, T., *J. Antibiot.* 43, 1101-1106 (1990)). Subsequently, several HDAC inhibitors (HDACi) have been reported by other researchers (West, A. C.; Johnstone, R. W. *J. Clin. Invest.* 124, 30-39 (2014); Eckschlager, R.; Plch, J.; Stiborova, M.; Hrabeta, J. Histone Deacetylase Inhibitors as Anticancer Drugs. *Int. J. Mol. Sci.* 18, 1414 (2017)). These prior reports have contributed to the clinical validation of HDAC inhibition as cancer therapy strategy with the approval of Vorinostat, Romidepsin, Belinostat, Chidamide and Panabinostat (Tapadar, S.; Fathi, S.; Raji, I.; Omesiete, W.; Kornacki, J. R.; Mwakwari, S. C.; Miyata, M.; Mitsutake, K.; Li, J.-D.; Mrksich, M.; Oyelere, A. K. A structure-activity relationship of non-peptide macrocyclic histone deacetylase inhibitors and their antiproliferative and anti-inflammatory activities. *Bioorg. Med. Chem.* 23, 7543-7564 (2015)). However, current HDACi have elicited limited therapeutic benefit against most solid tumors.

HDACi have elicited antiproliferative activities against nearly all transformed cell types, including epithelial (melanoma, lung, breast, pancreas, ovary, prostate, colon and bladder) and hematological (lymphoma, leukemia and multiple myeloma) tumors (Kelly, W. K; O'Connor, O. A.; Marks, P. A., *Expert. Opin. Investig. Drugs,* 11, 1695-1713 (2002)).

Similar to other cancers, liver cancers including hepatocellular carcinoma (HCC) and cholangiocarcinoma, are driven by genetic mutations and epigenetic dysfunctions including gene-silencing chromatin histone hypoacetylation (Rikimaru, T.; Taketomi, A.; Yamashita, Y.; Shirabe, K.; Hamatsu, T.; Shimada, M.; Maehara, Y. Clinical significance of histone deacetylase 1 expression in patients with hepatocellular carcinoma. *Oncology* 72, 69-74 (2007); Ma, B. B.; Sung, F.; Tao, Q.; Poon, F. F.; Lui, V. W.; Yeo, W.; Chan, S. L.; Chan, A. T. The preclinical activity of the histone deacetylase inhibitor PXD101 (belinostat) in hepatocellular carcinoma cell lines. *Invest New Drugs* 28, 107-114 (2010); Yeo, W.; Chung, H. C.; Chan, S. L.; Wang, L. Z. et al Epigenetic Therapy Using Belinostat for Patients With Unresectable Hepatocellular Carcinoma: A Multicenter Phase I/II Study With Biomarker and Pharmacokinetic Analysis of Tumors From Patients in the Mayo Phase II Consortium and the Cancer Therapeutics Research Group. *J Clin Oncol.* 30, 3361-3367 (2012); Sun, T-Y.; Xie, H-J.; Li, Z.; et al. Analysis of miRNAs related to abnormal HDAC1 expression in hepatocellular carcinoma. *Int J Clin Exp Med* 9, 21482-21489 (2016); Freese, K.; Seitz, T.; Dietrich, P.; et al. Histone Deacetylase Expressions in Hepatocellular Carcinoma and Functional Effects of Histone Deacetylase Inhibitors on Liver Cancer Cells *In Vitro. Cancers* (*Basel*) 11, 1587 (2019)). The vital roles of HDACs, particularly sub-members of class I HDAC, in the development and sustenance of liver cancers makes HDAC inhibition a potentially valid therapeutic strategy for liver cancers.

Liver cancer is the fourth leading cause of global cancer deaths in 2018, with an estimated 841,000 new cases and 782,000 deaths (Bray, F.; Ferlay, J.; Soerjomataram, I.; Siegel, R. L.; Torre, L. A.; Jemal, A. Global Cancer Statistics 2018: GLOBOCAN Estimates of Incidence and Mortality Worldwide for 36 Cancers in 185 Countries. CA: a cancer journal for clinicians. doi: 10.3322/caac.2149 (2018)). Liver cancer incidence and mortality are 2 to 3 times higher among men in most regions of the world. Although the majority of liver cancer cases occur in developing countries, there is an upward trend in liver carcinomas in the United States (US) and other developed countries. In the US, a 2-fold age adjusted increase in liver cancer incidence was observed between 1981 and 1995. Since 1980 liver cancer incidence rates have more than triple; with a steeper upward trend from 2006 to 2015 when the rate increased by about 3% per year. From 2005 to 2014, the death rate for liver cancer increased by 3% per year. Increases in the prevalence of obesity and diabetes have been recognized as risk factors that may contribute to the more recent liver cancer trends. In 2019, about 42,030 new cases are expected in the US; of these newly diagnosed patients, 31,780 will succumb to this disease. Based on these clinical and epidemiological observations, liver cancer is the most rapidly increasing cancer in both men and women in the US.

Cancer cells rely on the constant supply of multiple fuel molecules, including glucose and fructose, to sustain their high metabolic rate. To meet their energy demands, glucose transporter (GLUT) family of proteins are overexpressed in several cancer cells. Fourteen known glucose transporters (GLUTs) have been identified to date and these GLUTs are expressed in tissue dependent manner (Mueckler, M.; Thorens, B. The SLC2 (GLUT) family of membrane transporters. *Mol Aspects Med.* 34:121-138 (2013)). Among these GLUTs, GLUT2 is a high capacity GLUT primarily expressed in the liver and to some extent in the pancreatic β-cells, kidney and small intestine (Thorens, B.; Cheng, Z. Q.; Brown, D.; Lodish, H. F. Liver glucose transporter: a basolateral protein in hepatocytes and intestine and kidney cells. *Am J Physiol.* 259(6 Pt 1):C279-285 (1990); Thorens, B. GLUT2, glucose sensing and glucose homeostasis. *Diabetologia* 58, 221-232 (2015)). GLUT2 is indispensable for glucose uptake by the liver (Mueckler, M.; Thorens, B. The SLC2 (GLUT) family of membrane transporters. *Mol Aspects Med.* 34:121-138 (2013)). In addition to glucose, GLUT2 can transport other sugars, including glucosamine, galactose, mannose and fructose (Uldry, M.; Ibberson, M.; Hosokawa, M.; Thorens, B. GLUT2 is a high affinity glucosamine transporter. FEBS Lett. 524:199-203 (2002); Mueckler, M.; Thorens, B. The SLC2 (GLUT) family of membrane transporters. *Mol Aspects Med.* 34:121-138 (2013)). More recently, it has been shown that the GLUT2 expression is much higher in HCC than those of other members of the GLUT family and that GLUT2 could constitute a prognosis biomarker for HCC (Kim, Y. H.; Jeong, D. C.; Pak, K.; Han, M. E.; Kim, J. Y.; Liangwen, L.; et al. SLC2A2 (GLUT2) as a novel prognostic factor for hepatocellular carcinoma. *Oncotarget* 8, 68381-68392 (2017)).

It is therefore an object of the invention to provide glycosylated small molecule HDAC inhibitors having improved efficacy toward cancers, more specifically liver cancers, and methods of making and using thereof.

SUMMARY OF THE INVENTION

Glycosylated histone deacetylase inhibitors (HDACi) compositions and methods of their use are provided.

One embodiment provides a compound of Formula I:

Formula I

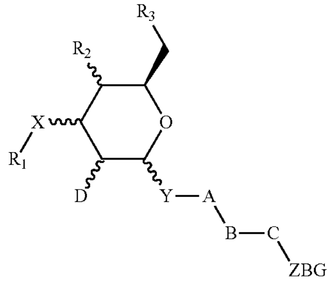

wherein

X is O or $NCH_3$;

$R_1$ is each independently H, $C_{1-6}$ alkyl, $C_{1-6}$ alkanoate, $C_{2-6}$ carbamate, $C_{5-6}$ aryl ester, optionally substituted with heteroatoms;

$R_2$ and $R_3$ are each independently H, OH or $OR_4$;

$R_4$ is each independently $C_{1-6}$ alkyl, $C_{1-6}$ alkanoate, $C_{2-6}$ carbamate, $C_{5-6}$ aryl ester, optionally substituted with heteroatoms;

Y is O, S, $CH_2$ or is absent;

A is each independently substituted or unsubstituted an alkyl, an aryl ring, heteroaryl ring, or is absent;

B is amide, reverse amide, ester, reverse ester, alkoxyl, sulfanyl, sulfinyl, sulfonyl, sulfonamido, ketone, $S_P3$ hybridized carbon, $S_P2$ hybridized carbon, $S_P$ hybridized carbon, 5 or 6 membered substituted or unsubstituted heteroaryl rings, 1,2,3-triazolyl, 1,2,4-triazolyl, 1-tetrazolyl, 1-indolyl, 1-indazolyl, 2-isoindolyl, 7-oxo-2-isoimdolyl,1-pirinyl, 3-isothiazolyl, 4-isothiazolyl, 5-isothiazolyl, 1,3,4,-oxadiazole, 4-oxo-2-thiazolinyl, or 5-methyl-1.3,4-thiadiazol-2-yl, thiazoledione, 1,2,3,4-thiatriazole, 1,2,4-dithiazolone, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazolyl, 2-quinolyl. 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, 3-pyrazolyl 4-pyrazolyl, 5-pyrazolyl, 2-oxazolyl, 4-oxazolyl, 4-oxo-2-oxazolyl, 5-oxazolyl, 4,5-dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole, benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 1-pyrrolyl, and 1-pyrazolyl;

C is $—CH_2—$, $C_{2-8}$ alkyl, aryl or heteroaryl, optionally substituted with one or more double or triple bonds;

D is each independently H, F, OH, $OCOCH_3$, $NH_2$, $OR_5$, $NHR_5$;

$R_5$ is $C_{1-6}$ alkanoate, $C_{2-6}$ carbamate, $C_{5-6}$ aryl ester optionally substituted with heteroatoms, $C_{5-6}$ fused aryl ester optionally substituted with heteroatoms; and ZBG is hydroxamates, N-formyl hydroxylamine (or retrohydroxamate), carboxylates, thiols, dithiols, trithiocarbonates, thioesters, benzamide, halo- or heteroaryl-substituted N-(2-amino-phenyl)acylamide, keto, mercaptoacetamides, 2-ketoamides, epoxides, epoxyketones, trifluoromethyl ketones, hydroxypyridinones, pyrones, hydroxylpyridinethiones, and thiopyrones; or a diastereomer, solvate, or a pharmaceutically acceptable salt thereof.

Another embodiment provides a process for preparing a compound of formula I.

Still another embodiment provides a pharmaceutical composition containing a compound of formula I or a pharmaceutically acceptable salt thereof, and optionally a pharmaceutically acceptable carrier, adjuvant or vehicle.

Still another embodiment provides a method of inhibiting histone deacetylases, the method including the steps of contacting the cells producing histone deacetylase with a compound according to formula I or a pharmaceutical composition thereof.

Another embodiment provides a method of treating a histone deacetylase dysfunction-driven disease, disorder or condition in a subject in need thereof by administering to the subject a therapeutically effective amount of the compound of formula I or a pharmaceutical composition thereof.

In another aspect, the histone deacetylase dysfunction-driven disease, disorder or condition is an inflammatory disease or cancer.

One embodiment provides a method of treating an inflammatory disease, disorder or condition in a subject in need thereof by administering to the subject a therapeutically effective amount of the compound of formula I or a pharmaceutical composition thereof.

Yet another embodiment provides a method of treating a cancer in a subject in need thereof by administering to the subject a therapeutically effective amount of the compound of formula I or a pharmaceutical composition thereof.

BRIEF DESCRIPTION OF THE DRAWINGS

FIG. 4 shows that the cell cycle arrest was caused by the representative compound, STR-V-53.

FIG. 5 shows that GLUT2 contributes to the uptake of STR-V-53 in Hep-G2 cell line. Blockage of GLUT2 attenuates the cytotoxicity of STR-V-53 against Hep-G2. Hep-G2 and VERO were treated with Phloretin (Ph) for 24 h prior to incubation with STR-V-53 or SAHA.

DETAILED DESCRIPTION OF THE INVENTION

I. Definitions

Figure 1A:
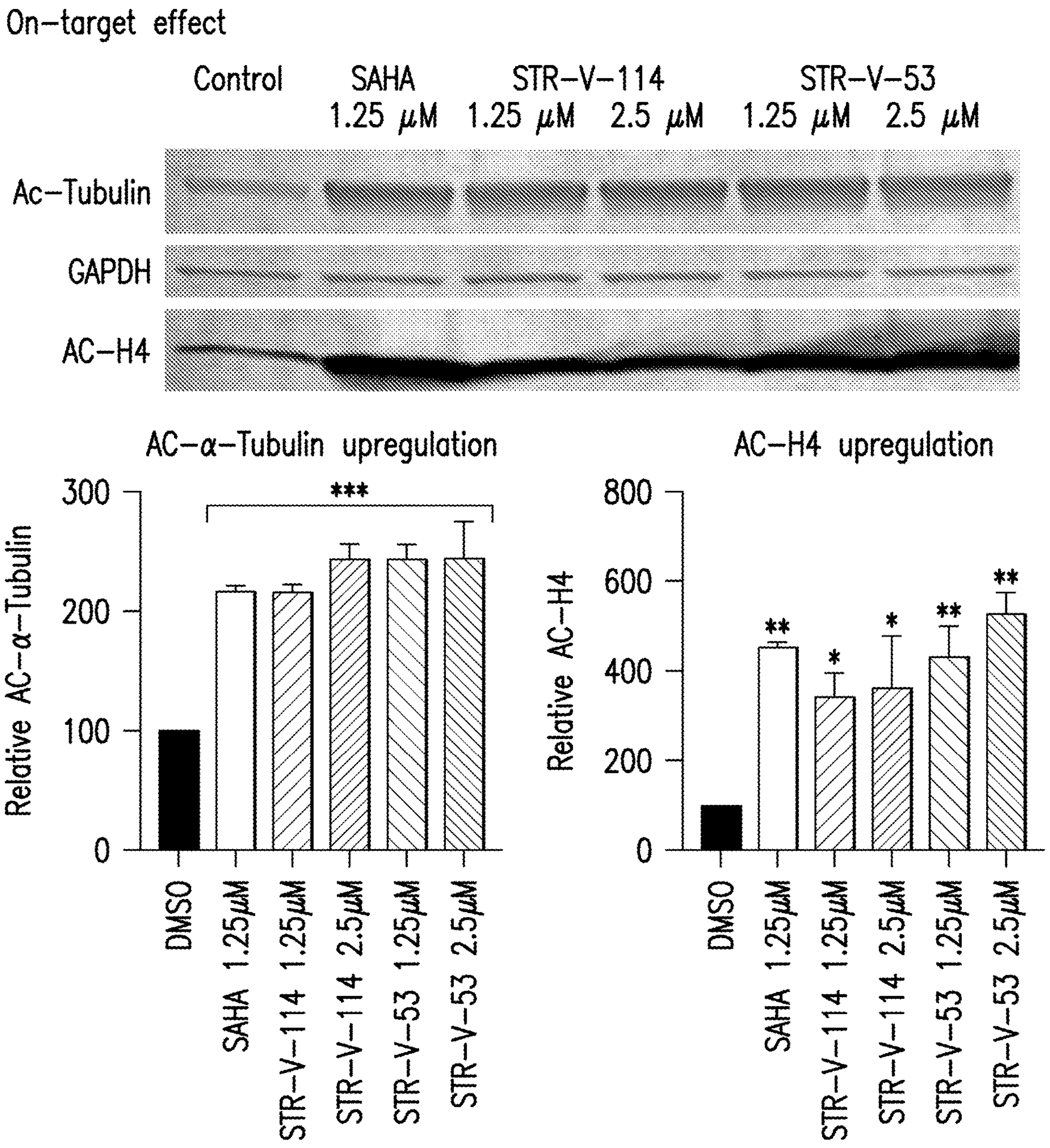
FIG. 1 shows that the Western blot evidence of on-target effect (HDAC inhibition) of representative compounds, STR-V-53, STR-V-114 and STR-I-195 through upregulation of acetylated tubulin and histone H4 in Hep-G2 cells.

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term 'substituted' is to be defined as set out below. It should be further understood that the terms "groups" and "radicals" can be considered interchangeable when used herein.

The articles "a" and "an" may be used herein to refer to one or to more than one (i.e., at least one) of the grammatical objects of the article. By way of example "an analogue" means one analogue or more than one analogue.

As used herein, the term "pharmaceutical composition" means a mixture comprising a pharmaceutically acceptable active ingredient, in combination with suitable pharmaceutically acceptable excipients.

Pharmaceutical excipients are substances other than the pharmaceutically acceptable active ingredient which have been appropriately evaluated for safety and which are intentionally included in an oral solid dosage form. For example, excipients can aid in the processing of the drug delivery system during its manufacture, protect, support or enhance stability, bioavailability or patient acceptability, assist in product identification, or enhance any other attribute of the overall safety, effectiveness or delivery of the drug during storage or use. Examples of excipients include, for example but without limitation inert solid diluents (bulking agent e.g., lactose), binders (e.g., starch), glidants (e.g., colloidal silica), lubricants (e.g., non-ionic lubricants such as vegetable oils), disintegrants (e.g., starch, polivinylpyrrolidone), coating better polymers (e.g., hydroxypropyl methylcellulose), colorants (e.g., iron oxide), and/or surfactants (e.g., non-ionic surfactants).

As used herein, the term "pharmaceutical formulation" means a composition in which different chemical substances, including the active drug, are combined to produce a final medicinal product. Examples of formulation include enteral formulations (tablets, capsules), parenteral formulations (liquids, lyophilized powders), or topical formulations (cutaneous, inhalable).

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt or derivatives thereof that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethane sulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. More particularly, such salts are formed with hydrobromic acid, hydrochloric acid, sulfuric acid, toluenesulfonic acid, benzenesulfonic acid, oxalic acid, maleic acid, naphthalene-2-sulfonic acid, naphthalene-1,5-disulfonic acid, 1-2-ethane disulfonic acid, methanesulfonic acid, 2-hydroxy ethanesulfonic acid, phosphoric acid, ethane sulfonic acid, malonic acid, 2-5-dihydroxybenzoic acid, or L-Tartaric acid.

The term "pharmaceutically acceptable cation" refers to an acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Solvate" refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances, the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

The terms "inert solid diluent" or "solid diluent" or "diluents" refer to materials used to produce appropriate dosage form size, performance and processing properties for tablets and/or capsules. An inert solid diluent can be also referred to as filler or filler material. Particular examples of diluents include cellulose powdered, silicified microcrystalline cellulose acetate, compressible sugar, confectioner's sugar, corn starch and pregelatinized starch, dextrates, dextrin, dextrose, erythritol, ethylcellulose, fructose, fumaric acid, glyceryl palmitostearate, inhalation lactose, isomalt, kaolin, lactitol, lactose, anhydrous, monohydrate and corn starch, spray dried monohydrate and microcrystalline cellulose, maltodextrin, maltose, mannitol, medium-chain triglycerides, microcrystalline cellulose, polydextrose, polymethacrylates, simethicone, sorbitol, pregelatinized starch, sterilizable maize, sucrose, sugar spheres, sulfobutylether β-cyclodextrin, talc, tragacanth, trehalose, or xylitol. More particular examples of diluents include cellulose powdered, silicified microcrystalline cellulose acetate, compressible sugar, corn starch and pregelatinized starch, dextrose, fructose, glyceryl palmitostearate, anhydrous, monohydrate and corn starch, spray dried monohydrate and microcrystalline cellulose, maltodextrin, maltose, mannitol, medium-chain triglycerides, microcrystalline cellulose, polydextrose, sorbitol, starch, pregelatinized, sucrose, sugar spheres, trehalose, or xylitol.

"Lubricant" refers to materials that prevent or reduce ingredients from clumping together and from sticking to the tablet punches or capsule filling machine. Lubricants also ensure that tablet formation and ejection can occur with low friction between the solid and die wall. Particular examples of lubricants include canola oil, hydrogenated castor oil, cottonseed oil, glyceryl behenate, glyceryl monostearate, glyceryl palmitostearate, medium-chain triglycerides, mineral oil, light mineral oil, octyldodecanol, poloxamer, polyethylene glycol, polyoxyethylene stearates, polyvinyl alcohol, starch, or hydrogenated vegetable oil. More particular examples of diluents include glyceryl behenate, glyceryl monostearate, or hydrogenated vegetable oil.

"Disintegrant" refers to material that dissolve when wet causing the tablet to break apart in the digestive tract, releasing the active ingredients for absorption. They ensure that when the tablet is in contact with water, it rapidly breaks down into smaller fragments, facilitating dissolution. Particular examples of disintegrants include alginic acid, powdered cellulose, chitosan, colloidal silicon dioxide, corn starch and pregelatinized starch, crospovidone, glycine, guar gum, low-substituted hydroxypropyl cellulose, methylcellulose, microcrystalline cellulose, or povidone.

The term "colorant" describes an agent that imparts color to a formulation. Particular examples of colorants include iron oxide, or synthetic organic dyes (US Food and Drug administration, Code of Federal Regulations, Title 21 CFR Part73, Subpart B).

The term "plasticizing agent" or "plasticizer" refers to an agent that is added to promote flexibility of films or coatings. Particular examples of plasticizing agent include polyethylene glycols or propylene glycol.

The term "pigment" in the context of the present invention refers to an insoluble coloring agent.

The term "film-coating agent" or 'coating agent' or 'coating material' refers to an agent that is used to produce a cosmetic or functional layer on the outer surface of a dosage form. Particular examples of film-coating agent include glucose syrup, maltodextrin, alginates, or carrageenan.

"Glidant" refers to materials that are used to promote powder flow by reducing interparticle friction and cohesion. These are used in combination with lubricants as they have no ability to reduce die wall friction. Particular examples of glidants include powdered cellulose, colloidal silicon dioxide, hydrophobic colloidal silica, silicon dioxide, or talc. More particular examples of glidants include colloidal silicon dioxide, hydrophobic colloidal silica, silicon dioxide, or talc.

"Flavoring agents" refers to material that can be used to mask unpleasant tasting active ingredients and improve the acceptance that the patient will complete a course of medication. Flavorings may be natural (e.g., fruit extract) or artificial. Non limiting examples of flavoring agents include mint, cherry, anise, peach, apricot, licorice, raspberry, or vanilla.

The term "Subject" includes mammals such as humans. The terms "human", "patient" and "subject" are used interchangeably herein.

"Effective amount" means the amount of a compound of the invention that, when administered to a subject for treating a disease, is sufficient to effect such treatment for the disease. The 'effective amount' can vary depending on the compound, the disease and its severity, and the age, weight, etc., of the subject to be treated.

"Preventing" or "prevention" refers to a reduction in risk of acquiring or developing a disease or disorder (i.e., causing at least one of the clinical symptoms of the disease not to develop in a subject that may be exposed to a disease-causing agent, or predisposed to the disease in advance of disease onset).

The term “prophylaxis” is related to “prevention”, and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

“Treating” or “treatment” of any disease or disorder refers, in one embodiment, to ameliorating the disease or disorder (i.e., arresting the disease or reducing the manifestation, extent or severity of at least one of the clinical symptoms thereof). In another embodiment “treating” or “treatment” refers to ameliorating at least one physical parameter, which may not be discernible by the subject. In yet another embodiment, “treating” or “treatment” refers to modulating the disease or disorder, either physically, (e.g., stabilization of a discernible symptom), physiologically, (e.g., stabilization of a physical parameter), or both. In a further embodiment, “treating” or “treatment” relates to slowing the progression of the disease.

As used herein, the term “isotopic variant” refers to a compound that contains unnatural proportions of isotopes at one or more of the atoms that constitute such compound. For example, an “isotopic variant” of a compound can contain one or more non-radioactive isotopes, such as for example, deuterium ($^{2}H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^{2}H$/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e., $^{3}H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron, and 13 Emission Topography (PET) studies for examining substrate receptor occupancy.

All isotopic variants of the compounds provided herein, radioactive or not, are intended to be encompassed within the scope of the invention.

“Tautomers” refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

The term “alkyl” as used herein, whether used alone or as part of another group, refers to a substituted or unsubstituted aliphatic hydrocarbon chain and includes, but is not limited to, straight and branched chains containing from 1 to 20 carbon atoms, preferably from 2 to 20, from 1 to 10, from 2 to 10, from 1 to 8, from 2 to 8, from 1 to 6, from 2 to 6, from 1 to 4, from 2 to 4, from 1 to 3 carbon atoms, unless explicitly specified otherwise. Illustrative alkyl groups can include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4-dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

The term “alkenyl” as used herein, whether used alone or as part of another group, refers to a substituted or unsubstituted aliphatic hydrocarbon chain and includes, but is not limited to, straight and branched chains having 2 to 8 carbon atoms and containing at least one carbon-carbon double bond.

The term “alkynyl” as used herein, whether used alone or as part of another group, refers to a substituted or unsubstituted aliphatic hydrocarbon chain and includes, but is not limited to, straight and branched chains having 1 to 6 carbon atoms and containing at least one carbon-carbon triple bond.

The term “alkoxy” as used herein, whether used alone or as part of another group, refers to alkyl-O— wherein alkyl is hereinbefore defined.

The term “cycloalkyl” as used herein, whether used alone or as part of another group, refers to a monocyclic, bicyclic, tricyclic, fused, bridged or spiro monovalent saturated hydrocarbon moiety, wherein the carbon atoms are located inside or outside of the ring system. Any suitable ring position of the cycloalkyl moiety may be covalently linked to the defined chemical structures. Illustrative cycloalkyl groups can include, but are not limited to, cyclopropyl, cyclopropylmethyl, cyclobutyl, cyclopentyl, cyclohexyl, cyclohexylmethyl, cyclohexylethyl, cycloheptyl, norbornyl, adamantly, spiro[4,5]decanyl, and homologs, isomers and the alike.

The term “aryl” as used herein, whether used alone or as part of another group, refers to an aromatic carbocyclic ring system having 6 to 30 carbon atoms, preferably 6 to 10 carbon atoms, 6- and 7-membered aromatic, heterocyclic, fused aromatic, fused heterocyclic, biaromatic, or bihetereocyclic ring system, optionally substituted with 1 to 3 substituents independently selected from halogen, nitro cyano, hydroxy, alkyl, alkenyl, alkoxy, cycloalkyl, amino, alkylamino, dialkylamino, carboxy, alkoxycarbonyl, haloalkyl, and phenyl.

The term “phenyl” as used herein, whether used alone or as part of another group, refers to a substituted or unsubstituted phenyl group.

The term “heteroaryl” as used herein, whether used alone or as part of another group, refers to a 3 to 30 membered aryl heterocyclic ring, which contains from 1 to 4 heteroatoms selected from the group consisting of O, N, Si, P and S atoms in the ring and may be fused with a carbocyclic or heterocyclic ring at any possible position.

The term “heterocycloalkyl” as used herein, whether used alone or as part of another group, refers to a 5 to 7 membered saturated ring containing carbon atoms and from 1 to 2 heteroatoms selected from the group consisting of O, N and S atoms.

The term “halogen or halo” as used herein, refers to fluoro, chloro, bromo or iodo.

The term "haloalkyl" as used herein, whether used alone or as part of another group, refers to an alkyl as hereinbefore defined, independently substituted with 1 to 3, F, Cl, Br or I.

"Zinc binding group" or "ZBG", as used herein, refers to moieties capable of inhibiting zinc metalloenzymes activity including HDAC and matrix metalloproteinase (MMP) activity. Suitable examples include, but are not limited to, hydroxamates, N-formyl hydroxylamine (or retro-hydroxamate), carboxylates, thiols, dithiols, trithiocarbonates, thioesters, benzamide, halo- or heteroaryl-substituted N-(2-amino-phenyl)acylamide, keto, mercaptoacetamides, 2-ketoamides, epoxides, epoxyketones, trifluoromethyl ketones, hydroxypyridinones, pyrones, hydroxylpyridinethiones, and thiopyrones.

The term "about" as used herein, refers that the numerical value is approximate and small variations would not significantly affect the practice of the disclosed embodiments. Where a numerical limitation is used, unless indicated otherwise by the context, "about" means the numerical value can vary by ±20% and remain within the scope of the disclosed embodiments. Additionally, in phrase "about X to Y," is the same as "about X to about Y," that is the term "about" modifies both "X" and "Y."

The term "compound" as used herein, refers to salts, solvates, complexes, isomers, stereoisomers, diastereoisomers, tautomers, and isotopes of the compound or any combination thereof.

The term "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are used in their inclusive, open-ended, and non-limiting sense.

A diastereomer is a stereoisomer with two or more stereocenters, and the isomers are not mirror images of each other.

Histone deacetylases (HDACs) represents an attractive target for treating chronic inflammatory disorders. Indeed, a role for histone deacetylases has been demonstrated in a variety of inflammatory disorders, including, but not limited to, acute and chronic inflammatory disorders, sepsis, acute endotoxemia, encephalitis, Chronic Obstructive Pulmonary Disease (COPD), allergic inflammatory disorders, asthma, pulmonary fibrosis, arthritis, rheumatoid arthritis, osteoarthritis, inflammatory osteolysis, ulcerative colitis, psoriasis, vasculitis, autoimmune disorders, thyroiditis, Meliodosis, (mesenteric) Ischemia reperfusion, and in particular Inflammatory Bowel Disease (IBD).

Inflammatory bowel disease (TBD) covers a group of disorders in which the intestines become inflamed (red and swollen), probably as a result of an immune reaction of the body against its own intestinal tissue. Two major types of IBD are described: ulcerative colitis (UC) and Crohn disease (CD). Ulcerative colitis is limited to the colon (large intestine). Crohn disease can involve any part of the gastrointestinal tract from the mouth to the anus, but it most commonly affects the small intestine and/or the colon. Both ulcerative colitis and Crohn disease vary in the intensity and severity during the course of the disease. When there is severe inflammation, the disease is considered to be in an active stage, and the person experiences a flare-up of the condition. When the degree of inflammation is less (or absent), the person usually is without symptoms, and the disease is considered to be in remission. In factor or factors trigger the body's immune system to produce an inflammatory reaction in the intestinal tract that continues without control. As a result of the inflammatory reaction, the intestinal wall is damaged leading to bloody diarrhea and abdominal pain.

It will be appreciated that compounds of the invention may be metabolized to yield biologically active metabolites.

II. Glycosylated Histone Deacetylases Inhibitors

One embodiment provides a compound of Formula I:

Formula I

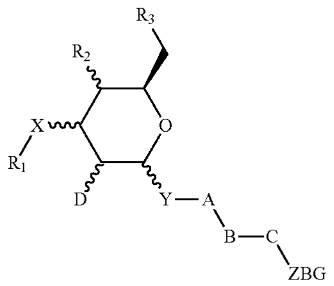

wherein

X is O or $NCH_3$;

$R_1$ is each independently H, $C_{1-6}$ alkyl, $C_{1-6}$ alkanoate, $C_{2-6}$ carbamate, $C_{5-6}$ aryl ester, optionally substituted with heteroatoms;

$R_2$ and $R_3$ are each independently H, OH or $OR_4$;

$R_4$ is each independently $C_{1-6}$ alkyl, $C_{1-6}$ alkanoate, $C_{2-6}$ carbamate, $C_{5-6}$ aryl ester, optionally substituted with heteroatoms;

Y is O, S, $CH_2$ or is absent;

A is each independently substituted or unsubstituted an alkyl, an aryl ring, heteroaryl ring, or is absent;

B is amide, reverse amide, ester, reverse ester, alkoxyl, sulfanyl, sulfinyl, sulfonyl, sulfonamido, ketone, $S_P3$ hybridized carbon, $S_P2$ hybridized carbon, $S_P$ hybridized carbon, 5 or 6 membered substituted or unsubstituted heteroaryl rings, 1,2,3-triazolyl,1,2,4-triazolyl, 1-tetrazolyl, 1-indolyl, 1-indazolyl, 2-isoindolyl, 7-oxo-2-isoimdolyl,1-pirinyl, 3-isothiazolyl, 4-isothiazolyl, 5-isothiazolyl, 1,3,4,-oxadiazole, 4-oxo-2-thiazolinyl, or 5-methyl-1.3,4-thiadiazol-2-yl, thiazoledione, 1,2,3,4-thiatriazole, 1,2,4-dithiazolone, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazolyl, 2-quinolyl. 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, 3-pyrazolyl 4-pyrazolyl, 5-pyrazolyl, 2-oxazolyl, 4-oxazolyl, 4-oxo-2-oxazolyl, 5-oxazolyl, 4,5-dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole. benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol- 3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 1-pyrrolyl, and 1-pyrazolyl;

C is —$CH_2$—, $C_{2-8}$ alkyl, aryl or heteroaryl, optionally substituted with one or more double or triple bonds;

D is each independently H, F, OH, $OCOCH_3$, $NH_2$, $OR_5$, $NHR_5$;

$R_5$ is $C_{1-6}$ alkanoate, $C_{2-6}$ carbamate, $C_{5-6}$ aryl ester optionally substituted with heteroatoms, $C_{5-6}$ fused aryl ester optionally substituted with heteroatoms; and ZBG is hydroxamates, N-formyl hydroxylamine (or retro-hydroxamate), carboxylates, thiols, dithiols, trithiocarbonates, thioesters, benzamide, halo- or heteroaryl-substituted N-(2-amino-phenyl)acylamide, keto, mercaptoacetamides, 2-ketoamides, epoxides, epoxyketones, trifluoromethyl ketones, hydroxypyridinones, pyrones, hydroxylpyridinethiones, and thiopyrones;

or a diastereomer, solvate, or a pharmaceutically acceptable salt thereof.

In one embodiment, $R_1$ is H, $COCH_3$, or $CH_3$.

In another embodiment, $R_2$ and $R_3$ are OH.

In some embodiments, X is O.

In a further embodiment, D is OH or $OCOCH_3$.

In another embodiment, Y is O.

In one embodiment, A is a substituted or unsubstituted aryl ring.

In one embodiment, B is a 5 membered heteroaryl ring.

In some embodiments, B is a 1,2,3-triazole.

In another embodiment, C is five to six —$CH_2$-groups.

In other embodiment, ZBG is hydroxamate.

In one embodiment, ZBG is N-(2-amino-5-fluorophenyl) acylamide.

In another embodiment, ZBG is N-(2-amino-5-(thiophen-2-yl)phenyl)acylamide.

In one embodiment the compound is selected from the group consisting of

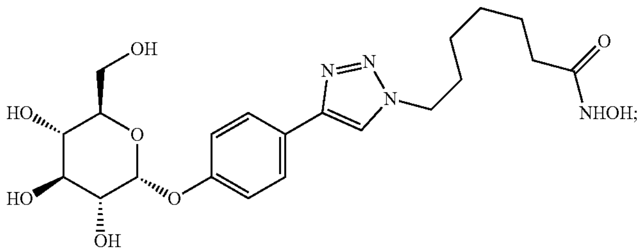

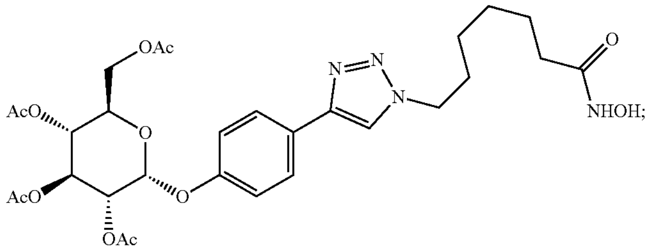

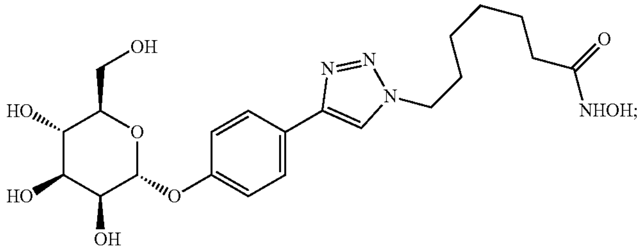

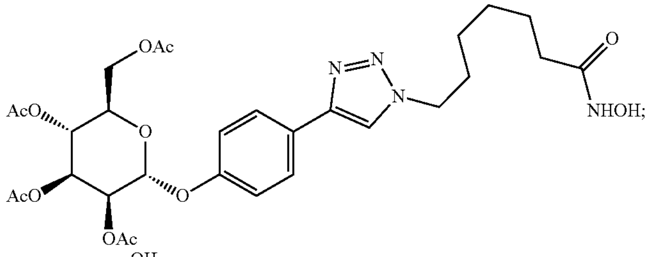

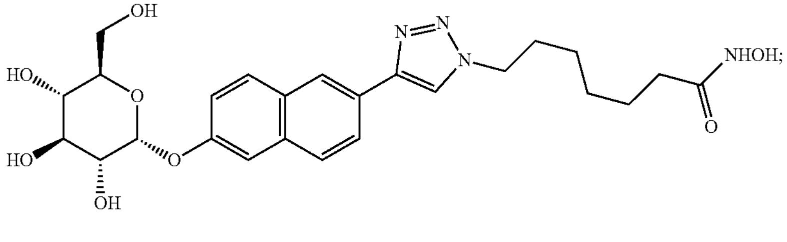

-continued
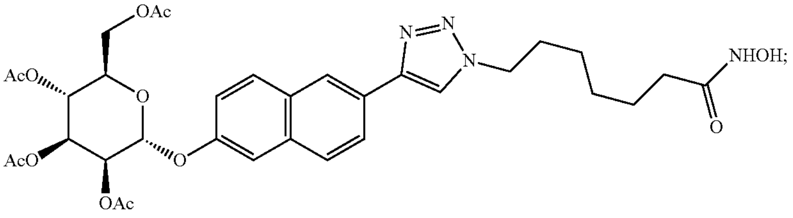
;
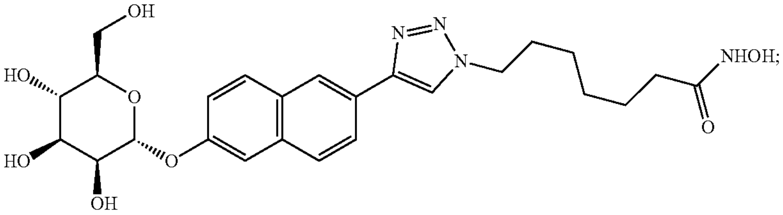
;
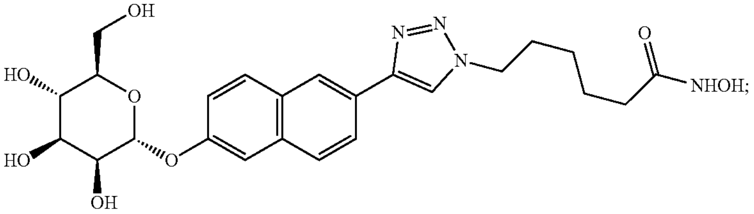
;
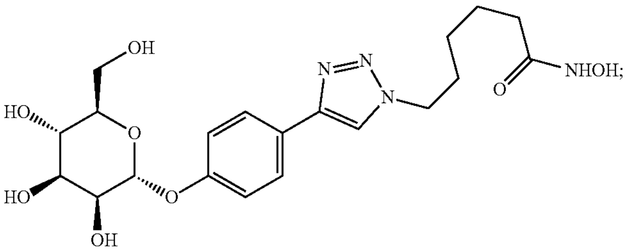
;
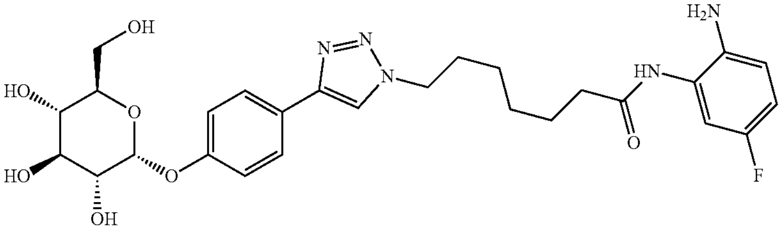
;
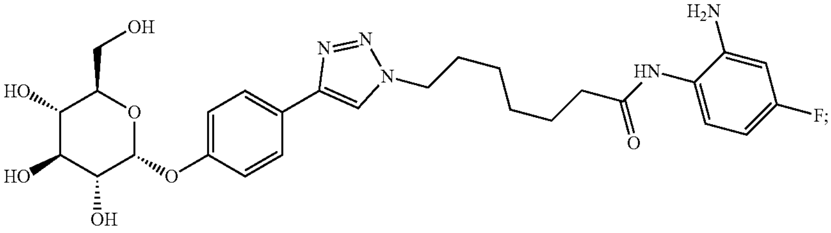
;
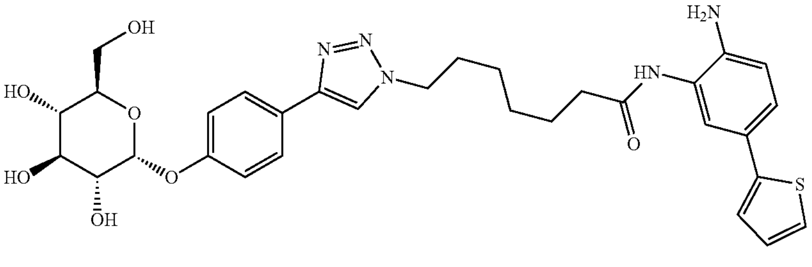
;

-continued

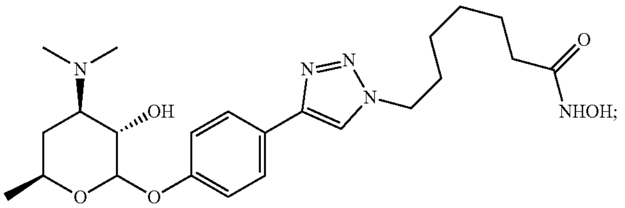

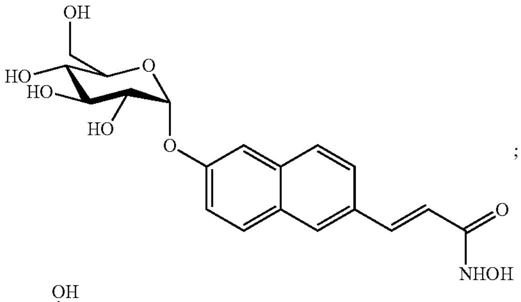

;

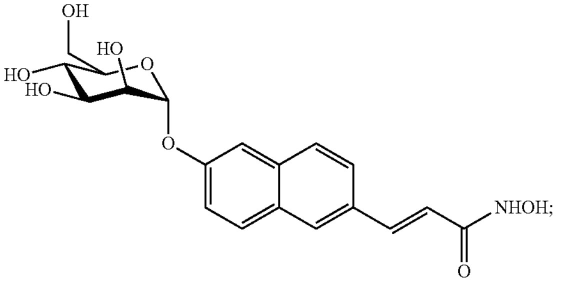

and

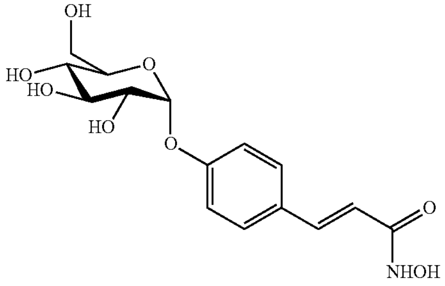

or a diastereomer, solvate, or a pharmaceutically acceptable salt thereof.

III. Pharmaceutical Formulations

The compounds of formula I and mixtures thereof can be formulated into a pharmaceutical composition. Pharmaceutical compositions can be for administration by parenteral (intramuscular, intraperitoneal, intravenous (IV) or subcutaneous injection), enteral, transdermal (either passively or using iontophoresis or electroporation), or transmucosal (nasal, pulmonary, vaginal, rectal, or sublingual) routes of administration or using bioerodible inserts and can be formulated in dosage forms appropriate for each route of administration. The compositions can be administered systemically.

The compounds of formula I can be formulated for immediate release, extended release, or modified release. A delayed release dosage form is one that releases a drug (or drugs) at a time other than promptly after administration. An extended release dosage form is one that allows at least a twofold reduction in dosing frequency as compared to that drug presented as a conventional dosage form (e.g., as a solution or prompt drug-releasing, conventional solid dosage form). A modified release dosage form is one for which the drug release characteristics of time course and/or location are chosen to accomplish therapeutic or convenience objectives not offered by conventional dosage forms such as solutions, ointments, or promptly dissolving dosage forms. Delayed release and extended release dosage forms and their combinations are types of modified release dosage forms.

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes, but is not limited to, diluents, binders, lubricants, disintegrators, fillers, and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", $6^{th}$ Edition, Ansel et. al., (Media, PA: Williams and Wilkins, 1995) which provides information on carriers, materials, equipment and process for preparing tablets and capsules and delayed release dosage forms of tablets, capsules, and granules.

The compounds of formula I can be administered to a subject with or without the aid of a delivery vehicle. Appropriate delivery vehicles for the compounds are known in the art and can be selected to suit the particular active agent. For example, in some embodiments, the active agent(s) is/are incorporated into or encapsulated by, or bound to, a nanoparticle, microparticle, micelle, synthetic lipoprotein particle, or carbon nanotube. For example, the compositions can be incorporated into a vehicle such as polymeric microparticles which provide controlled release of the active agent(s). In some embodiments, release of the drug(s) is controlled by diffusion of the active agent(s) out of the microparticles and/or degradation of the polymeric particles by hydrolysis and/or enzymatic degradation.

Suitable polymers include ethylcellulose and other natural or synthetic cellulose derivatives. Polymers which are slowly soluble and form a gel in an aqueous environment, such as hydroxypropyl methylcellulose or polyethylene oxide, may also be suitable as materials for drug containing microparticles or particles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof. In some embodiments, both agents are incorporated into the same particles and are formulated for release at different times and/or over different time periods. For example, in some embodiments, one of the agents is released entirely from the particles before release of the second agent begins. In other embodiments, release of the first agent begins followed by release of the second agent before the all of the first agent is released. In still other embodiments, both agents are released at the same time over the same period of time or over different periods of time.

A. Formulations for Parenteral Administration

Compounds of formula I and pharmaceutical compositions thereof can be administered in an aqueous solution, by parenteral injection. The formulation may also be in the form of a suspension or emulsion. In general, pharmaceutical compositions are provided including effective amounts of the active agent(s) and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as POLYSORBATE® 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

B. Oral Immediate Release Formulations

Suitable oral dosage forms of the compounds of formula I include tablets, capsules, solutions, suspensions, syrups, and lozenges. Tablets can be made using compression or molding techniques well known in the art. Gelatin or non-gelatin capsules can be prepared as hard or soft capsule shells, which can encapsulate liquid, solid, and semi-solid fill materials, using techniques well known in the art.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydorxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, POLOXAMER® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads granules or particles may also contain minor amount of nontoxic auxiliary substances such as wetting or emulsifying agents, dyes, pH buffering agents, and preservatives.

C. Extended Release Dosage Forms

The extended release formulations of compounds of formula I are generally prepared as diffusion or osmotic systems, for example, as described in "Remington—The science and practice of pharmacy" (20th ed., Lippincott Williams & Wilkins, Baltimore, MD, 2000). A diffusion system typically consists of two types of devices, reservoir and matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but not limited to, methyl acrylate-methyl methacrylate, polyvinyl chloride, and polyethylene. Hydrophilic polymers include, but are not limited to, methylcellulose, hydroxypropylcellulose, hydroxypropylmethylcellulose, sodium carboxymethylcellulose, and carbopol 934, polyethylene oxides. Fatty compounds include, but are not limited to, various waxes such as carnauba wax and glyceryl tristearate.

Alternatively, extended release formulations of the compounds of formula I can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above could be combined in a final dosage form comprising single or multiple units. Examples of multiple units include multilayer tablets, capsules containing tablets, beads, granules, etc.

An immediate release portion can be added to the extended release system by means of either applying an immediate release layer on top of the extended release core using coating or compression process or in a multiple unit system such as a capsule containing extended and immediate release beads.

Extended release tablets containing hydrophilic polymers are prepared by techniques commonly known in the art such as direct compression, wet granulation, or dry granulation processes. Their formulations usually incorporate polymers, diluents, binders, and lubricants as well as the active pharmaceutical ingredient. The usual diluents include inert powdered substances such as any of many different kinds of starch, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidine can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In a congealing method, the drug is mixed with a wax material and either spray-congealed or congealed and screened and processed.

D. Delayed Release Dosage Forms

In some embodiments delayed release formulations of compounds of formula I are created by coating a solid dosage form with a film of a polymer which is insoluble in the acid environment of the stomach, and soluble in the neutral environment of small intestines.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT®. (Rohm Pharma; Westerstadt, Germany), including EUDRAGIT®. L30D-55 and L100-55 (soluble at pH 5.5 and above), EUDRAGIT®. L-100 (soluble at pH 6.0 and above), EUIDRAGIT®. S (soluble at pH 7.0 and above, as a result of a higher degree of esterification), and EUIDRAGITS®. NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

E. Formulations for Mucosal and Pulmonary Administration

The compounds of formula I and compositions thereof can be formulated for pulmonary or mucosal administration. The administration can include delivery of the composition to the lungs, nasal, oral (sublingual, buccal), vaginal, or rectal mucosa. In a particular embodiment, the composition is formulated for and delivered to the subject sublingually.

In one embodiment, the compounds are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

One embodiment provides for nasal delivery for administration of the compounds of invention.

The compounds of formula I can be formulated as an aerosol. The term aerosol refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, CA).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different active agents may be administered to target different regions of the lung in one administration.

F. Topical and Transdermal Formulations

Transdermal formulations containing the compounds of formula I may also be prepared. These will typically be gels, ointments, lotions, sprays, or patches, all of which can be prepared using standard technology. Transdermal formulations can include penetration enhancers.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

"Emollients" are an externally applied agent that softens or soothes skin and are generally known in the art and listed in compendia, such as the "Handbook of Pharmaceutical Excipients", $4^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

The basic difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components.

Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, C12-C15 alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

Additional agents that can be added to the formulation include penetration enhancers. In some embodiments, the penetration enhancer increases the solubility of the drug, improves transdermal delivery of the drug across the skin, in particular across the stratum corneum, or a combination thereof. Some penetration enhancers cause dermal irritation, dermal toxicity and dermal allergies. However, the more commonly used ones include urea, (carbonyldiamide), imidurea, N, N-diethylformamide, N-methyl-2-pyrrolidone, 1-dodecal-azacyclopheptane-2-one, calcium thioglycate, 2-pyrrolidone, N,N-diethyl-m-toluamide, oleic acid and its ester derivatives, such as methyl, ethyl, propyl, isopropyl, butyl, vinyl and glycerylmonooleate, sorbitan esters, such as sorbitan monolaurate and sorbitan monooleate, other fatty acid esters such as isopropyl laurate, isopropyl myristate, isopropyl palmitate, diisopropyl adipate, propylene glycol monolaurate, propylene glycol monooleatea and non-ionic detergents such as BRIJ® 76 (stearyl poly(10 oxyethylene ether), BRIJ® 78 (stearyl poly(20)oxyethylene ether), BRIJ® 96 (oleyl poly(10)oxyethylene ether), and BRIJ® 721 (stearyl poly (21) oxyethylene ether) (ICI Americas Inc. Corp.). Chemical penetrations and methods of increasing transdermal drug delivery are described in Inayat, et al., *Tropical Journal of Pharmaceutical Research,* 8(2):173-179 (2009) and Fox, et al., *Molecules,* 16:10507-10540 (2011). In some embodiments, the penetration enhancer is, or includes, an alcohol such ethanol, or others disclosed herein or known in the art.

Delivery of drugs by the transdermal route has been known for many years. Advantages of a transdermal drug delivery compared to other types of medication delivery such as oral, intravenous, intramuscular, etc., include avoidance of hepatic first pass metabolism, ability to discontinue administration by removal of the system, the ability to control drug delivery for a longer time than the usual gastrointestinal transit of oral dosage form, and the ability to modify the properties of the biological barrier to absorption.

Controlled release transdermal devices rely for their effect on delivery of a known flux of drug to the skin for a prolonged period of time, generally a day, several days, or a week. Two mechanisms are used to regulate the drug flux: either the drug is contained within a drug reservoir, which is separated from the skin of the wearer by a synthetic membrane, through which the drug diffuses; or the drug is held dissolved or suspended in a polymer matrix, through which the drug diffuses to the skin. Devices incorporating a reservoir will deliver a steady drug flux across the membrane as long as excess undissolved drug remains in the reservoir; matrix or monolithic devices are typically characterized by a falling drug flux with time, as the matrix layers closer to the skin are depleted of drug. Usually, reservoir patches include a porous membrane covering the reservoir of medication which can control release, while heat melting thin layers of medication embedded in the polymer matrix (e.g., the adhesive layer), can control release of drug from matrix or monolithic devices. Accordingly, the active agent can be released from a patch in a controlled fashion without necessarily being in a controlled release formulation.

Patches can include a liner which protects the patch during storage and is removed prior to use; drug or drug solution in direct contact with release liner; adhesive which serves to adhere the components of the patch together along with adhering the patch to the skin; one or more membranes, which can separate other layers, control the release of the drug from the reservoir and multi-layer patches, etc., and backing which protects the patch from the outer environment.

Common types of transdermal patches include, but are not limited to, single-layer drug-in-adhesive patches, wherein the adhesive layer contains the drug and serves to adhere the various layers of the patch together, along with the entire system to the skin, but is also responsible for the releasing of the drug; multi-layer drug-in-adhesive, wherein which is similar to a single-layer drug-in-adhesive patch, but contains multiple layers, for example, a layer for immediate release of the drug and another layer for control release of drug from the reservoir; reservoir patches wherein the drug layer is a liquid compartment containing a drug solution or suspension separated by the adhesive layer; matrix patches, wherein a drug layer of a semisolid matrix containing a drug solution or suspension which is surrounded and partially overlaid by the adhesive layer; and vapor patches, wherein an adhesive layer not only serves to adhere the various layers together but also to release vapor. Methods for making transdermal patches are described in U.S. Pat. Nos. 6,461,644, 6,676, 961, 5,985,311, and 5,948,433.

In some embodiments, the composition is formulated for transdermal delivery and administered using a transdermal patch. In some embodiments, the formulation, the patch, or both are designed for extended release of the curcumin conjugate.

Exemplary symptoms, pharmacologic, and physiologic effects are discussed in more detail below.

G. Methods of Manufacture

As will be appreciated by those skilled in the art and as described in the pertinent texts and literature, a number of methods are available for preparing formulations containing the compounds including but not limited to tablets, beads, granules, microparticle, or nanoparticles that provide a variety of drug release profiles. Such methods include, but are not limited to, the following: coating a drug or drug-containing composition with an appropriate coating material, typically although not necessarily incorporating a polymeric material, increasing drug particle size, placing the drug within a matrix, and forming complexes of the drug with a suitable complexing agent.

The delayed release dosage units may be coated with the delayed release polymer coating using conventional techniques, e.g., using a conventional coating pan, an airless spray technique, fluidized bed coating equipment (with or without a Wurster insert). For detailed information concerning materials, equipment and processes for preparing tablets and delayed release dosage forms, see Pharmaceutical Dosage Forms: Tablets, eds. Lieberman et al. (New York: Marcel Dekker, Inc., 1989), and Ansel et al., Pharmaceutical Dosage Forms and Drug Delivery Systems, 6. sup.th Ed. (Media, PA: Williams & Wilkins, 1995).

An exemplary method for preparing extended release tablets includes compressing a drug-containing blend, e.g., blend of drug-containing granules, prepared using a direct blend, wet-granulation, or dry-granulation process. Extended release tablets may also be molded rather than compressed, starting with a moist material containing a suitable water-soluble lubricant. However, tablets are preferably manufactured using compression rather than molding. A preferred method for forming extended release drug-containing blend is to mix drug particles directly with one or more excipients such as diluents (or fillers), binders, disintegrants, lubricants, glidants, and colorants. As an alternative to direct blending, a drug-containing blend may be prepared by using wet-granulation or dry-granulation processes. Beads containing the active agent may also be prepared by any one of a number of conventional techniques, typically starting from a fluid dispersion. For example, a typical method for preparing drug-containing beads involves dispersing or dissolving the active agent in a coating suspension or solution containing pharmaceutical excipients such as polyvinylpyrrolidone, methylcellulose, talc, metallic stearates, silicone dioxide, plasticizers or the like. The admixture is used to coat a bead core such as a sugar sphere (or so-called "non-pareil") having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

IV. Methods of Use

The compounds of formula I and pharmaceutical compositions thereof are useful for the treatment of histone deacetylase dysfunction-driven disease, disorder or condition. In some embodiments, the histone deacetylase dysfunction-driven disease, disorder or condition is cancer or inflammatory diseases. Other embodiments provide methods of inhibiting histone deacetylases by contacting the HDACs in the eels with a compound of formula I or pharmaceutical composition thereof.

In one embodiment the compound for treating cancer or inflammatory disease is selected from the group consisting of

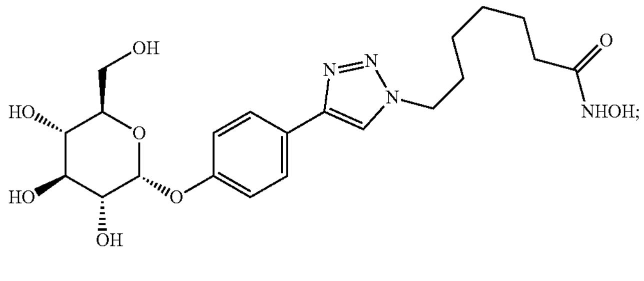
;

-continued
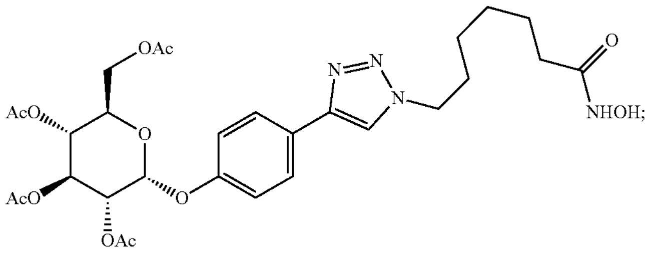
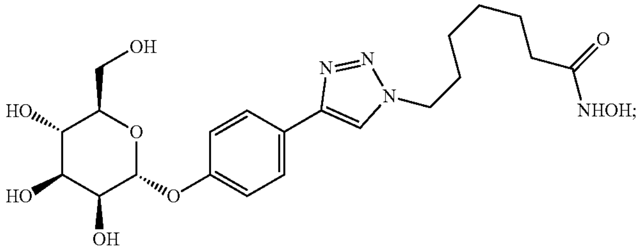
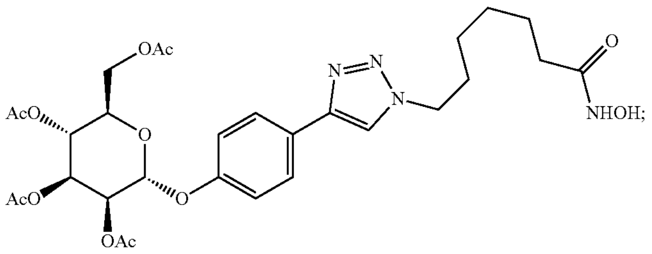
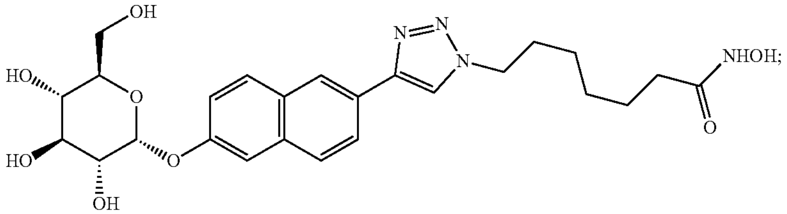
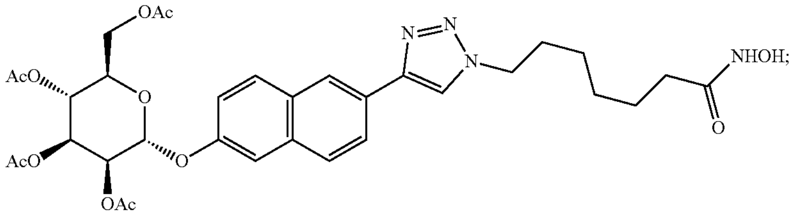
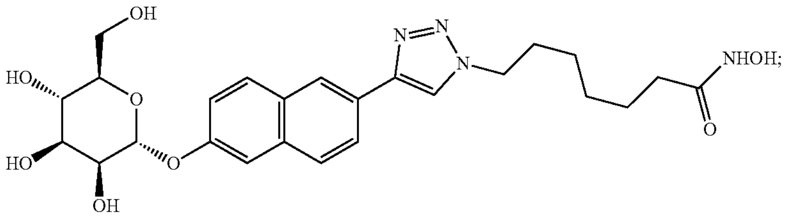
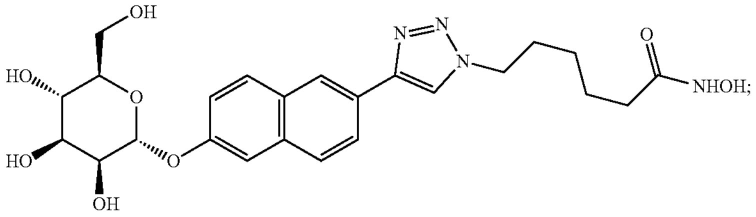

-continued
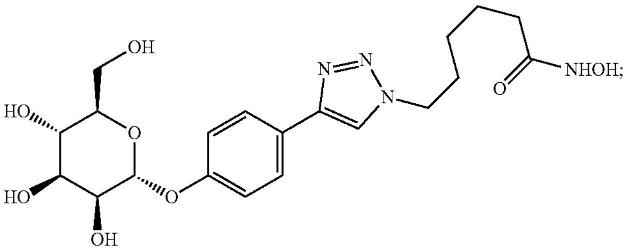
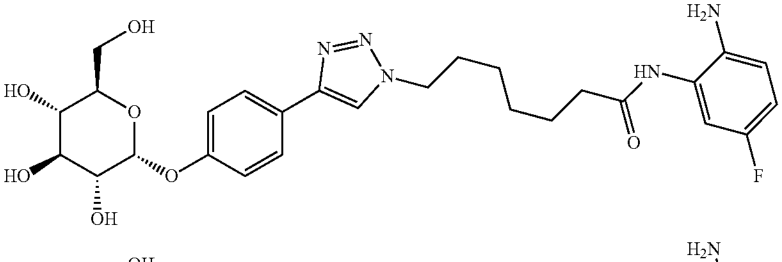
;
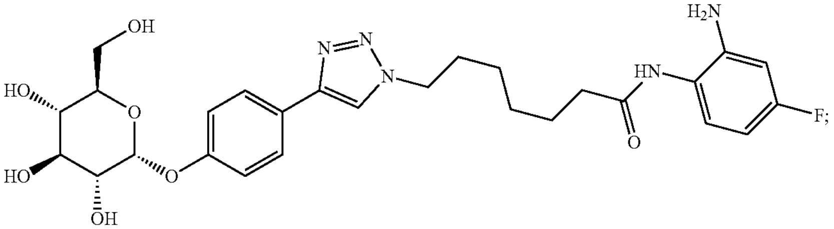
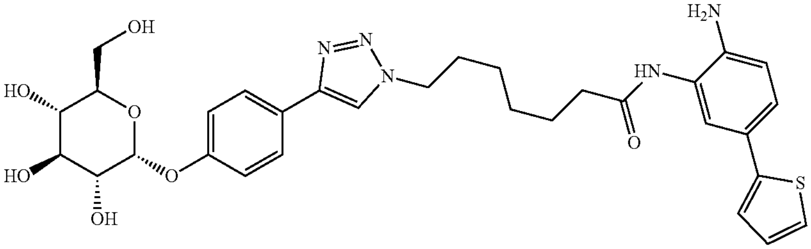
;
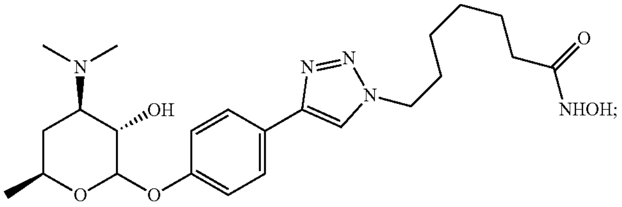
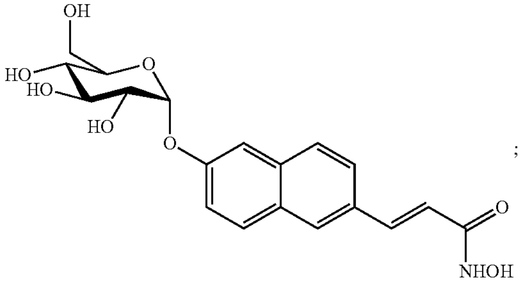
;
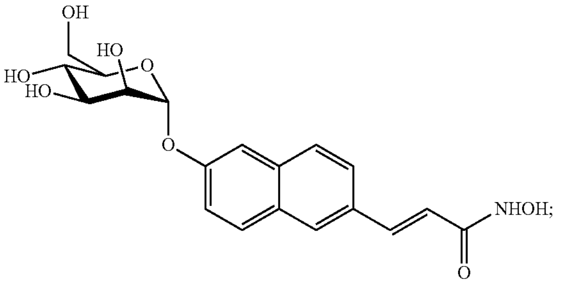
and
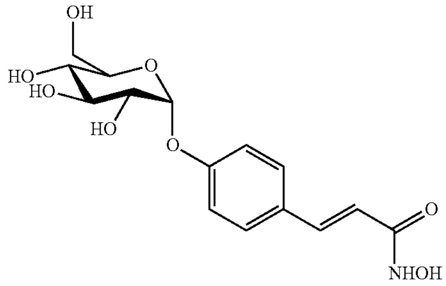

or a diastereomer, solvate, or a pharmaceutically acceptable salt thereof.

A. Cancers

One embodiment provides methods of treating a cancer in a subject in need thereof by administering to the subject a therapeutically effective amount of the compound of formula I or a pharmaceutical composition thereof. In one embodiment the compound is selected from the group consisting of

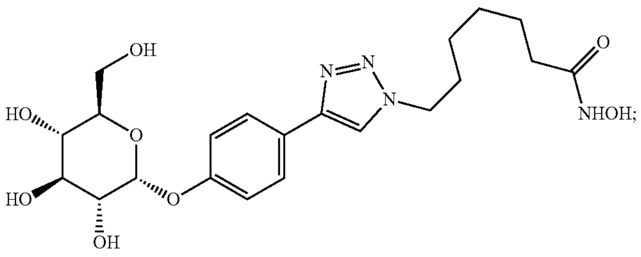

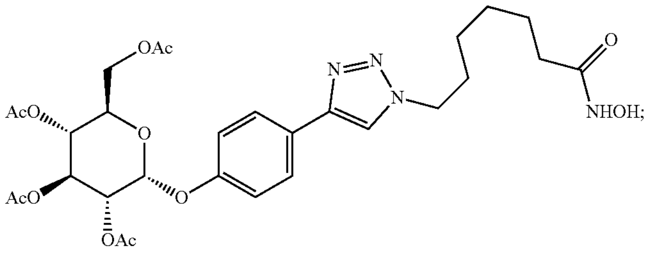

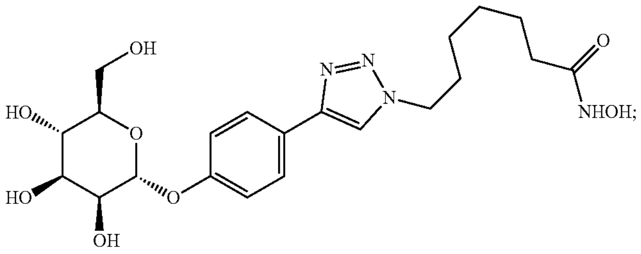

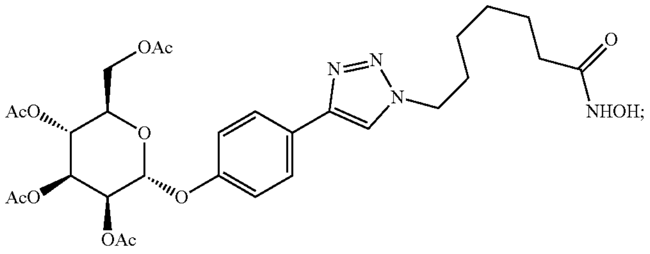

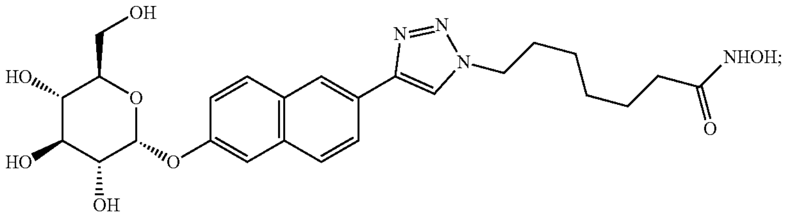

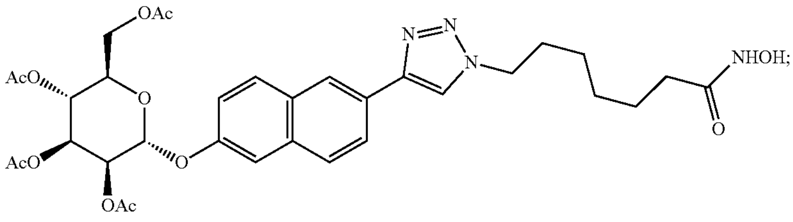

-continued
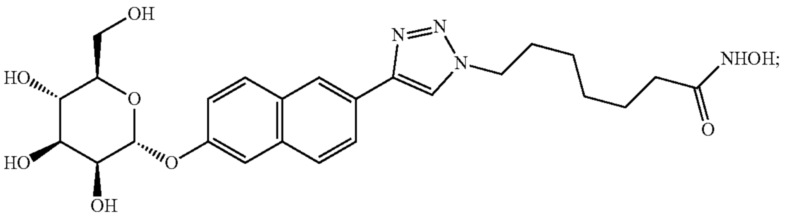
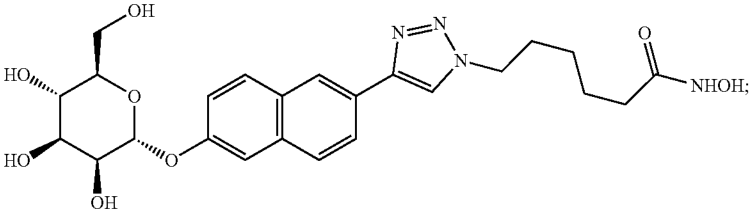
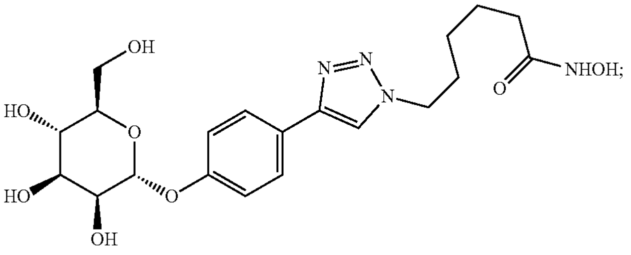
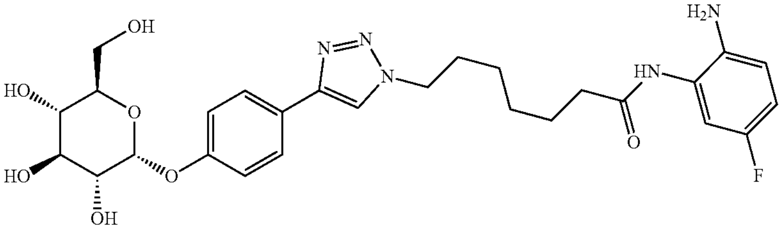
;
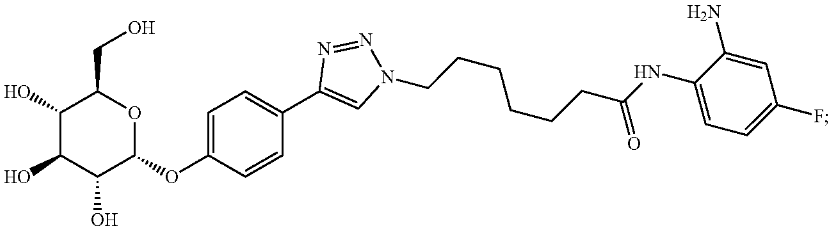
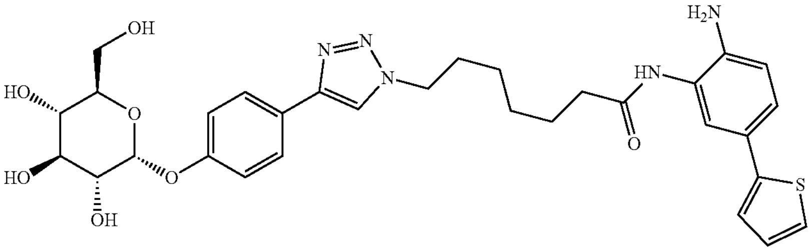
;
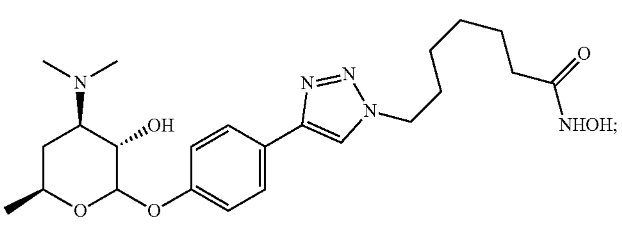
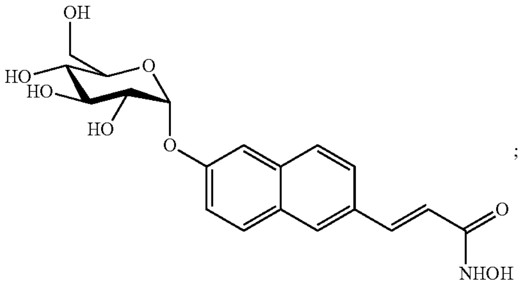
;

-continued

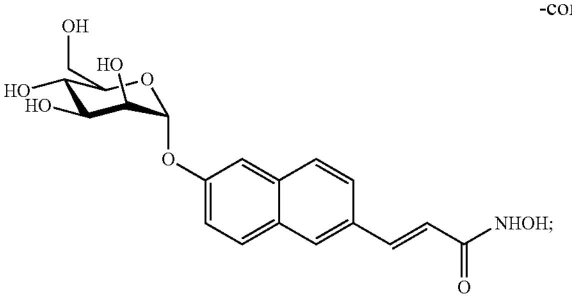

and

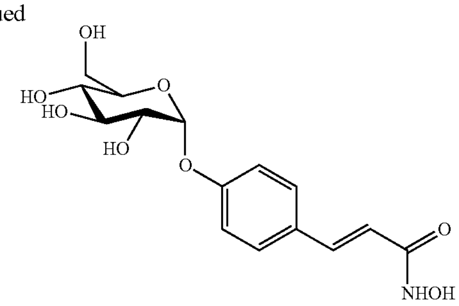

or a diastereomer, solvate, or a pharmaceutically acceptable salt thereof.

Exemplary cancers that can be inhibited or treated by the disclosed compounds of formula I or pharmaceutical composition thereof are liver cancers particularly hepatocellular cancer and colangiocarcinoma. Other representative cancer that can be inhibited or treated by the disclosed compounds of formula I or pharmaceutical composition thereof includes, but are not limited to, squamous cell carcinoma, small-cell lung cancer, non-small cell lung cancer (NSCLC), lung adenocarcinoma, squamous cell lung cancer, and breast cancer.

B. Inflammatory Diseases

Another embodiment provides methods of treating an inflammatory disease, disorder or condition in a subject in need thereof by administering to the subject a therapeutically effective amount of the compound of formula I or a pharmaceutical composition thereof. In one embodiment the compound is selected from the group consisting of

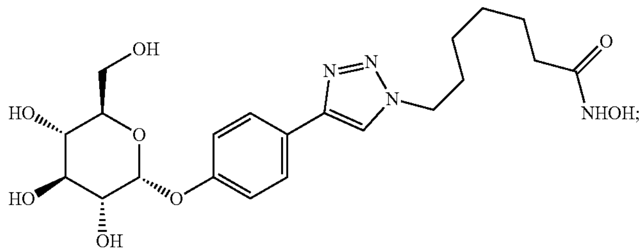

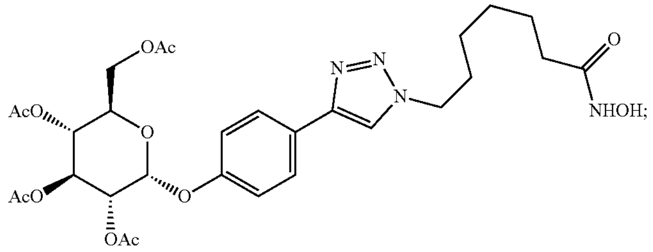

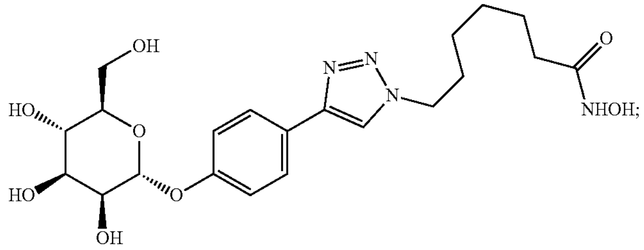

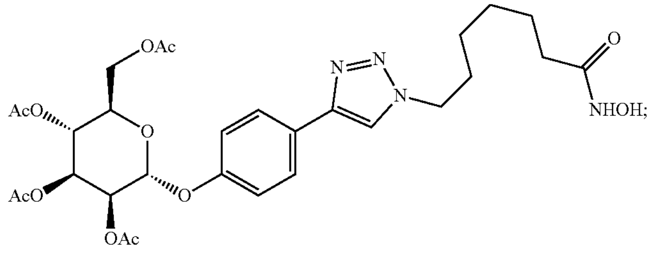

-continued
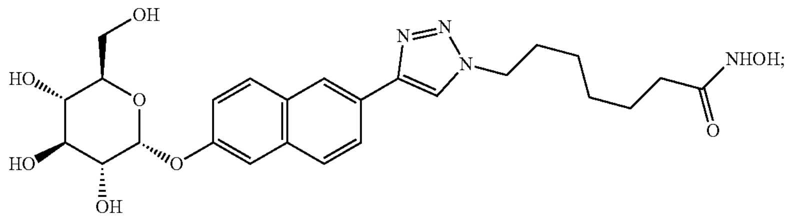
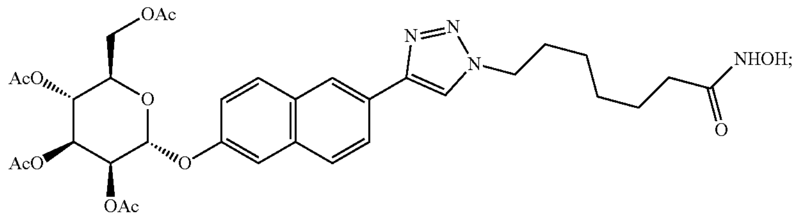
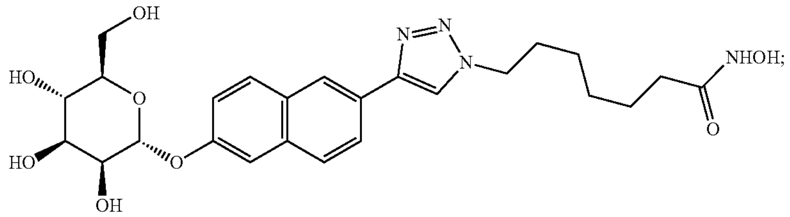
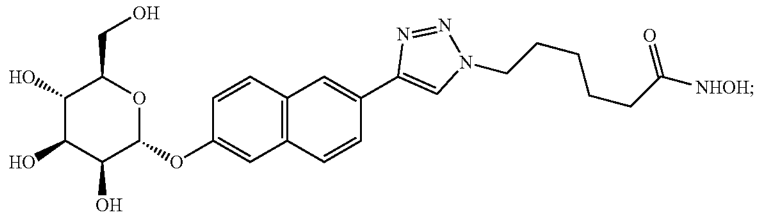
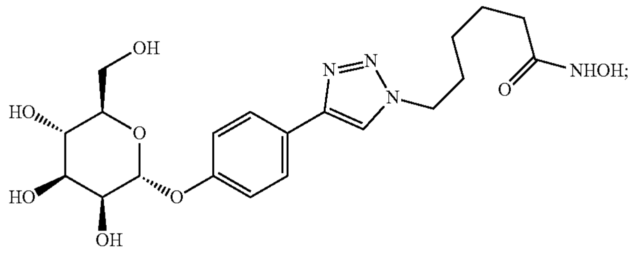
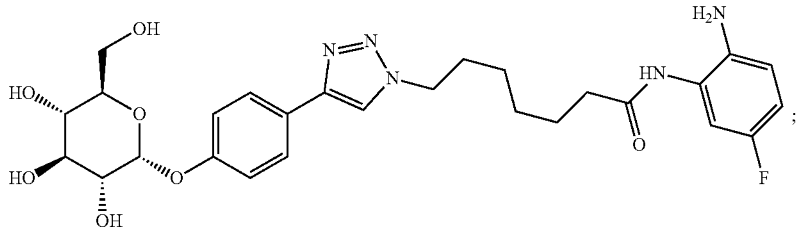
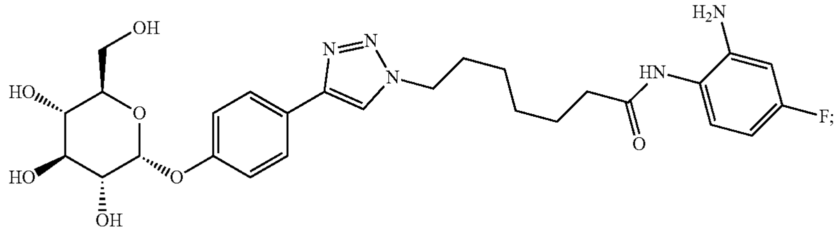

-continued

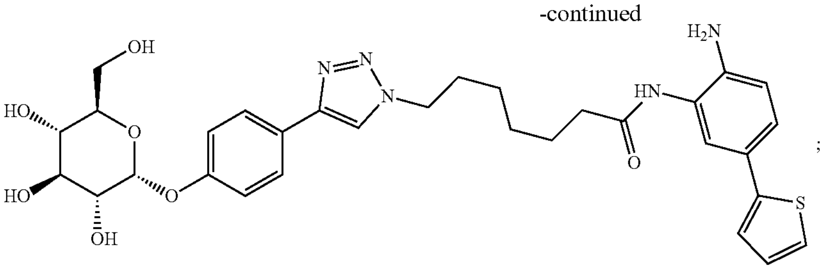

;

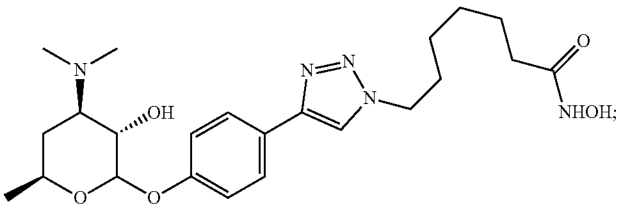

;

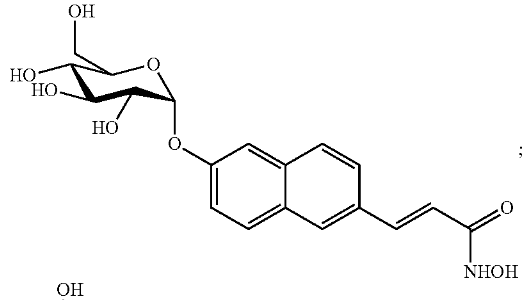

;

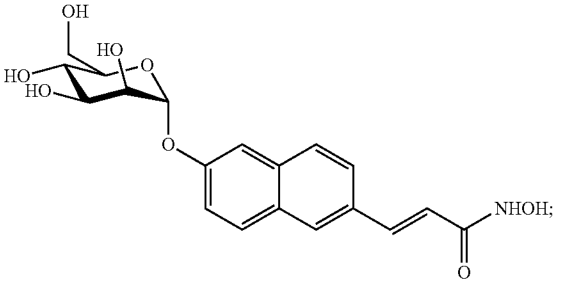

and

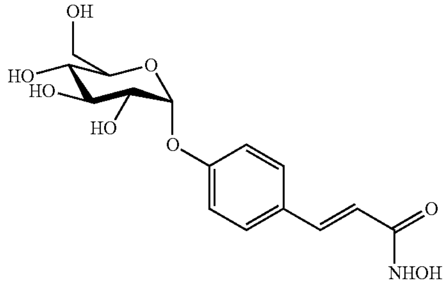

or a diastereomer, solvate, or a pharmaceutically acceptable salt thereof.

Representative inflammatory disease, disorder or condition that can be inhibited or treated by the compound of formula I or pharmaceutical composition thereof includes, but are not limited to, acute and chronic inflammatory disorders, sepsis, acute endotoxemia, encephalitis, Chronic Obstructive Pulmonary Disease (COPD), allergic inflammatory disorders, asthma, pulmonary fibrosis, arthritis, rheumatoid arthritis, osteoarthritis, inflammatory osteolysis, ulcerative colitis, psoriasis, vasculitis, autoimmune disorders, thyroiditis, Meliodosis, (mesenteric) ischernia reperfusion, and in particular inflammatory Bowel Disease (IBD).

EXAMPLES

To provide a better understanding of the foregoing discussion, the following non-limiting examples are provided. Although the examples may be directed to specific embodiments, they are not to be viewed as limiting the invention in any specific respect.

Chemistry:

Synthesis of control compounds STR-V-46, STR-V-48, and STR-V-183

The synthesis of the control compounds STR-V-46, STR-V-48, and STR-V-183 was accomplished via Cu(I) promoted Huisgen cyclization (Rostovtsev, V. V.; Green, L. G.; Fokin, V. V.; Sharpless, K. B.; A stepwise Huisgen cycloaddition process: Copper(I)-catalyzed regioselective "Ligation" of azides and terminal alkynes. *Angew. Chem. Int. Ed.* 2002, 41, 2596-2599; Oyelere, A. K.; Chen, P. C.; Guerrant, W.; Mwakwari, S. C.; Hood, R.; Zhang, Y.; Fan, Y. Non-peptide macrocyclic histone deacetylase inhibitors. *J. Med. Chem.* 2009, 52, 456-468) between appropriate terminal alkynes and azide intermediates (Pirali, T.; Pagliai, F.; Mercurio, C.; Boggio, R.; Canonico, P. L.; Sorba, G.; Tron, G. C.; Genazzani, A. A., Triazole-Modified Histone Deacetylase Inhibitors As a Rapid Route to Drug Discovery. *J. Comb. Chem.* 2008, 10, 624-627; Wang, F.; Zhang, Y.; Liu, Z.; Du, Z.; Zhang, L.; Ren, J.; Qu, X., A Biocompatible Heterogeneous MOF—Cu Catalyst for In Vivo Drug Synthesis in Targeted Subcellular Organelles. *Angew. Chem. Int. Ed.* 2019, 58, 6987-6992; Pirali, T.; Gatti, S.; Di Brisco, R.; Tacchi, S.; Zaninetti, R.; Brunelli, E.; Massarotti, A.; Sorba, G.; Canonico, P. L.; Moro, L., Estrogenic analogues synthesized by click chemistry. *ChemMedChem* 2007, 2, 437-440), followed by functional group deprotection adapting our published protocol (Scheme 1) (Chen, P. C.; Patil, V.; Guerrant, W.; Green, P.; Oyelere, A. K., Synthesis and structure—activity relationship of histone deacetylase (HDAC) inhibitors with triazole-linked cap group. Bioorg. Med. Chem. 2008, 16, 4839-4853).

Scheme 1. Synthesis of control compounds STR-V-46, STR-V-48, and STR-V-183.

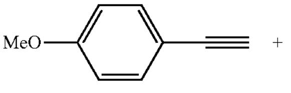

1-ethynyl-4-methoxybenzene

-continued

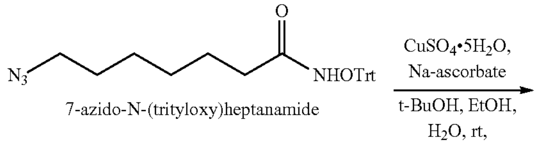

7-azido-N-(trityloxy)heptanamide

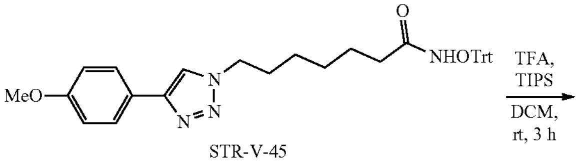

STR-V-45

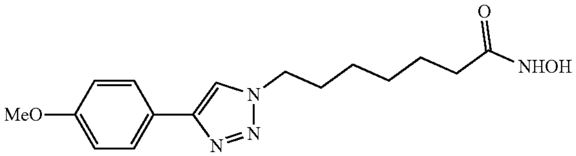

STR-V-46

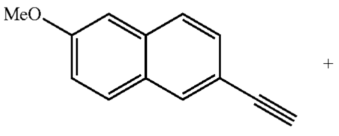

2-ethynyl-6-methoxynaphthalene

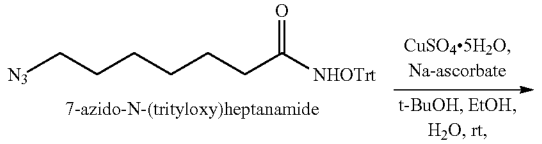

7-azido-N-(trityloxy)heptanamide

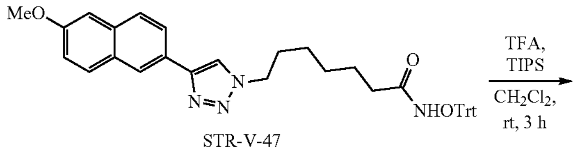

STR-V-47

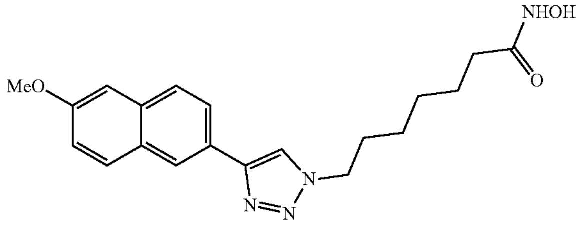

STR-V-48

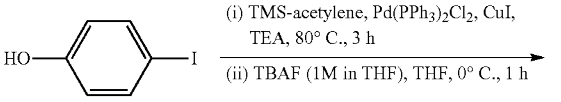

4-iodophenol

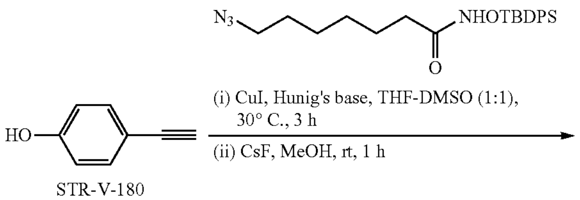

STR-V-180

-continued

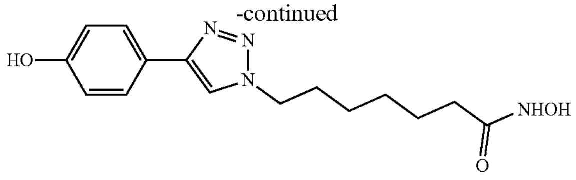

STR-V-183

Toward the phenyl-glucosylated hydroxamates, glucose penta-acetate was coupled with the 4-iodophenol in the presence of Lewis acid Tin (IV) chloride in chloroform to yield STR-V-49 (Otsuka, I.; Hongo, T.; Nakade, H.; Narumi, A.; Sakai, R.; Satoh, T.; Kaga, H.; Kakuchi, T., Chiroptical and lectin recognition properties of glycoconjugated poly (phenylacetylene) s featuring variable saccharide functionalities. *Macromolecules* 2007, 40, 8930-8937). The Bis (triphenylphosphine)palladium(II) dichloride ($PdCl_2(PPh_3)_2$) mediated coupling (Sonogashira coupling) of STR-V-49 with ethynyltrimethylsilane (TMS-acetylene) followed by TMS group removal by treatment TBAF furnished STR-V-51 (Otsuka, I.; Hongo, T.; Nakade, H.; Narumi, A.; Sakai, R.; Satoh, T.; Kaga, H.; Kakuchi, T., Chiroptical and lectin recognition properties of glycoconjugated poly (phenylacetylene)s featuring variable saccharide functionalities. *Macromolecules* 2007, 40, 8930-8937) which was clicked with 7-azido-N-((tert-butyldiphenylsilyl)oxy)heptanamide (STR-V-107) (Cu(I) promoted Huisgen cyclization) and the resulting protected product treated with cesium fluoride to yield STR-V-167. The acetyl groups of STR-V-167 was hydrolyzed by treatment with to sodium methoxide in methanol to furnish the target class I compounds STR-V-53 (Scheme 2).

To synthesize the naphthyl-glucosylated hydroxamate, 6-bromonaphthalen-2-ol was coupled to the glucose penta-acetate using Lewis acid boron trifluoride etherate in dichloromethane (DCM) under refluxing condition to form STR-V-55 (Capicciotti, C. J.; Mancini, R. S.; Turner, T. R.; Koyama, T.; Alteen, M. G.; Doshi, M.; Inada, T.; Acker, J. P.; Ben, R. N., O-aryl-glycoside ice recrystallization inhibitors as novel cryoprotectants: a structure—function study. *ACS Omega* 2016, 1, 656-662). Sonogashira coupling of the bromo naphthalene STR-V-55 and TMS-acetylene using catalysts copper iodide, $PdCl_2(PPh_3)_2$, TPP in THF, followed by deprotection of the TMS moiety of the resulting product using TBAF, resulted in STR-V-111. Subsequently, STR-V-111 was clicked with 7-azido-N-((tert-butyldiphenylsilyl)oxy)heptanamide (STR-V-107), followed by cesium fluoride deprotection and acetyl group removal; furnished target compound STR-V-114 (Scheme 2). Compounds STR-V-155, STR-V-157 and STR-V-159, which have HDAC class I selective zinc binding group (Moradei, O. M.; Mallais, T. C.; Frechette, S.; Paquin, I.; Tessier, P. E.; Leit, S. M.; Fournel, M.; Bonfils, C.; Trachy-Bourget, M.-C.; Liu, J.; Yan, T. P.; Lu, A.-H.; Rahil, J.; Wang, J.; Lefebvre, S.; Li, Z.; Vaisburg, A. F.; Besterman, J. M., Novel Aminophenyl Benzamide-Type Histone Deacetylase Inhibitors with Enhanced Potency and Selectivity. *J. Med. Chem.* 2007, 50, 5543-5546), were synthesized using a variant of the Cu(I) promoted Huisgen cyclization (Scheme 2) (Liang, L.; Astruc, D., The copper (I)-catalyzed alkyne-azide cycloaddition (CuAAC) "click" reaction and its applications. An overview. *Coord. Chem. Rev.* 2011, 255, 2933-2945).

Scheme 2. Synthesis of the glucosylated HDACi.
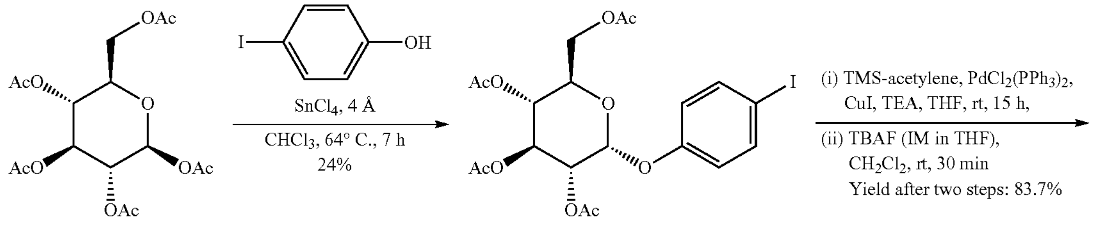
Glucose peantaacetate
STR-V-49
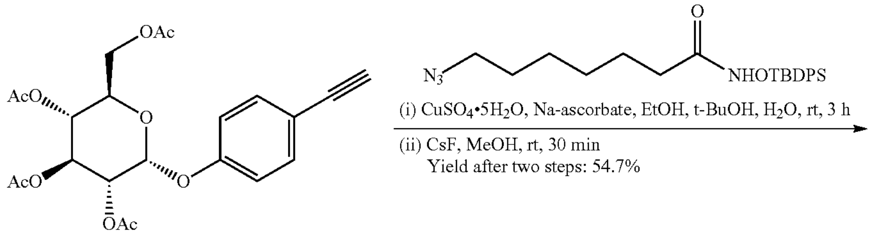
STR-V-51
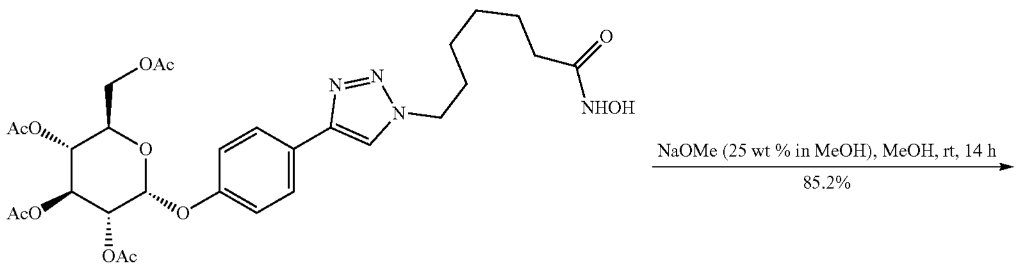
STR-V-167
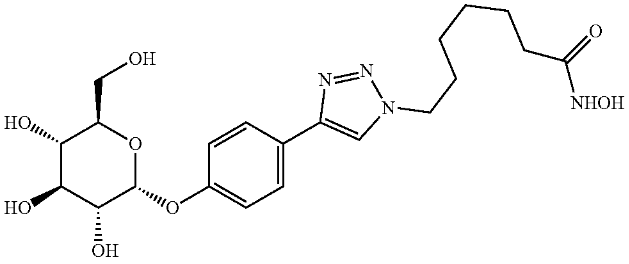
STR-V-53
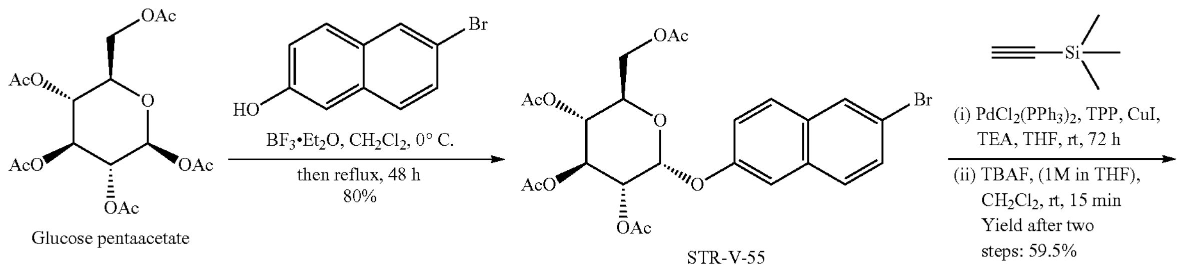
Glucose pentaacetate
STR-V-55
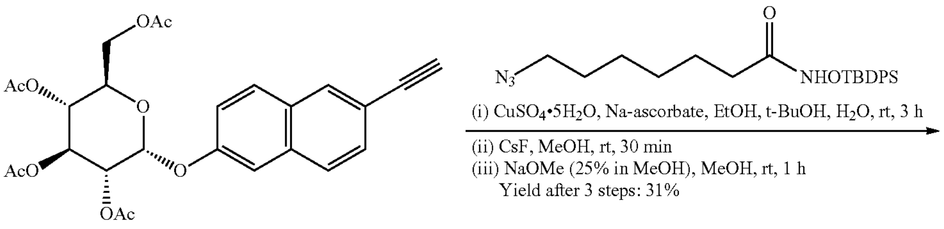
STR-V-111

-continued

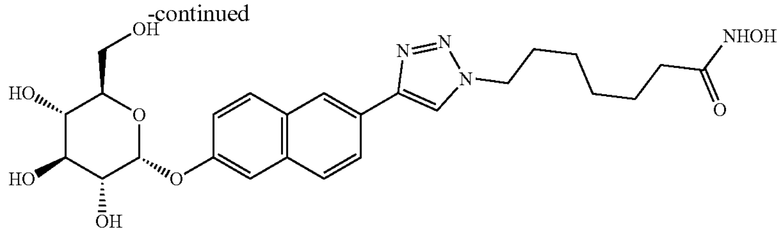

STR-V-114

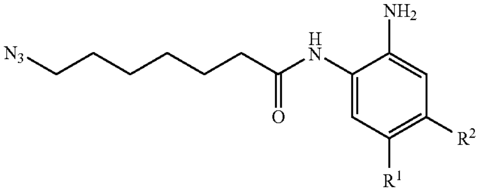

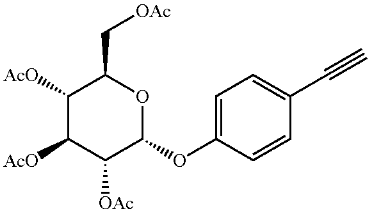

STR-V-51

$R^1$ = F; $R^2$ = H $R^1$ = H; $R^2$ = F (i) CuI, Hunig's base, THF-DMSO (1:1), rt, overnight (ii) NaOMe (25 wt % in MeOH), MeOH, rt, 1 h

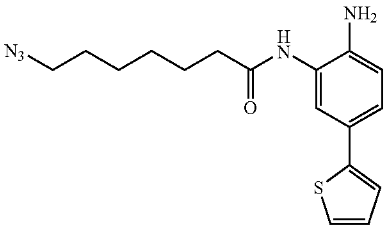

SBI-I-79

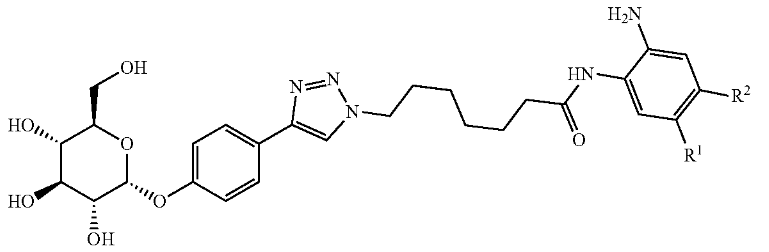

STR-V-155 ($R^1$ = F; $R^2$ = H)

STR-V-157 ($R^1$ = H; $R^2$ = F)

(i) CuI, Hunig's base, THF-DMSO (1:1), rt, overnight (ii) NaOMe (25 wt % in MeOH), MeOH, rt, overnight

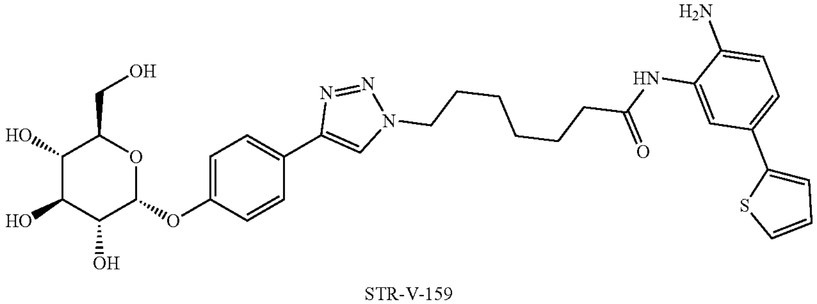

STR-V-159

To synthesize the mannose derivatives, mannose penta-acetate was coupled with 4-iodophenol using boron trifluoride etherate in DCM. The product STR-I-189 was coupled with TMS-acetylene using the same condition for the synthesis of STR-V-51 and the resulting acetylated compound STR-I-190 was clicked with 7-azido-N-((tert-butyldiphenylsilyl)oxy)heptanamide using the same condition as in the synthesis of STR-V-167 to furnish STR-V-176. Subsequent hydrolysis of the acetyl groups yielded the mannose compound STR-I-195. Mannosylated phenyl (STR-II-29) and naphthyl (STR-II-35) compounds are similarly synthesized from 6-azido-N-((tert-butyldiphenylsilyl)oxy)hexanamide and STR-I-190 and STR-II-34, respectively (Scheme 3).

In order to synthesize the naphthyl-mannosylated hydroxamate, the coupling of mannose penta-acetate with 6-bromonaphthalen-2-ol using boron trifluoride etherate, under the same condition used for the synthesis of STR-V-55, furnished STR-II-30 which was converted to the monnosylated alkyne STR-II-34. The transformation of STR-II-34 to the target mannosylated compounds STR-V-177 and STR-II-36 (Scheme 3), followed similar reaction steps used to synthesize analogous glucose compounds (Scheme 2).

Scheme 3. Synthesis of mannosylated HDACi
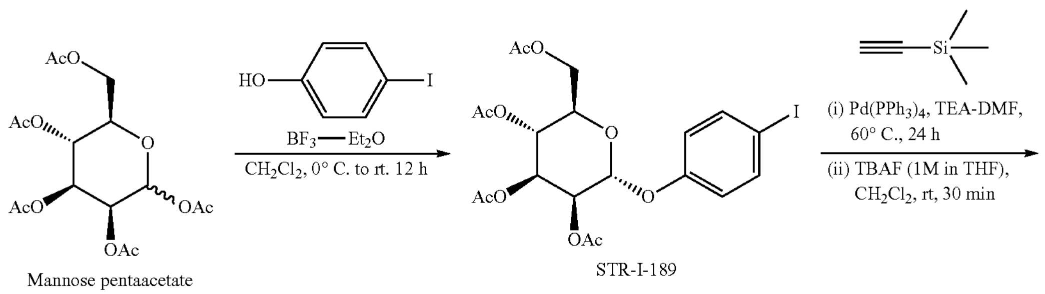
Mannose pentaacetate
STR-I-189
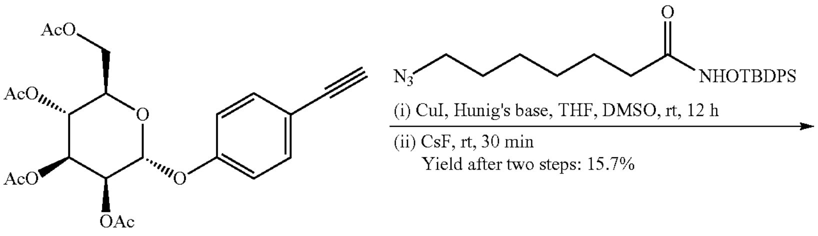
STR-I-190
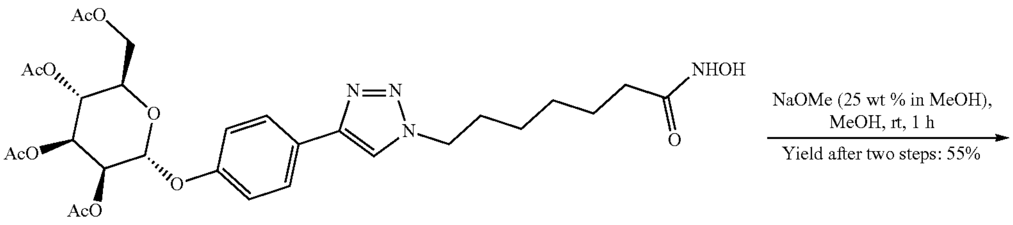
STR-V-176
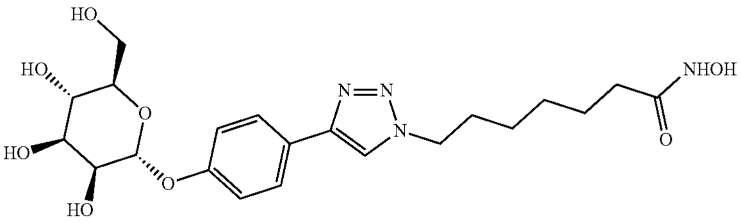
STR-I-195
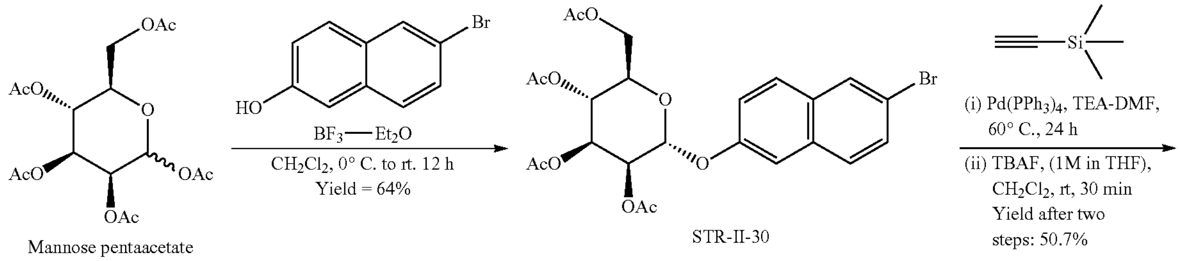
Mannose pentaacetate
STR-II-30
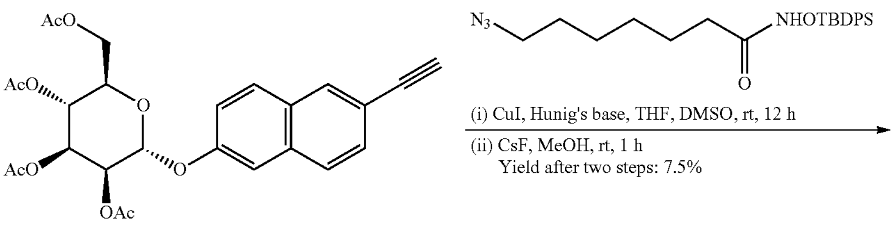
STR-II-34

-continued

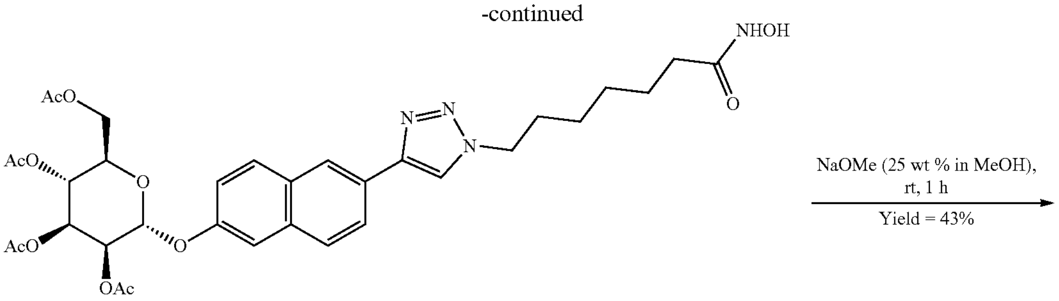

STR-V-177

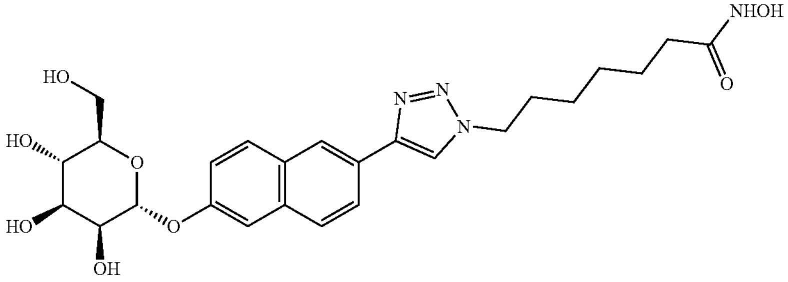

STR-II-36

Toward the acryloyl-mannosylated hydroxamate, Heck coupling of mannose derivative STR-II-30 with N-(trityloxy)acrylamide followed by the deprotection of the O-trityl group with TFA/TIPS in DCM and the acetyl group with sodium methoxide furnished STR-V-105. The glucosylated compound STR-V-115 was similarly made from STR-V-55 and N-(trityloxy)acrylamide (Scheme 4).

Scheme 4. Synthesis of glycosylated or mannosylated hydroxamate HDACi.

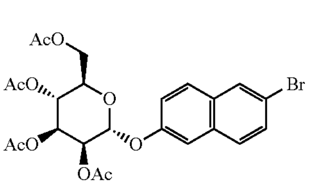

STR-II-30 (Mannose)

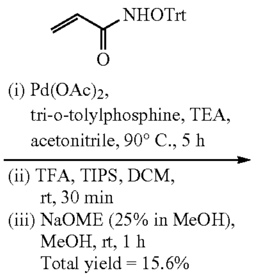

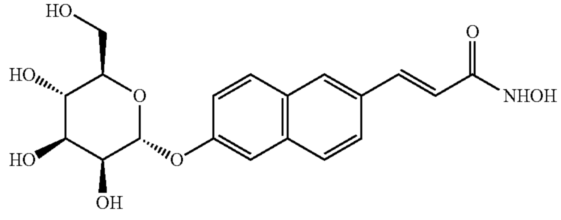

STR-V-105

-continued

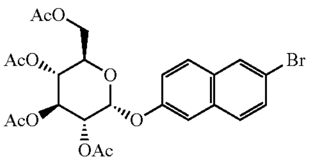

STR-V-55 (Glucose)

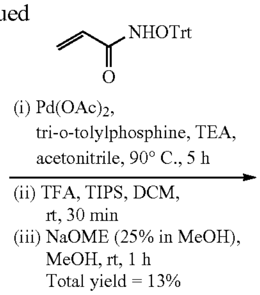

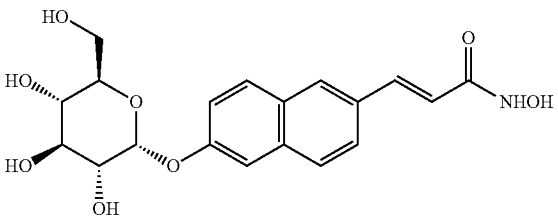

STR-V-115

The desosaminylated compounds were synthesized from diacetyl desosamine STR-V-160 which was synthesized via acetylation of desosamine (Scheme 5). The coupling of STR-V-160 with 4-iodophenol, using the same method described for the synthesis of STR-I-189, resulted in STR-V-161, which was converted to STR-V-163 using the same condition as in the synthesis of STR-V-51. Subsequently, STR-V-163 was clicked with 7-azido-N-((tert-butyldiphenylsilyl)oxy)-heptanamide (STR-V-107); and the deprotection of the TBDPS and acetyl groups, in analogous manner to the synthesis of STR-V-53, furnished STR-V-165 (Scheme 5).

Scheme 5. Synthesis of desosaminylated hydroxamate HDACi.

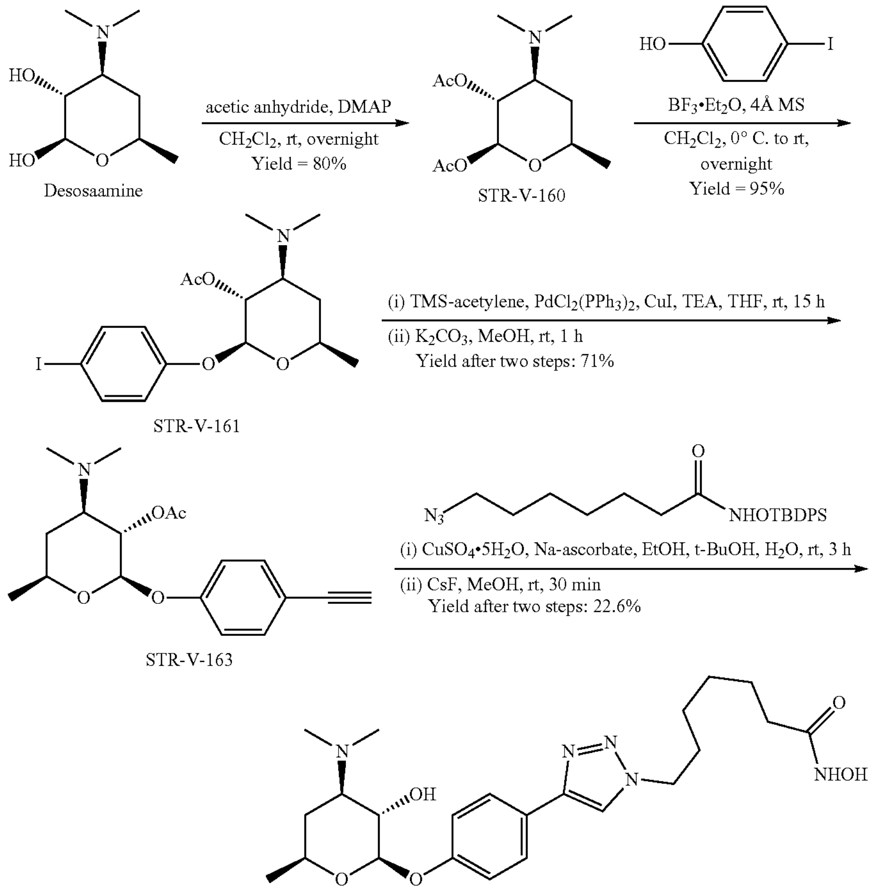

Desosaamine

STR-V-160

STR-V-161

STR-V-163

STR-V-165

Materials

STR-V-46 (N-hydroxy-7-[4-(4-methoxyphenyl)triazol-1-yl]heptanamide) and STR-V-48 (N-hydroxy-7-(4-(6-methoxynaphthalen-2-yl)-1H-1,2,3-triazol-1-yl)heptanamide) have been synthesized before (Chen et al. *Bioorg. Med. Chem.* 2008, 16, 4839-4853). STR-I-190 (CAS: 677352-87-3), is a previously known compound. STR-V-51 (Pubchem: 102084446), and (2R,3R,4 S,5 S,6R)-2-(acetoxymethyl)-6-(4-iodophenoxy)tetrahydro-2H-pyran-3,4,5-triyl triacetate (STR-V-49) were reported (Otsuka, I.; Hongo, T.; Nakade, H.; Narumi, A.; Sakai, R.; Satoh, T.; Kaga, H.; Kakuchi, T., Chiroptical and lectin recognition properties of glycoconjugated poly (phenylacetylene) s featuring variable saccharide functionalities. *Macromolecules* 2007, 40, 8930-8937). Azido linkers: N-(2-amino-4-fluorophenyl)-7-azidoheptanamide, N-(2-amino-5-fluorophenyl)-7-azidoheptanamide, and N-(2-amino-5-(thiophen-2-yl)phenyl)-7-azidoheptanamide were made in published work (Tapadar, S.; Fathi, S.; Wu, B.; Sun, C. Q.; Raji, I.; Moore, S. G.; Arnold, R. S.; Gaul, D. A.; Petros, J. A.; Oyelere, A. K., Liver-targeting class I selective histone deacetylase inhibitors potently suppress hepatocellular tumor growth as standalone agents. *Cancers* 2020, 12, 3095). N-(trityloxy) acrylamide was synthesized by condensation of acrylic acid with O-tritylhydroxylamine (CAS: 31938-11-1).

Chemical Synthesis

Synthesis of 4-ethynylphenol (STR-V-180)

4-iodophenol (1.09 g, 4.95 mmol) was mixed with Bis (triphenylphosphine)palladium(II) dichloride (104 mg, 0.15 mmol) and copper (I) iodide (29 mg, 0.15 mmol) along with TMS-acetylene (1.01 mL, 7.18 mmol) in triethylamine (15 mL). The solution was purged with argon for 5-10 minutes. Then the reaction was heated to 80° C. for 3 h and then cooled to room temp. The mixture was filtered on a celite bed and the filtrate was evaporated to dryness in vacuo. The residue was purified by column chromatography eluting with EtOAc:hexane 3:7. The fractions containing the product were pooled and dried in vacuo to furnish yellow solid. The product was dissolved into ice cold THF and mixed with 6 mL of TBAF (1M in THF) in ice bath (Pirali, T.; Gatti, S.; Di Brisco, R.; Tacchi, S.; Zaninetti, R.; Brunelli, E.; Massarotti, A.; Sorba, G.; Canonico, P. L.; Moro, L., Estrogenic analogues synthesized by click chemistry. *ChemMedChem* 2007, 2, 437-440). The reaction lasted for 1 h and the crude was purified by column chromatography eluting with EtOAc:hexane 1:9. The fractions containing the product were pooled and dried in vacuo to furnish STR-V-180 as a brown oil.

Synthesis of N-hydroxy-7-(4-(4-hydroxyphenyl)-11-1-1,2,3-triazol-1-yl)heptanamide (STR-V-183)

STR-V-180 (47 mg, 0.4 mmol) was mixed with STR-V-107 (167 mg, 0.4 mmol) and copper (I) iodide (38 mg, 0.2 mmol) in THF:DMSO (1:1 mL) solution. The solution was purged with Argon for 5-10 minutes before Hunig's base (0.2 mL, 10 v/v %) was added. The reaction ran at room temperature for 1 h and was quenched by adding ammonia hydroxide (1M, 1 mL). The reaction was partitioned between DCM (50 mL) and 1M $NH_4OH$ (30 mL) and the two layers separated. The organic layer was washed with water (30 mL), dried over $Na_2SO_4$ and evaporated off to give a crude product. The product was dissolved into methanol (4 mL) with addition of cesium fluoride (122 mg, 0.8 mmol) to remove the TBDPS protection group. The desired product STR-V-183 was obtained by purification using preparative TLC, eluting with 5% MeOH in DCM. The STR-V-183 was obtained as brick-red solid (4.5 mg, 3.8%). $^1H$ NMR (700 MHz, $CD_3OD$) δ 8.08 (s, 1H), 7.54 (d, J=8.5 Hz, 2H), 6.75 (d, J=8.6 Hz, 2H), 4.33 (t, J=7.1 Hz, 2H), 1.99 (t, J=7.4 Hz, 2H), 1.86 (p, J=7.1 Hz, 2H), 1.53 (p, J=7.3 Hz, 2H), 1.34-1.24 (m, 2H), 1.20 (d, J=4.8 Hz, 4H). $^{13}C$ NMR (176 MHz, MeOD) δ 157.6, 147.7, 126.7, 119.7, 115.3, 76.8, 49.9, 32.2, 29.7, 28.0, 25.7, 25.1, 13.0.

Synthesis of (2R,3R,4S,5R,6R)-2-(acetoxymethyl)-6-(4-(1-(7-(((tert-butyldiphenylsilyl)oxy)-amino)-7-oxoheptyl)-1H-1,2,3-triazol-4-yl)phenoxy)tetra-hydro-2H-pyran-3,4,5-triyl triacetate (STR-V-167)

STR-V-51 (1 g, 2.2 mmol) was mixed with STR-V-107 (0.88 g, 2.07 mmol) in ethanol and tert-butanol (6:6 mL). Copper (II) sulfate (99 mg, 0.40 mmol), sodium ascorbate (313 mg. 1.58 mmol), 0.5 mL water were added to the mixture. The reaction was stirred room temperature for 3 h. The crude was partitioned between DCM (30 mL) and water (50 mL) and two layers separated. The organic layer was washed with water (30 mL), dried over $Na_2SO_4$ and evaporated in vacuo to give the crude product. The product was purified column chromatography, eluting with EtOAc: hexane 8:2 to furnish the TDBPS protected intermediate (1.1 g, 84%). Then, the intermediate (1.10 g, 1.27 mmol) was dissolved into methanol and deprotected using cesium fluoride (330 mg, 2.2 mmol) at room temperature for 30 minutes to furnish STR-V-167 as brown solid (730 mg, 66% after the second step reaction).

Synthesis of N-hydroxy-7-(4-(4-0(2R,3R,4S,5S,6R)-3,4,5-trihydroxy-6-(hydroxymethyl)-tetrahydro-211-pyran-2-yl)oxy)phenyl)-111-1,2,3-triazol-1-yl)hep-tanamide (STR-V-53)

STR-V-167 (730 mg, 1.15 mmol) was stirred in MeOH (2 mL) and sodium methoxide (0.5 mL, 2.3 mmol) for 14 h. Subsequently, the reaction was treated with Amberlite IR120 Plus resin to adjust the pH=1. Noticed that some precipitates may crush out when methoxide was added if the reaction was in larger scale (>500 mg), while the addition of Resin could rapidly eliminate the precipitation. The resin was filtered, and the filtrate was collected and evaporated to dryness via vacuum to furnish the crude STR-V-53. To purify, the crude STR-V-53 was dissolved in water (5 mL) and wash with 15% MeOH in DCM. The aqueous layer was collected and evaporated to dryness. To completely dry the product, 1 mL acetonitrile and 0.1 mL water were and dried by lyophilization to furnish STR-V-53 as white solid (yield=460 mg, 85%). $^1H$ NMR (700 MHz, DMSO-d6) δ 10.33 (s, 1H), 8.48 (s, 1H), 7.76 (d, J=8.6 Hz, 2H), 7.16 (d, J=8.7 Hz, 2H), 5.76 (s, 0H), 5.42 (d, J=3.5 Hz, 1H), 4.36 (t, J=7.1 Hz, 2H), 3.63 (t, J=9.2 Hz, 1H), 3.57 (m, 3.59-3.55, 4.2 Hz, 1H), 3.47 (m, 3.49-3.42, 2H), 3.38 (dd, J=9.7, 3.5 Hz, 1H), 3.20 (t, J=9.2 Hz, 1H), 1.93 (t, J=7.4 Hz, 2H), 1.85 (p, J=7.1 Hz, 2H), 1.48 (p, J=7.3 Hz, 2H), 1.27 (m, 1.32-1.22, 5H). $^{13}C$ NMR (176 MHz, MeOD) δ 171.5, 157.3, 147.2, 126.5, 124.5, 120.3, 117.1, 97.9, 73.5, 71.9, 70.1, 61.0, 50.0, 48.5, 48.1, 48.0, 47.6, 32.2, 29.7, 28.0, 25.7, 25.1. HRMS (ESI) m/z Calcd. for $C_{21}H_{31}O_8N_4[M+H^+]$: 467.2136, found 467.2123.

Synthesis of (2R,3R,4S,5R,6R)-2-(acetoxymethyl)-6-((6-bromonaphthalen-2-yl)oxy)-tetrahydro-211-pyran-3,4,5-triyl triacetate (STR-V-55)

A solution of beta-D-glucose penta-acetate (3.31 g, 8.49 mmol) and 6-bromo-2-naphthol (2.34 g, 10.18 mmol) in DCM (25 mL) was stirred at 0° C. Boron trifluoride etherate (1.6 mL, 12.74 mmol) was added drop-wisely into the solution. The reaction was removed from ice and stirred at room temperature for 30 minutes. Then, the reaction was heated up to reflux for 48 h. Water (30 mL) was added to the reaction and then extracted with DCM (30 mL). The organic layer was dried with $Na_2SO_4$ and evaporated to dryness. The crude product was purified using column chromatography, eluting with EtOAc:hexane 3:7 to furnish STR-V-55 (yield=523 mg, 80%). $^1H$ NMR (400 MHz, $CDCl_3$) E 7.95 (d, J=2.0 Hz, 1H), 7.71 (d, J=9.0 Hz, 1H), 7.61 (d, J=8.7 Hz, 1H), 7.53 (dd, J=8.8, 2.0 Hz, 1H), 7.43 (d, J=2.5 Hz, 1H), 7.33-7.25 (m, 2H), 5.88 (d, J=3.6 Hz, 1H), 5.75 (t, J=10.3, 1H), 5.19 (t, J=9.4 Hz, 1H), 5.10 (dd, J=10.3, 3.6 Hz, 1H), 4.30-4.23 (m, 1H), 4.13 (ddd, J=10.2, 4.6, 2.1 Hz, 1H), 4.05 (d, J=12.3 Hz, 1H), 2.13-2.00 (m, 9H), 1.99 (s, 3H).

Synthesis of (2R,3R,4S,5R,6R)-2-(acetoxymethyl)-6-((6-ethynylnaphthalen-2-yl)oxy)-tetrahydro-211-pyran-3,4,5-triyl triacetate (STR-V-111)

STR-V-55 (354 mg, 0.63 mmol), TMS-acetylene (0.13 mL, 0.95 mmol), Bis(triphenylphosphine)palladium(II) dichloride (9 mg, 0.013 mmol), copper iodide (3.4 mg, 0.02 mmol) and TPP (2.5 mg, 0.01 mmol) were dissolved into THF (3 mL) and trimethylamine (TEA) (0.17 mL). The reaction was kept stirring in room temperature for 72 h. The solution was filtered through celite and filtrate was evaporated. The crude product was purified through column chromatography, eluting with EtOAc:hexane 1:2 to furnish the silyl intermediate compound (yield=250 mg, 79%). The silyl intermediate (45 mg, 0.08 mmol) was dissolved into DCM and TBAF (0.08 mL, 0.08 mmol) to remove TMS group. The crude product was purified via column chromatography (EtOAc:hexane=3:7), to furnish STR-V-111 as brown solid (yield=30 mg, 75%). $^1H$ NMR (700 MHz, $CDCl_3$) δ 7.94 (d, J=13.6 Hz, 1H), 7.73 (d, J=9.0 Hz, 1H), 7.67 (dd, J=15.7, 8.7 Hz, 1H), 7.59 (d, J=8.7 Hz, 1H), 7.50 (dd, J=13.6, 8.6 Hz, 1H), 7.41 (t, J=3.3 Hz, 1H), 7.30-7.25 (m, 1H), 5.86 (dd, J=10.2, 3.5 Hz, 1H), 5.72 (td, J=9.9, 2.4 Hz, 1H), 5.16 (t, J=9.9 Hz, 1H), 5.08 (dt, J=10.4, 3.4 Hz, 1H), 4.26-4.21 (m, 1H), 4.11 (dd, J=10.6, 4.4 Hz, 1H), 4.03 (d, J=12.5 Hz, 1H), 3.11 (s, 1H), 2.06-2.01 (m, 9H), 1.96 (s, 3H).

Synthesis of N-hydroxy-7-(4-(6-(((2R,3R,4S,5S,6R)-3,4,5-trihydroxy-6-(hydroxymethyl)-tetrahydro-211-pyran-2-yl)oxy)naphthalen-2-yl)-1H-1,2,3-tri-azol-1-yl)heptanamide (STR-V-114)

A mixture of STR-V-111 (29 mg, 0.06 mmol), STR-V-107 (30 mg, 0.07 mmol), copper sulfate (1.5 mg, 0.006 mmol), sodium ascorbate (4.75 mg, 0.024 mmol), in ethanol (1.5 mL) and tert-butanol (1.5 mL) was used for click reaction. The procedure of this reaction and work-up were as described for the synthesis of STR-V-167. Later, the TBDPS-protected intermediate (STR-V-113) (53 mg, 95%) was deprotected using CsF (17 mg, 0.11 mmol) in MeOH (2 mL). Then, the reaction was partitioned between water and ethyl acetate and the layers separated. The ethyl acetate layer was dried over $Na_2SO_4$ and evaporated in vacuo to furnish the hydroxamate intermediate which was deprotected, by dissolving in methanol and NaOMe (25% in methanol) (0.08 mL, 0.34 mmol), following the procedure described for the synthesis of STR-V-53. The desired product STR-V-114 was obtained as white solid (yield=9 mg, 31%). $^1H$ NMR (700 MHz, DMSO-d6) δ 10.33 (s, 1H), 8.14 (s, 1H), 7.95-7.89 (m, 1H), 7.89-7.76 (m, 3H), 7.58 (d, J=9.6 Hz, 2H), 7.35-7.29 (m, 2H), 5.56 (t, J=2.6 Hz, 1H), 3.67 (t, J=9.5 Hz, 1H), 3.56 (d, J=10.5 Hz, 1H), 3.47 (d, J=9.1 Hz, 2H), 3.42 (dt, J=9.8, 2.7 Hz, 1H), 3.31 (t, J=7.0 Hz, 2H), 3.21 (t, J=9.2 Hz, 1H), 3.17 (d, J=1.9 Hz, 0H), 1.93 (t, J=7.4 Hz, 2H), 1.50 (dp, J=22.8, 7.4 Hz, 4H), 1.28 (dq, J=32.1, 7.7 Hz, 6H). HRMS (ESI) m/z Calcd. for $C_{25}H_{33}O_8N_4$[M+H$^+$]: 517.2293, found 517.2272.

Synthesis of N-(2-amino-5-fluorophenyl)-7-(4-(4-(((2R,3R,4S,5S,6R)-3,4,5-trihydroxy-6-(hydroxymethyl)tetrahydro-2H-pyran-2-yl)oxy)phenyl)-1H-1,2,3-triazol-1-yl)heptanamide (STR-V-155)

STR-V-51 (97 mg, 0.21 mmol) was mixed with N-(2-amino-4-fluorophenyl)-7-azidoheptanamide (75 mg, 0.21 mmol) and copper (I) iodide (21 mg, 0.11 mmol) in THF/DMSO (1:1 mL). The solution was purged with argon for 5-10 minutes before the addition of 10 v/v % Hunig's base. The reaction and work-up procedures were as described for the synthesis of STR-V-183 to furnish intermediate product (148 mg, 96%) which was dissolved in MeOH (2 mL) and sodium methoxide (0.34 mL, 1.49 mmol). The procedures for the deprotection of the acetate group and purification were as described for the synthesis of STR-V-53 to furnish STR-V-155 (yield=100 mg 94%). $^1H$ NMR (700 MHz, DMSO-d6) δ 9.09 (s, 1H), 8.50-8.43 (m, 1H), 7.75 (td, J=5.0, 4.5, 2.0 Hz, 2H), 7.18-7.13 (m, 2H), 5.42 (d, J=3.5 Hz, 1H), 5.07 (d, J=6.3 Hz, 1H), 4.96 (dd, J=26.6, 5.3 Hz, 2H), 4.76 (s, 1H), 4.48 (t, J=5.7 Hz, 1H), 4.37 (dt, J=15.9, 8.4 Hz, 2H), 3.63 (td, J=9.2, 4.9 Hz, 1H), 3.56 (dt, J=10.2, 5.3 Hz, 1H), 3.46 (dt, J=9.4, 5.8 Hz, 2H), 3.37 (ddd, J=9.8, 6.3, 3.6 Hz, 1H), 3.19 (td, J=9.0, 5.6 Hz, 1H), 2.30 (dt, J=17.5, 9.3 Hz, 1H), 1.86 (tt, J=17.0, 7.8 Hz, 2H), 1.57 (dp, J=14.1, 7.4 Hz, 1H), 1.39-1.21 (m, 4H). $^{13}C$ NMR (176 MHz, MeOD) δ 173.4, 157.3, 156.4, 155.0, 147.2, 137.4, 137.1, 126.5, 124.6, 120.3, 117.8, 117.2, 112.7, 112.6, 111.6, 111.4, 97.9, 73.6, 73.1, 71.9, 70.1, 61.0, 50.0, 48.0, 47.9, 47.7, 47.6, 47.5, 47.4, 47.3, 35.7, 35.7, 29.7, 28.2, 25.7, 25.2, 25.1. HRMS (ESI) m/z Calcd. for $C_{27}H_{35}O_7N_5F$ [M+H$^+$]: 560.2515, found 560.2503.

Synthesis of N-(2-amino-4-fluorophenyl)-7-(4-(4-(((2R,3R,4S,5S,6R)-3,4,5-trihydroxy-6-(hydroxymethyl)tetrahydro-2H-pyran-2-yl)oxy)phenyl)-1H-1,2,3-triazol-1-yl)heptanamide (STR-V-157)

The reaction of STR-V-51 (104 mg, 0.23 mmol), N-(2-amino-5-fluorophenyl)-7-azidoheptanamide (81 mg, 0.23 mmol), CuI (22 mg, 0.12 mmol) and Hunig's base (0.2 mL, 10 v/v %) in THF-DMSO solution (1:1 mL) as described for the synthesis of STR-V-183 furnished the acetylated intermediate (137 mg, 91%). The acetylated intermediate was deprotected using NaOMe (0.34 mL, 1.51 mmol) in MeOH, following the procedure described for the synthesis of STR-V-53, to furnish STR-V-157 (21 mg, 20%). $^1H$ NMR (700 MHz, DMSO) δ 9.00 (s, 1H), 8.48 (s, 1H), 7.88-7.61 (m, 2H), 7.15 (d, J=8.8 Hz, 2H), 7.07 (dd, J=8.9, 6.6 Hz, 1H), 6.46 (dd, J=11.2, 2.8 Hz, 1H), 6.28 (td, J=8.5, 2.8 Hz, 1H), 5.41 (d, J=3.5 Hz, 1H), 4.37 (t, J=7.1 Hz, 2H), 3.62 (t, J=9.2 Hz, 1H), 3.58-3.53 (m, 1H), 3.46 (dt, J=13.9, 5.9 Hz, 2H), 3.37 (dd, J=9.8, 3.6 Hz, 1H), 3.18 (t, J=9.3 Hz, 1H), 2.27 (t, J=7.5 Hz, 2H), 1.86 (q, J=7.3 Hz, 2H), 1.57 (p, J=7.5 Hz, 2H), 1.32 (dq, J=33.2, 7.8 Hz, 4H). $^{13}C$ NMR (176 MHz, MeOD) δ 173.9, 157.3, 151.7, 147.2, 127.5, 126.5, 120.2, 119.1, 117.1, 103.6, 102.4, 97.9, 73.5, 70.1, 60.9, 49.9, 48.0, 47.8, 47.7, 47.6, 47.5, 47.4, 47.2, 35.5, 29.7, 25.8, 25.3. HRMS (ESI) m/z Calcd. for $C_{27}H_{35}O_7N_5F$ [M+H$^{30}$]: 560.2515, found 560.2511.

Synthesis of N-(2-amino-5-(thiophen-2-yl)phenyl)-7-(4-(4-(((2R,3R,4S,5S,6R)-3,4,5-trihydroxy-6-(hydroxymethyl)tetrahydro-2H-pyran-2-yl)oxy)phenyl)-1H-1,2,3-triazol-1-yl)heptanamide (STR-V-159)

The reaction of STR-V-51 (22 mg, 0.05 mmol), SBI-I-79 (19 mg, 0.23 mmol), CuI (4.8 mg, 0.025 mmol) and Hunig's base (0.02 mL, 10 v/v %) in THF-DMSO solution (1:1 mL) as described for the synthesis of STR-V-183 furnished the acetylated intermediate (15 mg, 37%). The acetylated intermediate was deprotected using NaOMe (0.34 mL, 1.51 mmol) in MeOH, following the procedure described for the synthesis of STR-V-53, to furnish STR-V-159 (1.5 mg, 12%)

Synthesis of (2R,3R,4S,5R,6S)-2-(acetoxymethyl)-6-(4-(1-(7-(hydroxyamino)-7-oxoheptyl)-1H-1,2,3-triazol-4-yl)phenoxy)tetrahydro-2H-pyran-3,4,5-triyl triacetate (STR-V-176)

The reaction of STR-I-190 (67 mg, 0.15 mmol), STR-V-107 (67 mg, 0.16 mmol), copper sulfate (3.73 mg, 0.015 mmol), sodium ascorbate (12 mg, 0.06 mmol), tert-butanol (1.5 mL) and ethanol (1.5 mL), as described for the synthesis of STR-V-167, furnished the TBDPS-protected intermediate (91 mg 66.7%). The TBDPS group of the intermediate (91 mg, 0.1 mmol) was deprotected by treating with cesium fluoride (32 mg, 0.20 mmol) in MeOH (2 mL). The crude was purified using prep TLC, eluting with DCM:MeOH=9:1 to furnish STR-V-176 (15 mg, 24%). $^1H$ NMR (700 MHz, $CDCl_3$) δ 7.81-7.68 (m, 3H), 7.12 (d, J=8.1 Hz, 2H), 5.56-5.51 (m, 2H), 5.43 (dd, J=3.6, 1.8 Hz, 1H), 5.35 (t, J=10.1 Hz, 1H), 4.34 (t, J=6.6 Hz, 2H), 4.25 (dd, J=12.2, 5.2 Hz, 1H), 4.10-4.02 (m, 2H), 2.18 (s, 3H), 2.14-2.08 (m, 2H), 2.04-1.98 (m, 9H), 1.90-1.86 (m, 2H), 1.60 (s, 2H), 1.31 (d, J=26.4 Hz, 6H). $^{13}C$ NMR (176 MHz, MeOD) δ 171.3, 170.2, 155.5, 147.1, 127.0, 125.3, 120.1, 116.9, 95.7, 77.7, 77.5, 77.3, 69.2, 69.1, 65.8, 62.1, 50.2, 49.2, 48.7, 48.6, 48.5, 48.4, 48.2, 48.1, 48.0, 32.4, 29.8, 29.5, 28.1, 25.8, 25.1, 20.3, 20.2. HRMS (ESI) m/z Calcd. for $C_{29}H_{39}O_{12}N_4$[M+H$^+$]: 635.2559, found 635.2552.

Synthesis of N-hydroxy-7-(4-(4-(((2S,3R,4S,5S,6R)-3,4,5-trihydroxy-6-(hydroxymethyl)-tetrahydro-2H-pyran-2-yl)oxy)phenyl)-1H-1,2,3-triazol-1-yl)heptanamide (STR-I-195)

Following the procedure described of the deprotection of acetyl groups in STR-V-53, STR-V-176 (13 mg, 0.02 mmol) was deprotected with NaOMe (0.1 mL, 0.495 mmol) in MeOH (1 mL) to furnish STR-I-195 (4.2 mg, 42%). $^{1}H$ NMR (400 MHz, DMSO-d6) δ 10.31 (s, 4H), 8.47 (s, 1H), 7.73 (d, J=8.7 Hz, 2H), 7.13 (d, J=8.6 Hz, 2H), 5.38 (d, J=1.8 Hz, 1H), 4.34 (t, J=7.1 Hz, 2H), 3.82 (s, 1H), 3.71-3.53 (m, 2H), 3.53-3.20 (m, 4H), 1.94-1.76 (m, 4H), 1.46 (d, J=8.0 Hz, 2H), 1.25 (s, 6H). $^{13}C$ NMR (100 MHz, $CD_3OD$) δ 171.5, 156.6, 147.1, 126.6, 124.5, 120.3, 116.8, 98.7, 74.1, 71.0, 70.5, 66.9, 65.5, 61.3, 49.9, 48.3, 46.4, 32.2, 29.7, 28.0, 25.7, 25.1, 14.1, 7.9. HRMS (ESI) m/z Calcd. for $C_{21}H_{31}O_8N_4[M+H^{30}]$: 467.2136, found 467.2136.

Synthesis of (2R,3R,4S,5R,6S)-2-(acetoxymethyl)-6-((6-bromonaphthalen-2-yl)oxy)-tetrahydro-211-pyran-3,4,5-triyl triacetate (STR-II-30)

The reaction of mannose pentaacetate (1.48 g, 3.8 mmol), 6-bromo-2-naphthol (3.5 g, 15.21 mmol), boron trifluoride etherate (0.72 mL, 5.70 mmol) in DCM (50), as described for the synthesis of STR-V-55, yielded STR-II-30 (1.34 g, 64%) after purification via column chromatography, eluting with 20-40% EtOAc in hexanes. $^{1}H$ NMR (400 MHz, $CDCl_3$) δ 7.94 (d, J=2.3 Hz, 1H), 7.77-7.66 (m, 1H), 7.63-7.38 (m, 3H), 7.31-7.23 (m, 1H), 5.67 (d, J=1.9 Hz, 1H), 5.60 (dd, J=10.0, 3.5 Hz, 1H), 5.49 (dd, J=3.6, 1.9 Hz, 1H), 5.39 (t, J=10.0 Hz, 1H), 4.29 (dd, J=12.0, 5.2 Hz, 1H), 4.16-4.03 (m, 2H), 2.22 (s, 3H), 2.05 (s 3H), 1.95 (s, 3H).

Synthesis of (2R,3R,4S,5R,6S)-2-(acetoxymethyl)-6-((6-ethynylnaphthalen-2-yl)oxy)-tetrahydro-2H-pyran-3,4,5-triyltriacetate (STR-II-34)

STR-II-30 (301 mg, 0.54 mmol), Tetrakis(triphenylphosphine)paladdium(0) (31 mg, 0.027 mmol), TMS-acetylene (0.14 mL, 1.0 mmol) were dissolved in triethylamine (15 mL) and DMF (1 mL). The reaction was purged with argon and heated at 60° C. under argon atmosphere for 12 h. The crude product was filtered through a celite bed, the filtrate was evaporated in vacuo and purified through column chromatography, eluting with EtOAc:hexane 4:6 to furnish the silyl protected intermediate (239 mg, 84%). The silyl protected intermediate (233 mg, 0.43 mmol) was dissolved into THF (2 mL) and 1M TBAF (solution in THF, 0.43 mL, 0.43 mmol) on ice bath. The reaction was stirred at rt for 24 h and the crude was purified using column chromatography, eluting with 35% EtOAc in hexanes to furnish STR-II-34 (129 mg, 60%). $^{1}H$ NMR (400 MHz, $CDCl_3$) δ 7.96 (t, J=1.1 Hz, 1H), 7.74 (dd, J=8.9, 0.7 Hz, 1H), 7.70-7.63 (m, 1H), 7.50 (dd, J=8.5, 1.6 Hz, 1H), 7.45 (d, J=2.5 Hz, 1H), 7.30-7.23 (m, 1H), 5.68 (d, J=1.9 Hz, 1H), 5.60 (dd, J=10.0, 3.5 Hz, 1H), 5.50 (dd, J=3.5, 1.8 Hz, 1H), 5.39 (t, J=10.0 Hz, 1H), 4.29 (dd, J=12.1, 5.3 Hz, 1H), 4.15-4.03 (m, 2H), 3.13 (s, 1H), 2.22 (s, 3H), 2.05 (d, J=1.7 Hz, 6H), 1.94 (s, 3H).

Synthesis of (2R,3R,4S,5R,6S)-2-(acetoxymethyl)-6-((6-(1-(7-(hydroxyamino)-7-oxoheptyl)-1H-1,2,3-triazol-4-yl)naphthalen-2-yl)oxy)tetrahydro-2H-pyran-3,4,5-triyl triacetate (STR-V-177)

The click reaction of STR-II-34 (53 mg, 0.11 mmol), STR-V-107 (50 mg, 0.12 mmol), copper sulfate (3.2 mg, 0.013 mmol), sodium ascorbate (10.3 mg, 0.052 mmol), in ethanol (1.5 mL) and tert-butanol (1.5 mL), followed by the deprotection of the TBDPS group of the intermediate product, as described for the synthesis of STR-V-167, furnished STR-V-177 (15 mg, 20%) after purification by prep TLC, eluting with DCM:MeOH 10:1. $^{1}H$ NMR (700 MHz, $CDCl_3$) δ 8.24 (s, 1H), 7.85 (d, J=9.7 Hz, 2H), 7.80 (d, J=8.8 Hz, 1H), 7.75 (d, J=8.2 Hz, 1H), 7.45 (d, J=2.4 Hz, 1H), 7.23 (s, 3H), 5.58 (dd, J=10.0, 3.6 Hz, 1H), 5.47 (dd, J=3.6, 1.8 Hz, 1H), 5.37 (t, J=10.1 Hz, 1H), 4.38 (s, 2H), 4.27 (dd, J=12.3, 5.5 Hz, 1H), 4.11 (ddd, J=10.2, 5.4, 2.3 Hz, 1H), 4.05 (dd, J=12.3, 2.3 Hz, 1H), 3.21 (t, J=6.8 Hz, 4H), 2.19 (s, 3H), 2.12 (s, 3H), 2.02 (s, 3H), 1.92 (s, 3H), 1.60 (s, 4H), 1.54 (p, J=7.1 Hz, 4H), 1.31 (q, J=14.1, 12.6 Hz, 4H), 1.21 (s, 3H). HRMS (ESI) m/z Calcd. for $C_{33}H_{40}O_{12}N_4Na[M+Na^+]$: 707.2535, found 707.2515.

Synthesis of N-hydroxy-7-(4-(6-((2S,3R,4S,5S,6R)-3,4,5-trihydroxy-6-(hydroxymethyl)-tetrahydro-211-pyran-2-yl)oxy)naphthalen-2-yl)-1H-1,2,3-triazol-1-yl)heptanamide (STR-II-36)

STR-V-177 (219 mg, 0.27 mmol) was deprotected by treating with NaOMe (0.5 mL, 2.19 mmol) in MeOH (2 mL), following the procedure described for the synthesis of STR-V-53, to furnish STR-II-36 (90 mg, 43%). $^{1}H$ NMR (400 MHz, DMSO-d6) δ 10.31 (s, 1H), 8.64 (s, 1H), 8.31 (s, 2H), 7.98-7.80 (m, 4H), 7.56 (d, J=2.4 Hz, 1H), 7.27 (dd, J=8.9, 2.5 Hz, 1H), 5.53 (s, 1H), 4.39 (t, J=6.9 Hz, 2H), 3.87 (dd, J=3.5, 1.8 Hz, 1H), 3.72 (dd, J=9.1, 3.4 Hz, 1H), 3.59 (d, J=10.8 Hz, 1H), 3.55-3.38 (m, 4H), 1.95-1.84 (m, 4H), 1.48 (d, J=7.3 Hz, 2H), 1.40-1.07 (m, 6H). $^{13}C$ NMR (101 MHz, $CD_3OD$) δ 154.62, 134.3, 129.7, 129.4, 127.6, 126.1, 123.8, 123.7, 120.9, 119.2, 110.6, 98.8, 74.1, 70.6, 67.0, 61.3, 50.0, 47.8, 47.2, 47.0, 29.7, 28.0, 25.7, 25.0. HRMS (ESI) m/z Calcd. for $C_{25}H_{33}O_8N_4[M+H^+]$: 517.2293, found 517.2283.

Synthesis of (E)-N-hydroxy-3-(4-(6-(((2S,3R,4S,5S,6R)-3,4,5-trihydroxy-6-(hydroxymethyl)-tetrahydro-211-pyran-2-yl)oxy)naphthalen-2-yl)-1H-1,2,3-triazol-1-yl)acrylamide (STR-V-105)

A mixture of STR-II-30 (202 mg, 0.37 mmol), STR-V-38 (240 mg, 0.73 mmol), palladium (II) acetate (12.3 mg, 0.05 mmol) and tri(o-tolyl)phosphine (32.3 mg, 0.11 mmol) in acetonitrile (3 mL) was purged with argon for 5 minutes. Triethylamine (TEA) (0.13 mL, 0.91 mmol) was added and the mixture was at 90° C. for 5 h with stirring. The solution was filtered through a celite bed and the filtrate was evaporated in vacuo. The crude product was purified using column chromatography eluting with EtOAc:hexanes 6:4 to furnish the intermediate product (87 mg, 29%). The intermediate was dissolved in DCM (1.5 mL), TFA (0.5 mL) and TIPS (0.1 mL) were added and the mixture was stirred at rt for 30 minutes and solvent evaporated off. The residue was dissolved by MeOH (2 mL) and deprotected with NaOMe following the procedure described for the synthesis of STR-V-53, to furnish STR-V-105 (24 mg, 54%). $^{1}H$ NMR (700 MHz, DMSO-d6) δ 10.77 (s, 1H), 8.01 (s, 1H), 7.89 (d, J=8.9 Hz, 1H), 7.83 (d, J=8.6 Hz, 1H), 7.67 (dd, J=8.6, 1.7 Hz, 1H), 7.60-7.56 (m, 2H), 7.30 (dd, J=8.9, 2.5 Hz, 1H), 6.54 (d, J=15.8 Hz, 1H), 5.56 (d, J=1.8 Hz, 1H), 3.89 (dd, J=3.4, 1.9 Hz, 1H), 3.73 (dd, J=9.2, 3.4 Hz, 1H), 3.60 (dd, J=11.7, 2.1 Hz, 1H), 3.52 (t, J=9.4 Hz, 1H), 3.48 (dd, J=11.7, 6.1 Hz, 1H), 3.43 (m, 3.44-3.41, 1H). $^{13}C$ NMR (176 MHz, $CD_3OD$) δ 155.3, 140.5, 135.3, 130.7, 129.8, 129.6, 128.8, 127.6, 123.5, 119.2, 116.4, 110.6, 98.8, 74.2, 71.0, 70.6, 67.0, 61.3, 48.5. HRMS (ESI) m/z Calcd. for $C_{19}H_{22}O_8N$ $[M+H^+]$: 392.1340, found 392.1338.

Synthesis of (E)-N-hydroxy-3-(4-(6-(((2R,3R,4S,5S,6R)-3,4,5-trihydroxy-6-(hydroxyl-methyl)tetra-hydro-2H-pyran-2-yl)oxy)naphthalen-2-yl)-1H-1,2,3-triazol-1-yl)acrylamide (STR-V-115)

The reaction of STR-V-55 (156 mg, 0.28 mmol), STR-V-38 (186 mg, 0.56 mmol), Pd(OAc) (9.43 mg, 0.04 mmol), tri(o-tolyl)phosphine (26.34 mg, 0.08 mmol) and TEA (0.1 mL. 0.74 mmol) in acetonitrile (3 mL), as described for the synthesis of STR-V-105, furnished STR-V-115 (14 mg, 51%). $^{1}$H NMR (700 MHz, DMSO-d6) δ 10.74 (s, 1H), 7.99 (s, 1H), 7.83 (dd, J=45.6, 8.8 Hz, 2H), 7.64 (d, J=8.6 Hz, 1H), 7.55 (d, J=17.3 Hz, 2H), 7.29 (dd, J=8.9, 2.7 Hz, 1H), 6.51 (d, J=15.7 Hz, 1H), 5.73 (d, J=2.7 Hz, 1H), 5.55 (d, J=2.9 Hz, 1H), 3.65 (td, J=9.3, 2.8 Hz, 1H), 3.56-3.52 (m, 1H), 3.46 (d, J=9.5 Hz, 3H), 3.42-3.37 (m, 1H), 3.21-3.17 (m, 1H), 3.14 (d, J=2.8 Hz, 1H). $^{13}$C NMR (176 MHz, $CD_3OD$) δ 156.0, 140.5, 135.3, 130.7, 129.7, 129.6, 128.8, 127.6, 123.5, 119.6, 110.9, 97.9, 73.6, 73.2, 71.9, 70.1, 61.0, 48.5. HRMS (ESI) m/z Calcd. for $C_{19}H_{22}O_8N$ [M+H$^+$]: 392.1340, found 392.1340.

Synthesis of (2S,3R,4S,6R)-4-(dimethylamino)-6-methyltetrahydro-2H-pyran-2,3-diyl diacetate (STR-V-160)

Desosamine (2 g, 11.41 mmol) was mixed with acetic anhydride (3.24 mL, 34.24 mmol) in DCM (60 mL). DMAP (558 mg, 4.57 mmol) was added and the mixture was stirred at rt overnight. The reaction was partitioned between water (50 mL) and EtOAc (30 mL), the two layers were separated and the aqueous layer was extracted with EtOAc (30 mL). The combined EtOAc layer was dried over $Na_2SO_4$ and evaporated in vacuo. The crude was purified using column chromatography eluting with DCM:MeOH 9.5:0.5 to give STR-V-160 as white solid (2.48 g, 80%). $^{1}$H NMR (400 MHz, $CDCl_3$) δ 6.22 (d, J=3.6 Hz, 1H), 5.03 (ddd, J=11.1, 3.7, 0.8 Hz, 1H), 4.04 (dqd, J=12.3, 6.1, 2.2 Hz, 1H), 3.64 (d, J=0.8 Hz, 1H), 3.13 (td, J=11.6, 3.9 Hz, 1H), 2.29 (d, J=0.8 Hz, 6H), 2.13 (d, J=0.9 Hz, 3H), 2.04 (d, J=0.8 Hz, 3H), 1.85 (ddd, J=13.2, 4.2, 2.5 Hz, 1H), 1.48-1.33 (m, 1H), 1.21 (dd, J=6.2, 0.9 Hz, 3H).

Synthesis of (2S,3R,4S,6R)-4-(dimethylamino)-2-(4-iodophenoxy)-6-methyltetrahydro-2H-pyran-3-yl acetate (STR-V-161)

STR-V-160 (104 mg, 0.4 mmol), and 4-iodophenol (135 mg, 0.6 mmol) were dissolved in DCM (3 mL). The mixture was cooled in ice bath for 10 minutes with stirring under argon atmosphere. Boron trifluoride etherate (1 mL, 8 mmol) was added slowly and dropwisely, and the ice bath was removed after 10 minutes stirring, and stirring continues for 12 h at rt. The reaction was partitioned between DCM (30 mL) and water (30 mL) and the two layers separated. The organic layer was washed with water (30 mL), dried over $Na_2SO_4$ and evaporated in vacuo. The crude was purified using column chromatography, eluting ethyl acetate, to furnish STR-V-161 as white solid (161 mg, 95%). H NMR (400 MHz, $CDCl_3$) δ 7.60-7.51 (m, 2H), 6.80-6.72 (m, 2H), 5.07 (dd, J=10.6, 7.5 Hz, 1H), 4.89 (dd, J=7.5, 2.1 Hz, 1H), 3.83-3.54 (m, 1H), 2.82 (ddd, J=12.3, 10.4, 4.3 Hz, 1H), 2.31 (d, J=2.3 Hz, 6H), 2.16-2.03 (m, 3H), 1.87-1.78 (m, 1H), 1.61 (s, 1H), 1.46 (q, J=12.8, 12.2 Hz, 1H), 0.89-0.77 (m, 1H).

Synthesis of (2S,3R,4S,6R)-4-(dimethylamino)-2-(4-ethynylphenoxy)-6-methyltetrahydro-2H-pyran-3-yl acetate (STR-V-163)

STR-V-161 (221 mg, 0.53 mmol) was reacted with TMS-acetylene (0.1 mL, 0.6 5 mmol), catalytic amounts of CuI (4 mg, 0.02 mmol) and Bis(triphenylphosphine)palladium(II) dichloride (7.6 mg, 0.01 mmol), and TEA (1.85 mL, 13.25 mmol) in THF (3 mL). The mixture was stirred at room temperature for 15 h and then filtered through a celite bed. The filtrate was evaporated in vacuo to furnish the crude product (198 mg) which was deprotected by treating potassium carbonate (140 mg, 1.02 mmol) in MeOH (2 mL), purified using column chromatography, eluting with 5-10% MeOH in DCM to furnish STR-V-163 (105 mg, 74%). $^{1}$H NMR (700 MHz, DMSO-d6) δ 7.43 (d, J=8.7 Hz, 2H), 7.08 (d, J=8.8 Hz, 2H), 5.53 (d, J=3.5 Hz, 1H), 4.00 (s, 1H), 3.90 (dqd, J=12.5, 6.2, 2.2 Hz, 1H), 3.72 (d, J=9.2 Hz, 1H), 2.46 (s, 7H), 2.42-2.39 (m, 3H), 1.88 (d, J=12.8 Hz, 1H), 1.25 (s, 1H), 1.18 (d, J=6.2 Hz, 1H), 1.09 (d, J=6.2 Hz, 4H).

Synthesis of (2S,3R,4S,6R)-4-(dimethylamino)-2-(4-(1-(7-(hydroxyamino)-7-oxoheptyl)-1H-1,2,3-triazol-4-yl)phenoxy)-6-methyltetrahydro-2H-pyran-3-yl acetate (STR-V-165)

Following the procedure described for the synthesis of STR-V-53, the reaction of STR-V-163 (47 mg, 0.17 mmol), STR-V-107 (76 mg, 0.18 mmol), copper sulfate (4.26 mg, 0.02 mmol), sodium ascorbate (13 mg, 0.07 mmol), in tert-butanol (1 mL) and methanol (1 mL) furnished the intermediate product (62 mg, 52%) after purification using prep TLC eluting with DCM:MeOH:$NH_4OH$ 8.5:1.5:0.2. The intermediate product (58 mg, 0.08 mmol) was deprotected by treating with CsF (25 mg, 0.17 mmol) in MeOH (2 mL) at rt for 30 minutes. The crude was purified using prep TLC, eluting with 15% MeOH in DCM with 2% $NH_4OH$ (1M) to furnish STR-V-165 (18 mg, 48%). $^{1}$H NMR (700 MHz, DMSO-d6) δ 8.48 (s, 1H), 7.76 (dq, J=8.8, 2.6, 2.1 Hz, 2H), 7.16-7.10 (m, 2H), 5.48 (d, J=3.5 Hz, 1H), 4.35 (t, J=7.1 Hz, 2H), 3.90 (dqd, J=12.6, 6.2, 2.1 Hz, 1H), 3.60 (dd, J=10.6, 3.5 Hz, 1H), 3.00 (ddd, J=12.0, 10.5, 3.9 Hz, 1H), 2.28 (s, 5H), 1.83 (td, J=7.3, 3.5 Hz, 4H), 1.74 (ddd, J=12.8, 4.1, 2.3 Hz, 1H), 1.44 (p, J=7.2 Hz, 2H), 1.29-1.21 (m, 6H), 1.06 (d, J=6.2 Hz, 2H). $^{13}$C NMR (176 MHz, $CD_3OD$) δ 171.7, 157.6, 147.9, 135.8, 134.7, 133.7, 130.7, 128.3, 127.3, 120.3, 117.6, 98.3, 77.9, 69.1, 66.0, 60.7, 53.8, 52.4, 50.7, 49.3, 48.8, 40.6, 32.9, 31.2, 30.3, 28.6, 26.8, 25.6, 21.2, 19.4. HRMS (ESI) m/z Calcd. for $C_{23}H_{36}O_5N_5$[M+H$^+$]: 462.2711, found 462.2696.

EXEMPLIFYING DATA

HDAC Inhibition Data:

| Compound | HDAC1 ($IC_{50}$ nM) | HDAC2 ($IC_{50}$ nM) | HDAC6 ($IC_{50}$ nM) | HDAC8 ($IC_{50}$ nM) |
|---|---|---|---|---|
| STR-V-53 | 24.3 | 60.1 | 3.43 | 843 |
| STR-I-195 | 14.6 | 29.1 | 2.51 | 464 |
| STR-V-165 | 10.3 | 27.5 | 5.22 | 806 |
| STR-V-167 | 31.8 | 66.4 | 2.61 | 311 |
| STR-V-176 | 1.43 | 4.2 | 1.05 | 271 |
| STR-V-177 | 2.20 | 13.2 | 1.65 | 718 |
| STR-II-36 | 3.28 | 10.4 | 0.719 | 319 |
| STR-V-114 | 20.3 | 61.5 | 4.5 | 2130 |
| STR-V-115 | 427 | 1030 | 16.5 | 461 |
| STR-II-35 | 26.8 | 47.1 | 2.03 | 1970 |
| STR-II-29 | 68.2 | 146 | 6.45 | 3590 |
| STR-V-105 | 697 | 1460 | 30.9 | 771 |
| STR-V-121 | 3840 | 6500 | 75.4 | 1820 |
| STR-V-183 | 12.2 | 27.2 | 1.05 | 1960 |
| TSA | 3.56 | 10.1 | 1.70 | 620 |

TSA = Trichostatin A, a positive control for HDAC inhibition

Cell Growth Inhibition Data:
| | Compound name | $IC_{50}$(uM) A549 | $IC_{50}$(uM) Hep-G2 | $IC_{50}$(uM) VERO |
|---|---|---|---|---|
| 1 | 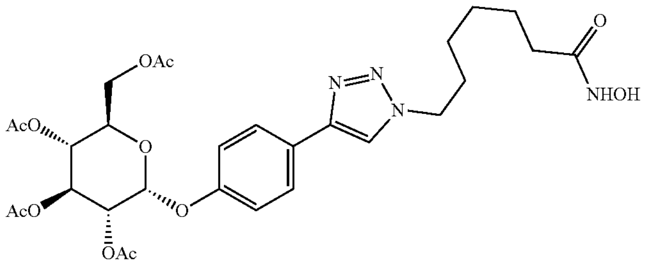 STR-V-167 | NI | 10.1 ± 1.2 | NI |
| 2 | 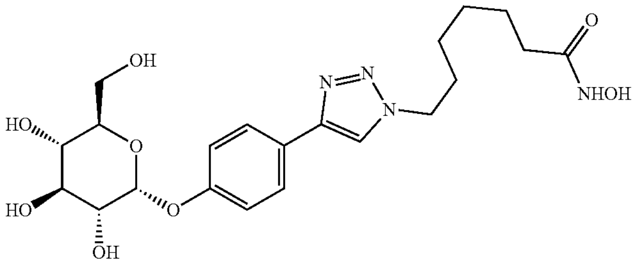 STR-V-53 | 100 ± 0.1 | 10.4 ± 0.6 | 76.4 ± 0.2 |
| 3 | 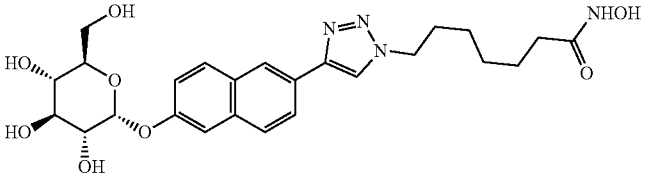 STR-V-114 | 77.2 ± 4.3 | 6.7 ± 1.6 | 34.1 ± 3.0 |
| 4 | 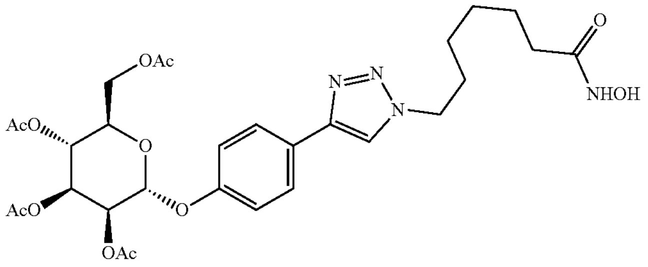 STR-V-176 | 64.7 ± 7.0 | 8.0 ± 0.9 | 77.4 ± 5.6 |
| 5 | 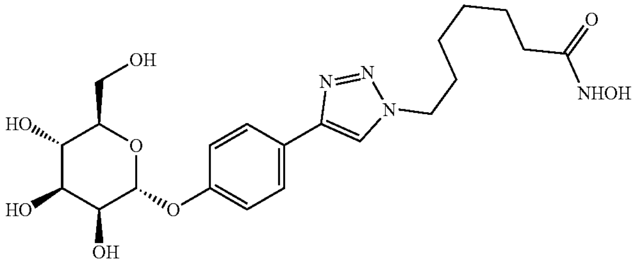 STR-I-195 | NI | 22.3 ± 2.0 | 65.5 ± 8.3 |

-continued
| | Compound name | IC50(uM) A549 | IC50(uM) Hep-G2 | IC50(uM) VERO |
|---|---|---|---|---|
| 6 | 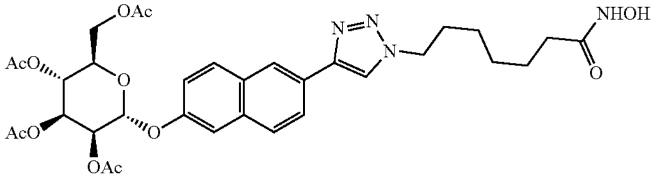 STR-V-177 | 39.6 ± 0.6 | 7.4 ± 0.9 | 19.2 ± 0.9 |
| 7 | 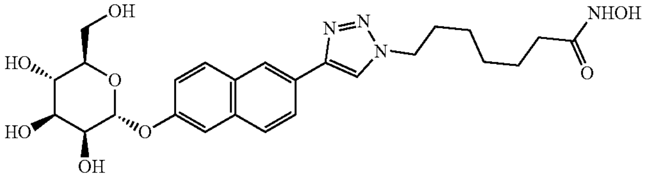 STR-II-36 | 20.1 ± 1.1 | 7.5 ± 0.8 | 33.6 ± 5.5 |
| 8 | 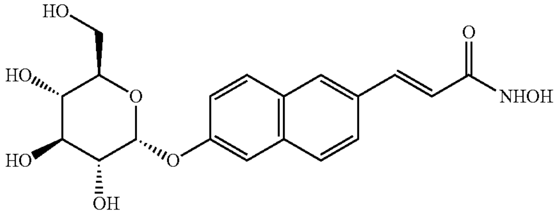 STR-V-115 | NI | 66.1 | 82.1 |
| 9 | 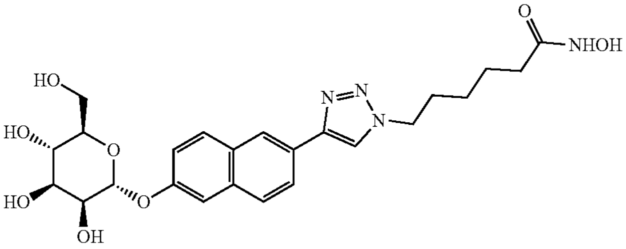 STR-II-35 | 66.7 ± 16.1 | 13.5 ± 2.7 | NI |
| 10 | 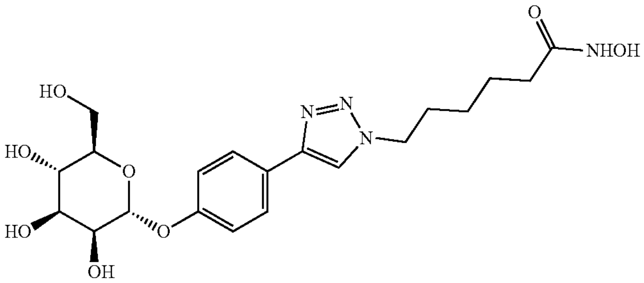 STR-II-29 | NI | 42.8 ± 0.5 | NI |

-continued
| | Compound name | $IC_{50}$(uM) A549 | $IC_{50}$(uM) Hep-G2 | $IC_{50}$(uM) VERO |
|---|---|---|---|---|
| 11 | 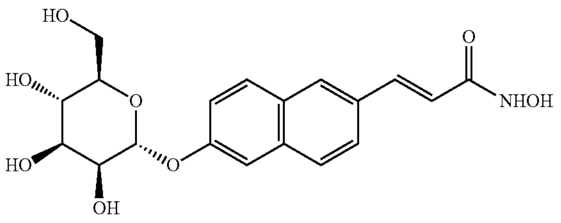 STR-V-105 | NI | 78.5 ± 11.6 | NI |
| 12 | 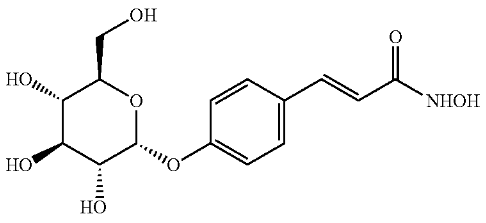 STR-V-121 | NI | 45.3 ± 5.9 | NI |
| 13 | 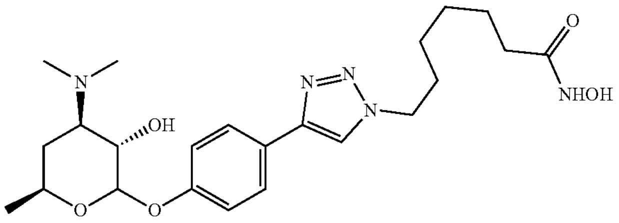 STR-V-165 | 33.7 ± 1.8 | 9.6 ± 3.4 | 76.4 |
| 14 | 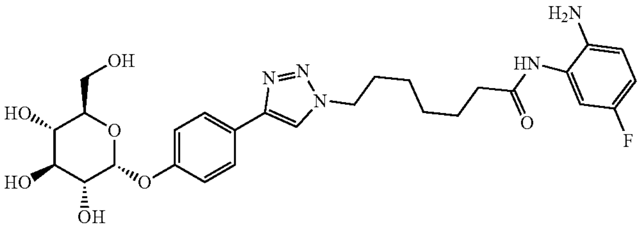 STR-V-155 | 59.9 | NYT | NI |
| 15 | 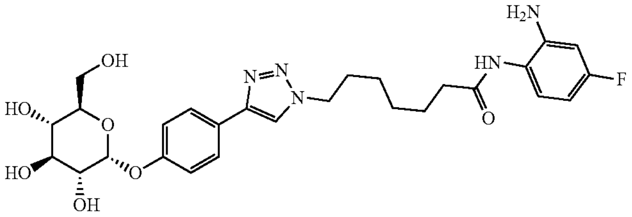 STR-V-157 | NI | ~100 | NI |

-continued

| | Compound name | $IC_{50}$(uM) A549 | $IC_{50}$(uM) Hep-G2 | $IC_{50}$(uM) VERO |
|---|---|---|---|---|
| 16 | 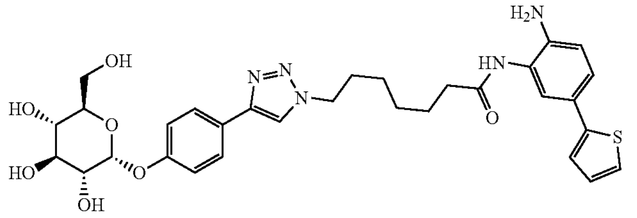 STR-V-159 | 49.5 | NI | NI |

NYT = Not Yet Tested; NI = No Inhibition at 100 uM

Figure 1B:
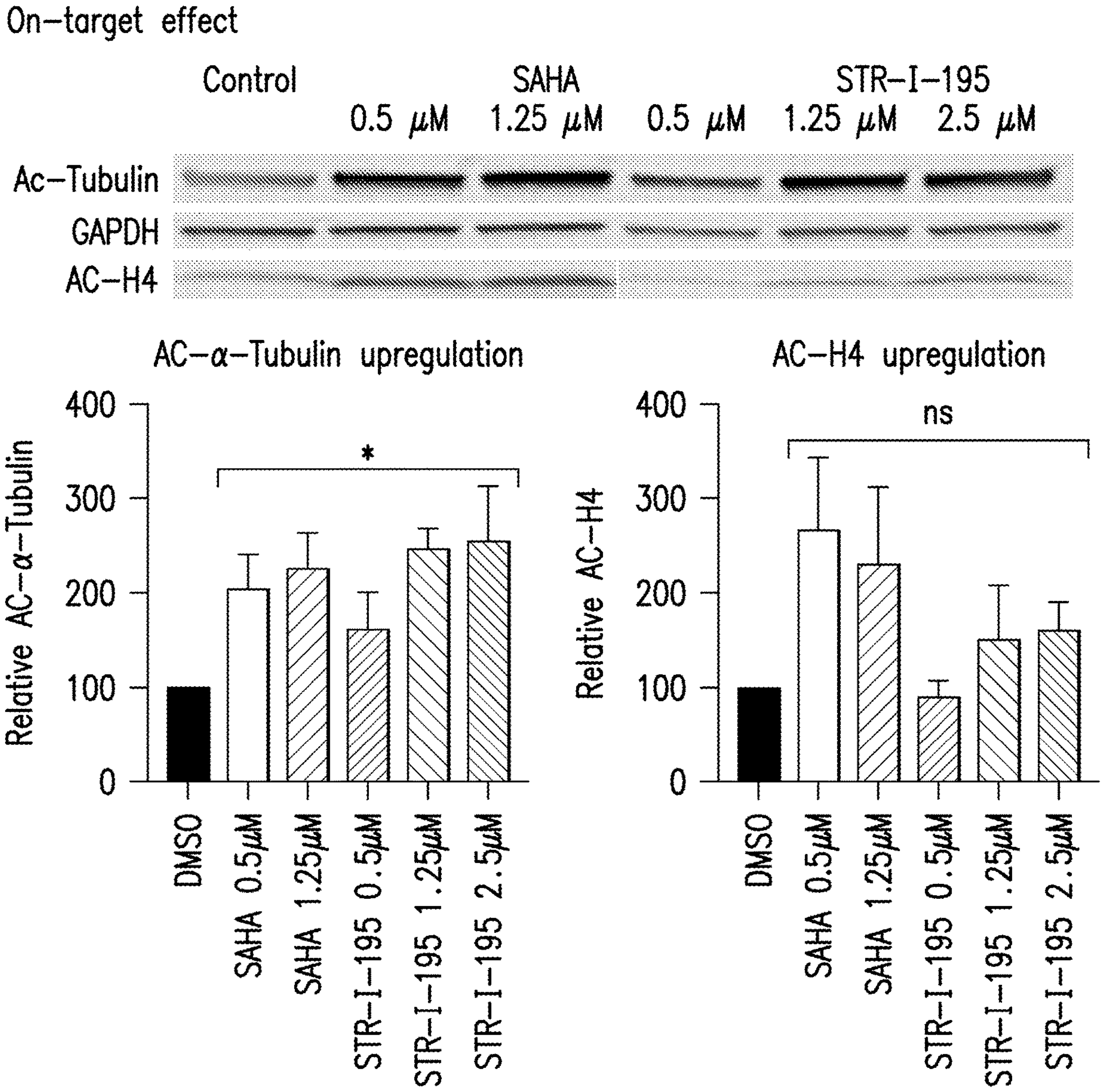

FIG. 1 shows that the Western blot showing evidence of on-target effect (HDAC inhibition) of representative compounds STR-V-53, STR-V-114 and STR-I-195 through upregulation of acetylated tubulin and histone H4 in Hep-G2 cells. SAHA was used as positive control while GAPDH was used to control for protein loading. (1a) Hep-G2 treated with DMSO or 0.1% DMSO solution of SAHA (1.25 μM), STR-V-114 (1.25 μM, 2.5 μM) and STR-V-53 (1.25 μM, 2.5 μM). (1b) Hep-G2 treated with DMSO or 0.1% DMSO solution of SAHA (0.5 μM, 1.25 μM) and STR-I-195 (1.25 μM, 2.5 μM). Cell were treated for 5 h before lysis. Quantifications of gel bands are shown below each gel.

Figure 2A:
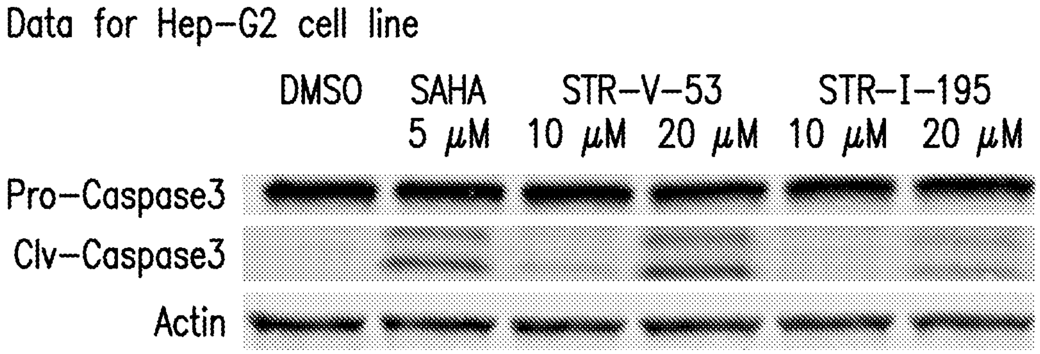
FIG. 2 shows that the representative compounds, STR-V-53, STR-I-195 and positive control SAHA induced apoptosis in the Hep-G2 cell line via caspase 3 activation.
Figure 2B:
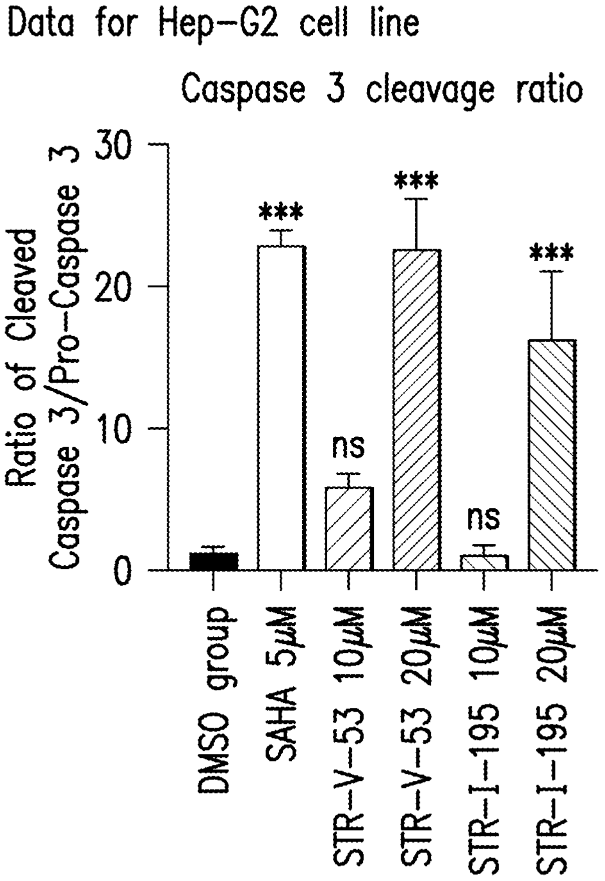

FIG. 2 shows that the Representative compounds STR-V-53, STR-I-195 and positive control SAHA induced apoptosis in the Hep-G2 cell line via caspase 3 activation. Actin was used to control for protein loading. Cells were treated with DMSO or 0.1% DMSO solution of SAHA (5 μM), STR-V-53 (10 and 20 μM), or STR-I-195 (10 and 20 μM) for 18 h. (a) Cropped gel image showing upregulation on cleaved caspase 3 (clv-caspase 3) relative to the DMSO control. (b) Quantification of relative levels of clv-caspase 3. (Bars show mean plus standard deviation; $*P<0.0332$; $P<0.0021$; $*P<0.0002$; $****P<0.00001$).

Figure 3:
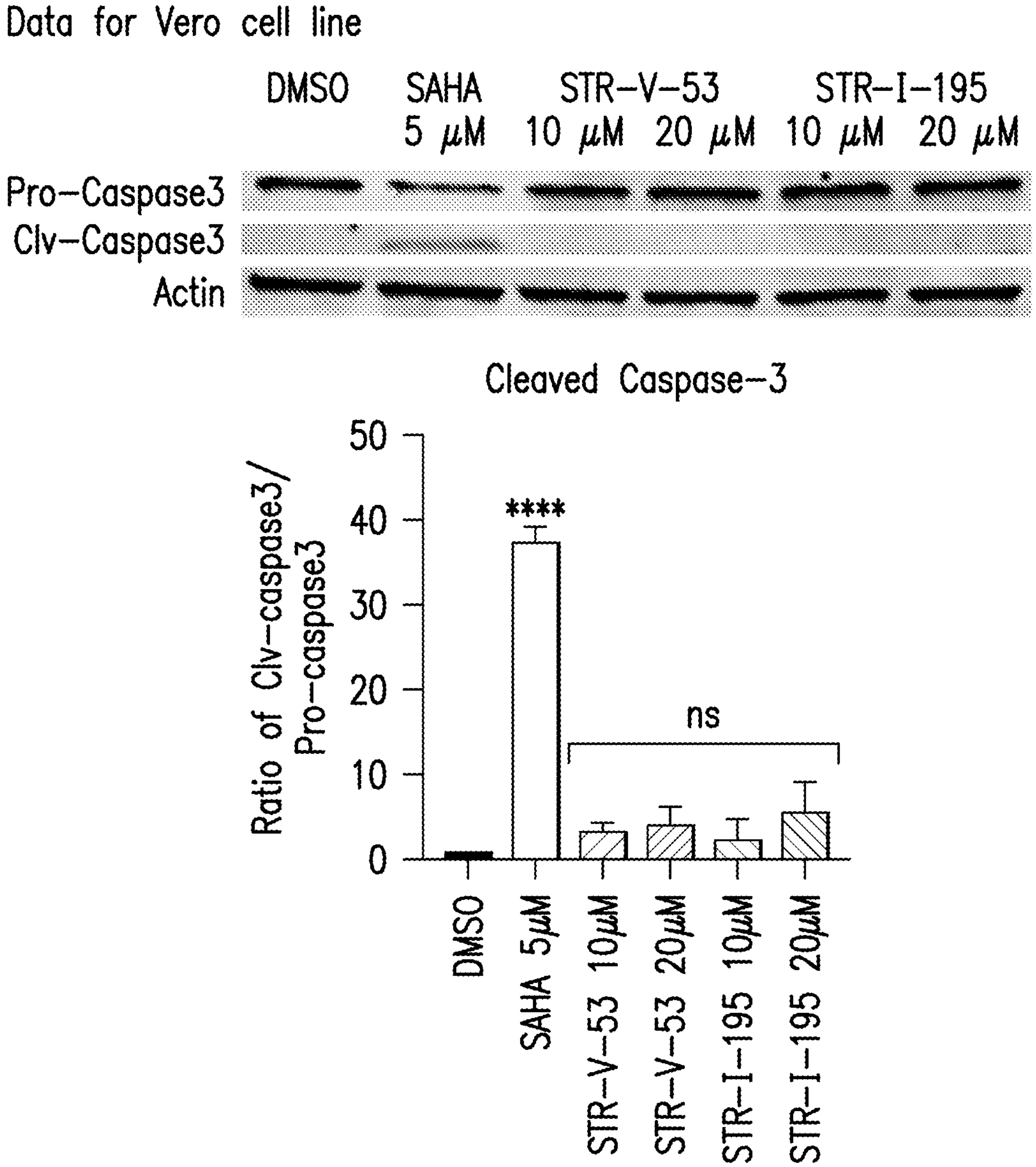
FIG. 3 shows that the representative compounds, STR-V-53 and STR-I-195 did not induce apoptosis (lack of clv-caspase 3) at the tested concentrations in Vero cell line, a model of non-transformed cell line.

FIG. 3 shows that the representative compounds STR-V-53 and STR-I-195 did not induce apoptosis (lack of clv-caspase 3) at the tested concentrations in Vero cell line, a model of non-transformed cell line. Conversely, positive control SAHA induced apoptosis in the Vero cell line via caspase 3 activation (presence of clv-caspase). Actin was used to control for protein loading. Cells were treated with DMSO or 0.1% DMSO solution of SAHA (5 μM), STR-V-53 (10 and 20 μM), or STR-I-195 (10 and 20 μM) for 18 h. Quantification of gel bands are shown below the gel.

Figure 4A:
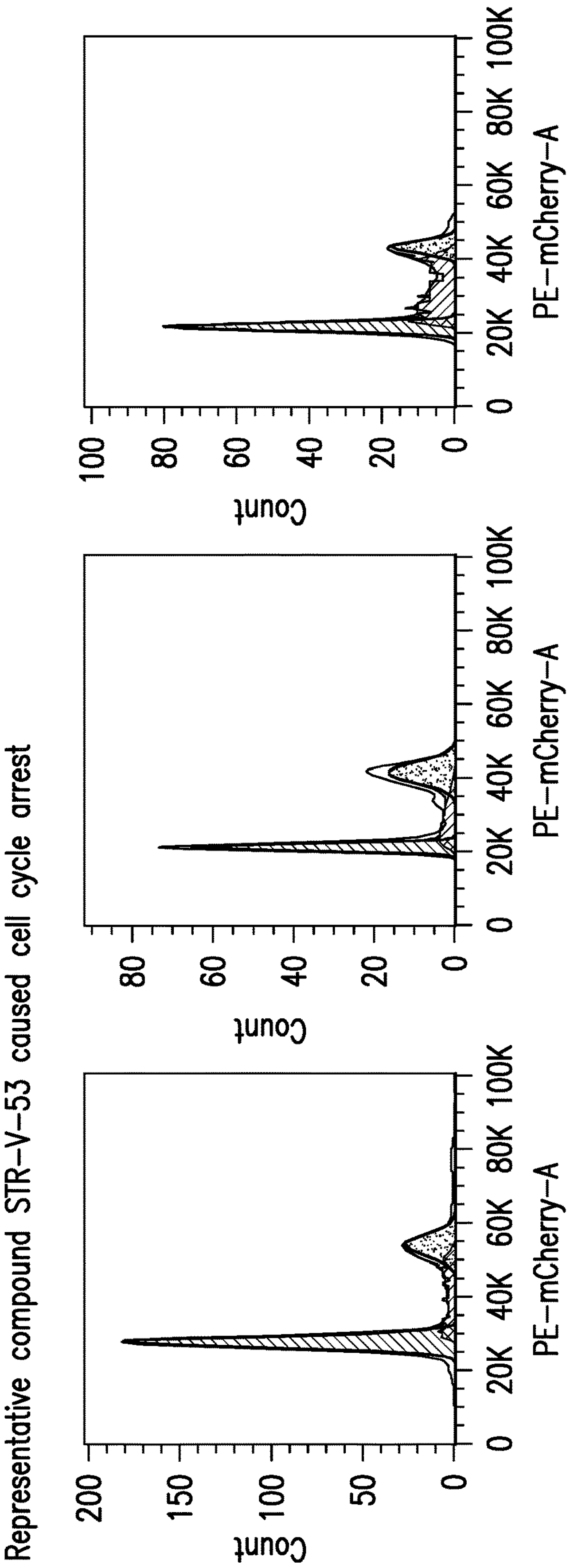
FIG. 4*a* shows that the control group of Hep-G2 (1); SAHA (5 μM) treated group (2); and STR-V-53 (15 μM) treated group (3). The experiment was performed twice and the quantification data was shown.
Figure 4B:
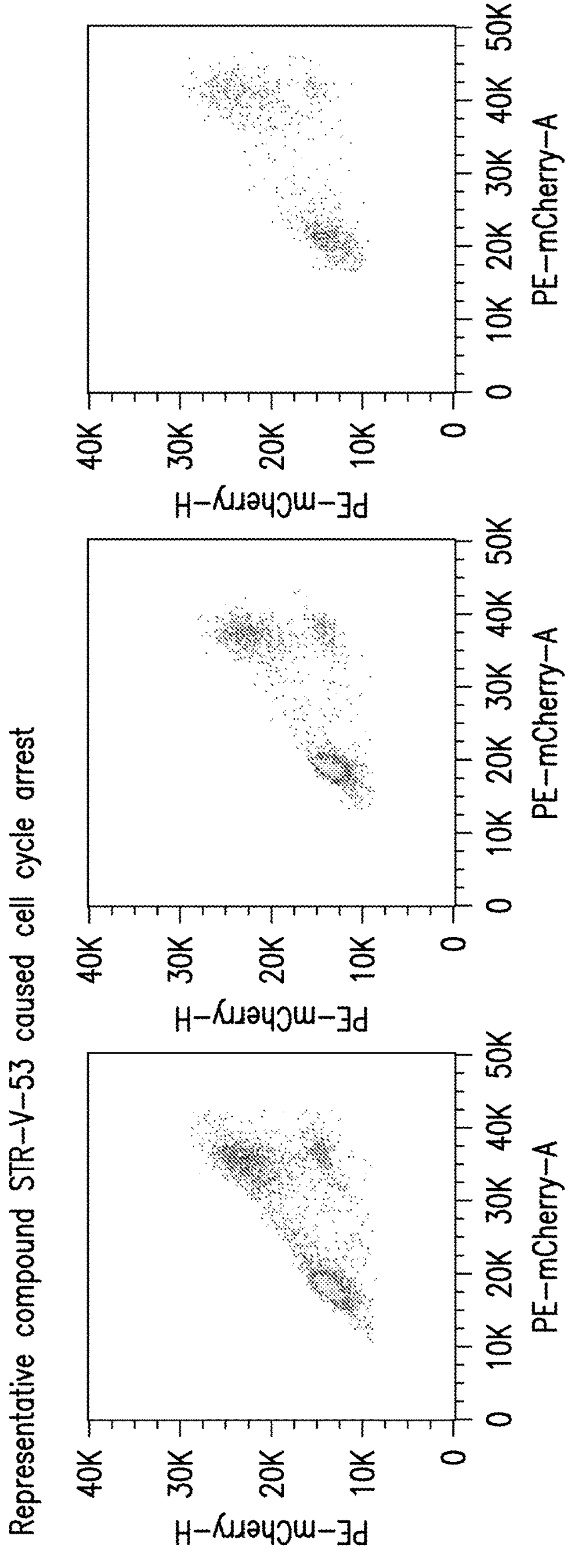
FIG. 4*b* shows the cell distribution in each stage.
Figure 4C:
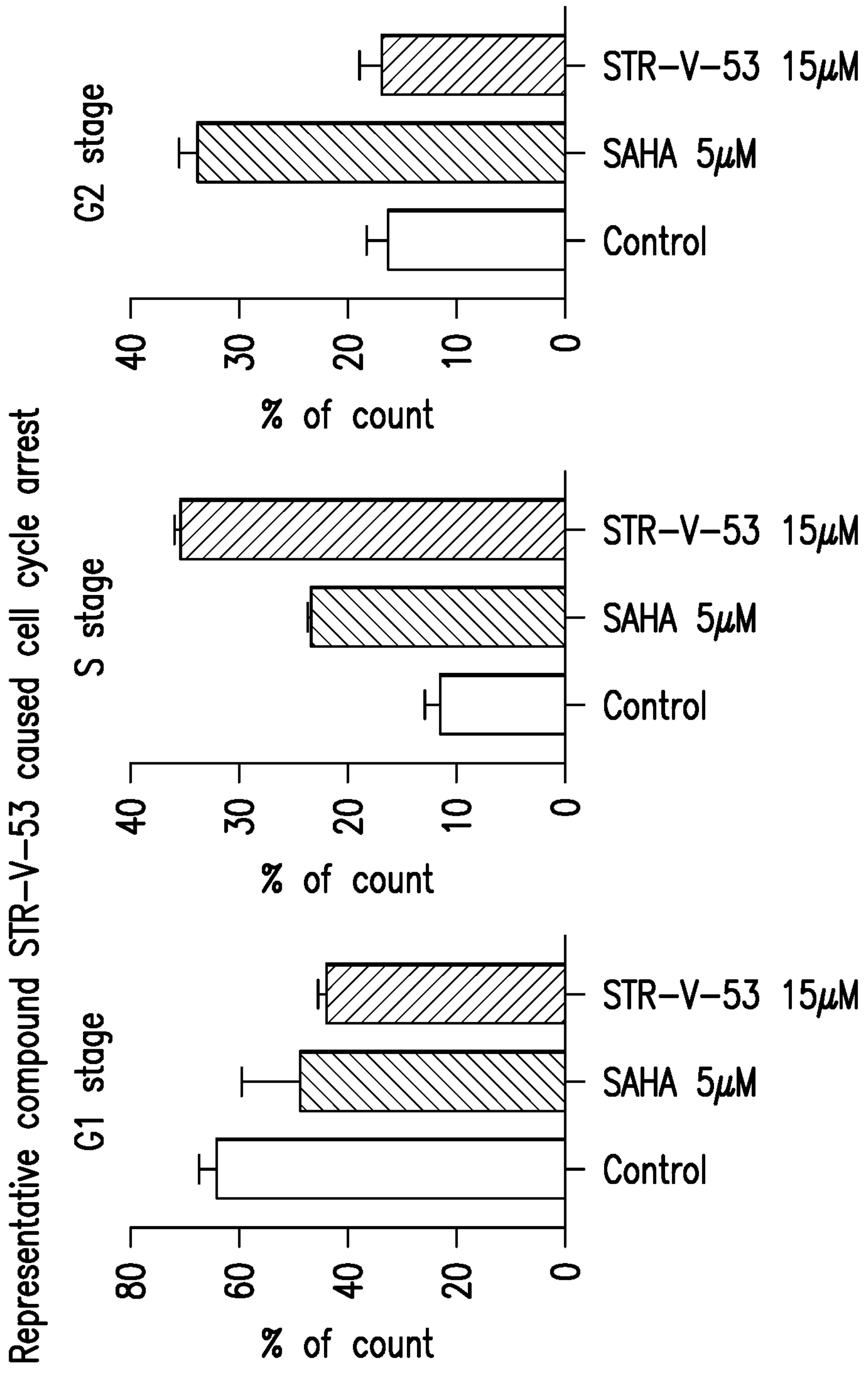
FIG. 4*c* shows the analysis of the percentage cell population in cell cycle stages.
Figure 5A:
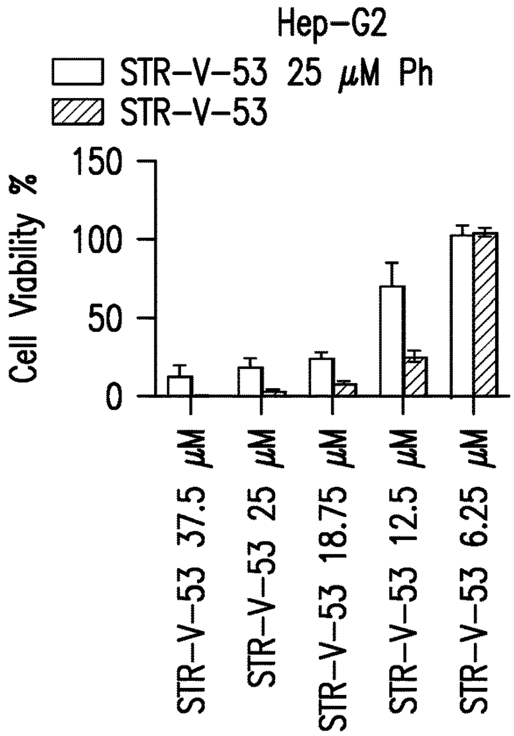
FIG. 5*a* shows Hep-G2 treated by STR-V-53 with or without Ph.
Figure 5B:
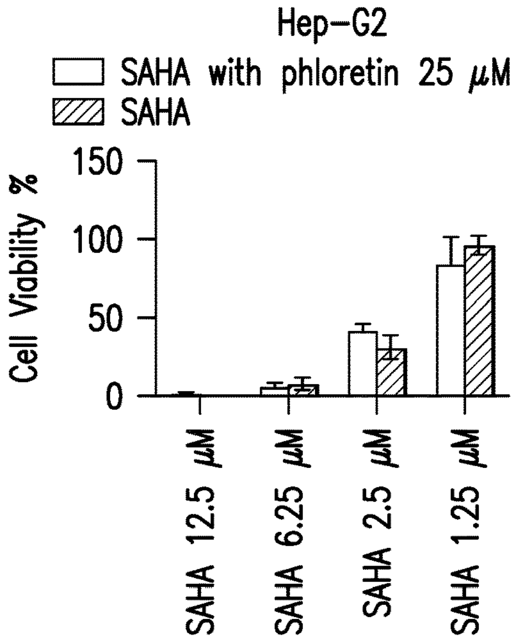
FIG. 5*b* shows Hep-G2 treated by SAHA with or without Ph.
Figure 5C:
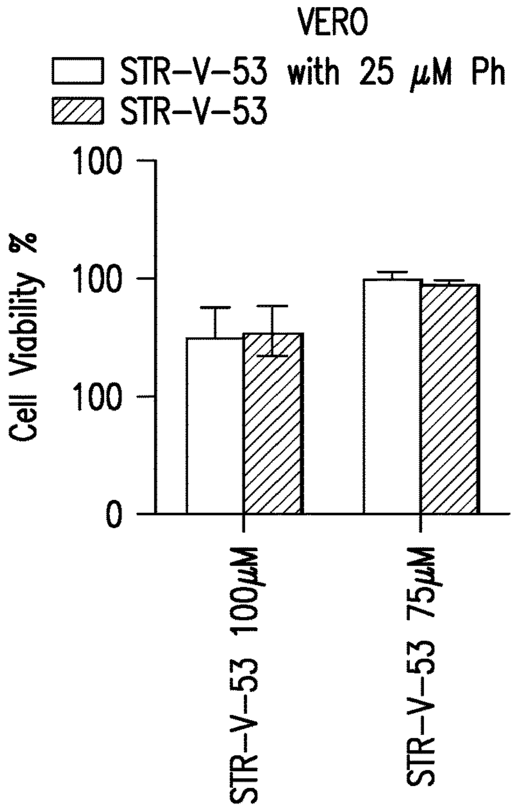
FIG. 5*c* shows VERO treated by STR-V-53 with or without Ph.
Figure 5D:
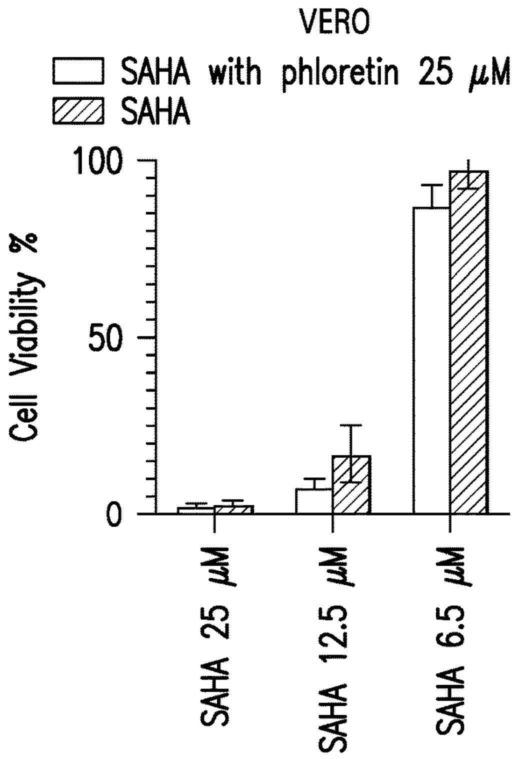
FIG. 5*d* shows VERO treated with SAHA with or without Ph.

FIG. 4 shows that the Cell cycle caused by STR-V-53. Hep-G2 was cultured in all) cm petri dish until 80% confluence. The cell was serum starved overnight before drug treatment. Subsequently, cells were treated with 10 mL of 0.1% DMSO medium, 0.1% DMSO solution of SAHA (5 μM) or STR-V-53 (15 μM), respectively for 48 h. (a) The control group of Hep-G2 (1); SAHA (5 μM) treated group (2); and STR-V-53 (15 μM) treated group (3). The experiment was performed twice and the quantification data shows above. (b) Cell distribution in each stage. (c) Analysis of the percentage cell population in cell cycle stages.

FIG. 5 shows that GLUT2 contributes to the uptake of STR-V-53 in Hep-G2 cell line. Blockage of GLUT2 attenuates the cytotoxicity of STR-V-53 against Hep-G2. Hep-G2 and VERO were treated with Phloretin (Ph) for 24 h prior to incubation with STR-V-53 or SAHA. (a) Hep-G2 treated by STR-V-53 with or without Ph. (b) Hep-G2 treated by SAHA with or without Ph. (c) VERO treated by STR-V-53 with or without Ph. (d) VERO treated with SAHA with or without Ph.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A compound of Formula I:

Formula I

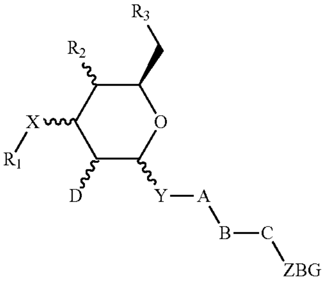

wherein:

X is O or $NCH_3$;

$R_1$ is absent, H, $COCH_3$, $CH_3$, $C_{1-6}$ alkyl, $C_{1-6}$ alkanoate, $C_{2-6}$ carbamate, or $C_{5-6}$ aryl ester, optionally substituted with heteroatoms;

$R_2$ and $R_3$ are each independently H, OH or $OR_4$;

$R_4$ is $C_{1-6}$ alkyl, $C_{1-6}$ alkanoate, $C_{2-6}$ carbamate, or $C_{5-6}$ aryl ester, optionally substituted with heteroatoms;

Y is O;

A is substituted or unsubstituted aryl;

B is absent or 1,2,3-triazolyl;

C is $C_{2-8}$ alkyl, optionally substituted with one or more double bonds;

D is H, F, OH, $OCOCH_3$, $NH_2$, $OR_5$, or $NHR_5$;

$R_5$ is $C_{1-6}$ alkanoate, $C_{2-6}$ carbamate, $C_{5-6}$ aryl ester optionally substituted with heteroatoms, or $C_{5-6}$ fused aryl ester optionally substituted with heteroatoms; and ZBG is selected from

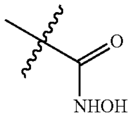
or
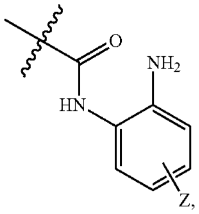

wherein Z is halo or heteroaryl;

or a diastereomer, solvate, or a pharmaceutically acceptable salt thereof.

2. The compound of claim 1, wherein $R_1$ is H, $COCH_3$, or $CH_3$.

3. The compound of claim 1, wherein $R_2$ and $R_3$ are OH.

4. The compound of claim 1, wherein X is O.

5. The compound of claim 1, wherein D is OH or $OCOCH_3$.

6. The compound of claim 1, wherein B is a 1,2,3-triazole.

7. The compound of claim 1, wherein C is five to six $—CH_2—$ groups.

8. The compound of claim 1, wherein ZBG is N-(2-amino-5-fluorophenyl)acylamide.

9. The compound of claim 1, wherein ZBG is N-(2-amino-5-(thiophen-2-yl)phenyl)-acylamide.

10. The compound of claim 1, wherein the compound is selected from the group consisting of:

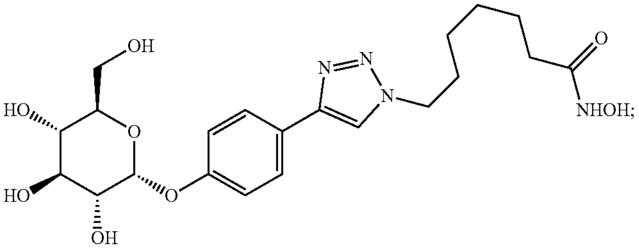

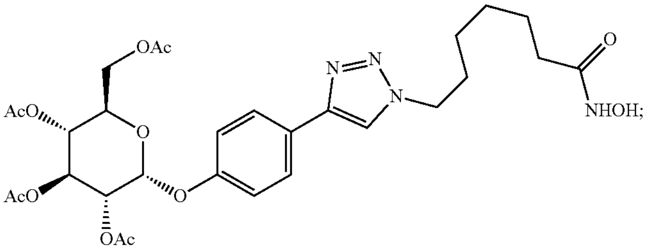

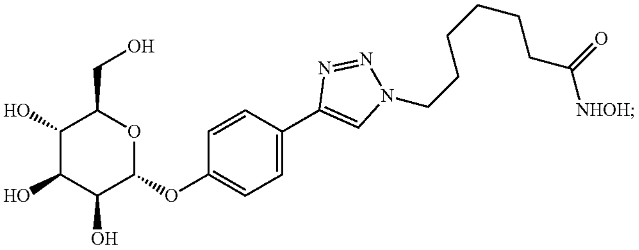

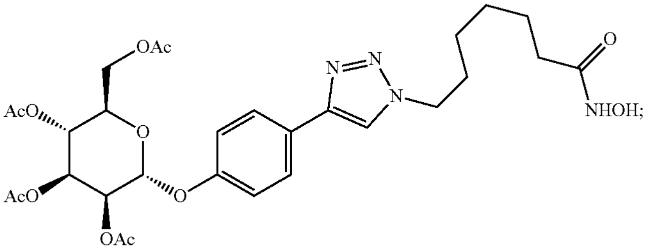

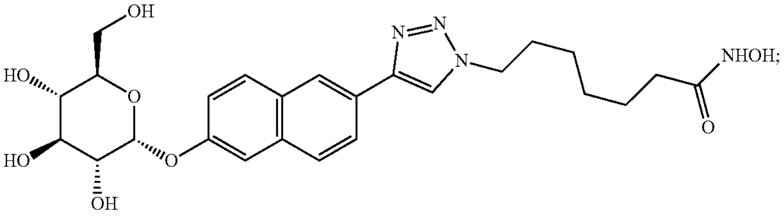

-continued
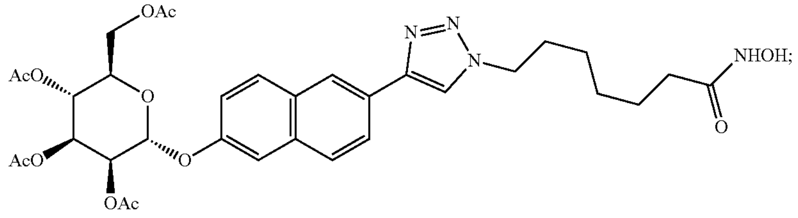
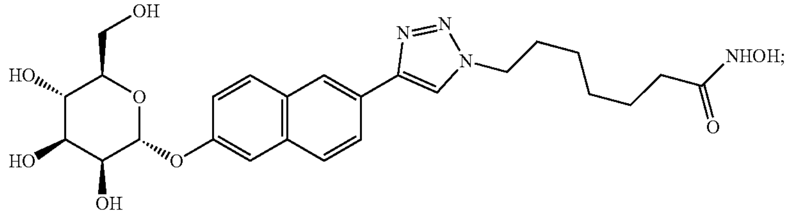
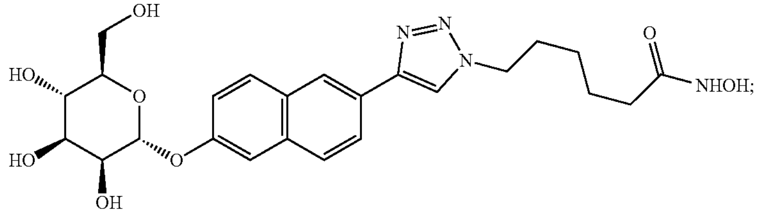
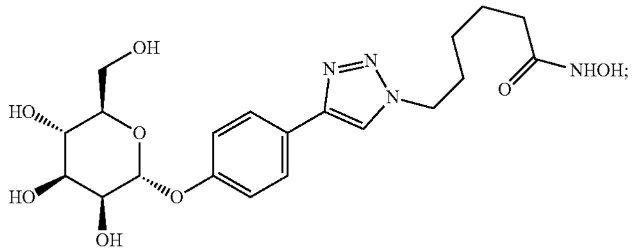
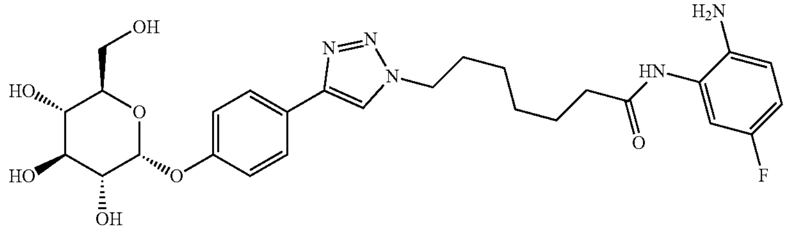
;
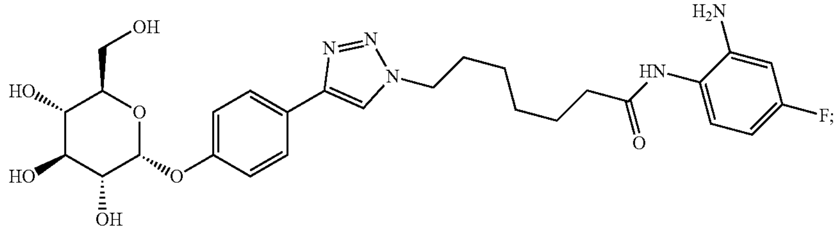
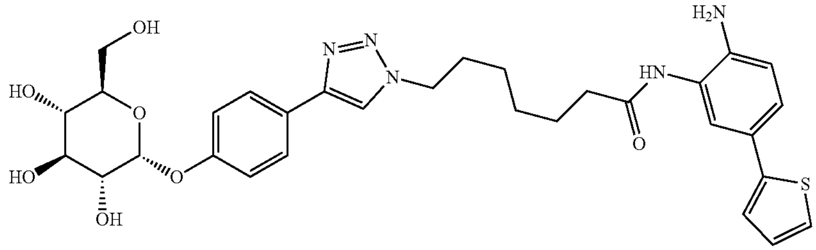
;

-continued

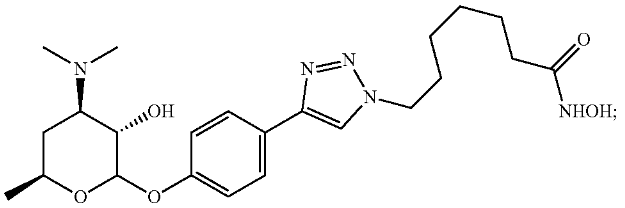

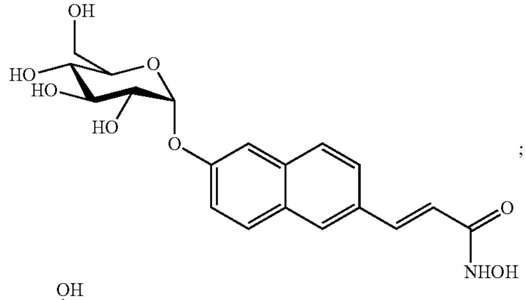

;

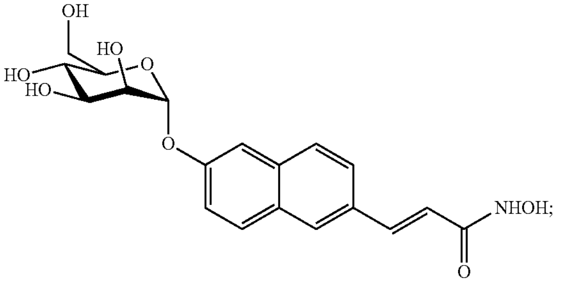

and

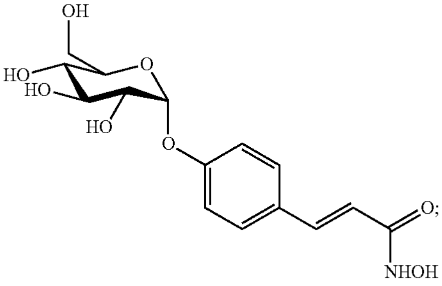

or a diastereomer, solvate, or a pharmaceutically acceptable salt thereof.

11. A pharmaceutical composition comprising:

the compound of claim 1 or a pharmaceutically acceptable salt thereof; and a pharmaceutically acceptable carrier, adjuvant or vehicle.

12. A method of inhibiting histone deacetylases comprising:

contacting the histone deacetylase cells with the compound of claim 1 or a pharmaceutical composition thereof.

13. A method of treating a histone deacetylase dysfunction-driven disease, disorder or condition in a subject in need thereof comprising:

administering to the subject a therapeutically effective amount of the compound of claim 1 or a pharmaceutical composition thereof.

14. The method of claim 13, wherein the histone deacetylase dysfunction-driven disease, disorder or condition is an inflammatory disease or cancer.

15. A method of treating an inflammatory disease, disorder or condition in a subject in need thereof comprising:

administering to the subject a therapeutically effective amount of the compound of claim 1 or a pharmaceutical composition thereof.

16. The method of claim 15, wherein the inflammatory disease is selected from the group consisting of acute and chronic inflammatory disorders, sepsis, acute endotoxemia, encephalitis, Chronic Obstructive Pulmonary Disease (COPD), allergic inflammatory disorders, asthma, pulmonary fibrosis, arthritis, rheumatoid arthritis, osteoarthritis, inflammatory osteolysis, ulcerative colitis, psoriasis, vasculitis, autoimmune disorders, thyroiditis, Meliodosis, (mesenteric) Ischemia reperfusion, and Inflammatory Bowel Disease (IBD).

17. A method of treating a cancer in a subject in need thereof comprising:

administering to the subject a therapeutically effective amount of the compound of claim 1 or a pharmaceutical composition thereof.

18. The method of claim 17, wherein the cancer is selected from the group consisting of squamous cell carcinoma, small-cell lung cancer, non-small cell lung cancer (NSCLC), lung adenocarcinoma, squamous cell lung cancer, liver cancer, and breast cancer.

19. The method of claim 17, wherein the cancer is liver cancer.

* * * * *